(12) United States Patent
Zucherman et al.

(10) Patent No.: US 8,012,209 B2
(45) Date of Patent: Sep. 6, 2011

(54) INTERSPINOUS PROCESS IMPLANT INCLUDING A BINDER, BINDER ALIGNER AND METHOD OF IMPLANTATION

(75) Inventors: James F. Zucherman, San Francisco, CA (US); Ken Y. Hsu, San Francisco, CA (US); Henry A. Klyce, Piedmont, CA (US); Charles J. Winslow, Walnut Creek, CA (US); John J. Flynn, West Milford, NJ (US); Steven T. Mitchell, Pleasant Hill, CA (US); Scott A. Yerby, Montara, CA (US); John A. Markwart, Castro Valley, CA (US)

(73) Assignee: Kyphon Sarl, Neuchatel (CH)

( * ) Notice: Subject to any disclaimer, the term of this patent is extended or adjusted under 35 U.S.C. 154(b) by 1108 days.

(21) Appl. No.: 11/668,217

(22) Filed: Jan. 29, 2007

(65) Prior Publication Data

US 2007/0276500 A1 Nov. 29, 2007

Related U.S. Application Data

(63) Continuation-in-part of application No. 11/095,440, filed on Mar. 31, 2005, and a continuation-in-part of application No. 11/095,680, filed on Mar. 31, 2005.

(60) Provisional application No. 60/612,465, filed on Sep. 23, 2004.

(51) Int. Cl.
*A61F 2/44* (2006.01)
(52) U.S. Cl. ...................................... 623/17.11; 606/246
(58) Field of Classification Search .......... 606/246–249, 606/90; 623/17.11
See application file for complete search history.

(56) References Cited

U.S. PATENT DOCUMENTS

| 1,706,431 A | 3/1929 | Whitliff |
| 2,456,806 A | 12/1948 | Wolffe ............................ 33/174 |
| 2,677,369 A | 5/1954 | Knowles ......................... 128/92 |
| 3,426,364 A | 2/1969 | Lumb .................................... 3/1 |
| 3,643,658 A | 2/1972 | Steinemenan ................ 128/920 |
| 3,648,691 A | 3/1972 | Lumb ........................... 128/920 |
| 3,678,542 A | 7/1972 | Prete, Jr. |
| 3,867,728 A | 2/1975 | Stubstad .............................. 3/1 |
| 3,875,595 A | 4/1975 | Froning ............................... 3/1 |

(Continued)

FOREIGN PATENT DOCUMENTS

CA 2015507 1/1991

(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

(Continued)

*Primary Examiner* — Todd E Manahan
*Assistant Examiner* — Tara R Carter

(57) ABSTRACT

Systems in accordance with embodiments of the present invention can include an implant comprising a spacer for defining a minimum space between adjacent spinous processes, a distraction guide for piercing and distracting an interspinous ligament during implantation, and a binder for limiting or preventing flexion motion of the targeted motion segment. The binder can be secured to a brace associated with the implant during implantation by a capture device. A binder aligner aligns the binder with the implant stabilizing the implant, binder and the adjacent vertebrae.

9 Claims, 36 Drawing Sheets

U.S. PATENT DOCUMENTS

| | | | |
|---|---|---|---|
| 4,003,376 A | 1/1977 | McKay et al. | |
| 4,011,602 A | 3/1977 | Rybicki et al. | |
| 4,034,418 A | 7/1977 | Jackson | 3/1.911 |
| 4,219,015 A | 8/1980 | Steinemann | 128/92 D |
| 4,257,409 A | 3/1981 | Bacal et al. | |
| 4,309,777 A | 1/1982 | Patil | 3/1.91 |
| 4,349,921 A | 9/1982 | Kuntz | 3/1 |
| 4,369,769 A | 1/1983 | Edwards | 128/69 |
| 4,401,112 A | 8/1983 | Rezaian | 128/92 B |
| 4,448,191 A | 5/1984 | Rodnyansky et al. | |
| 4,455,690 A | 6/1984 | Homsy | 3/1 |
| 4,479,491 A | 10/1984 | Martin | 128/92 B |
| 4,501,269 A | 2/1985 | Bagby | 128/96 G |
| 4,502,161 A | 3/1985 | Wall | 623/18 |
| 4,553,273 A | 11/1985 | Wu | 623/18 |
| 4,554,914 A | 11/1985 | Kapp | 128/92 C |
| 4,570,618 A | 2/1986 | Wu | |
| 4,573,454 A | 3/1986 | Hoffman | |
| 4,599,084 A | 7/1986 | Nashef | 623/16 |
| 4,599,086 A | 7/1986 | Doty | 623/17 |
| 4,604,995 A | 8/1986 | Stephens | 128/69 |
| 4,611,582 A | 9/1986 | Duff | 128/69 |
| 4,636,217 A | 1/1987 | Ogilvie | 623/17 |
| 4,643,174 A | 2/1987 | Horiuchi | |
| 4,643,178 A | 2/1987 | Nastari | 128/92 |
| 4,657,550 A | 4/1987 | Daher | 623/17 |
| 4,685,447 A | 8/1987 | Iversen | 128/1 R |
| 4,686,970 A | 8/1987 | Dove et al. | |
| 4,696,290 A | 9/1987 | Steffee | 128/69 |
| 4,714,469 A | 12/1987 | Kenna | 623/17 |
| 4,743,256 A | 5/1988 | Brantigan | 623/17 |
| 4,772,287 A | 9/1988 | Ray | 623/17 |
| 4,776,851 A | 10/1988 | Bruchman et al. | |
| 4,790,303 A | 12/1988 | Steffee | 128/924 M |
| 4,827,918 A | 5/1989 | Olerud | |
| 4,834,757 A | 5/1989 | Brantigan | 623/17 |
| 4,841,959 A | 6/1989 | Ransford | |
| 4,878,915 A | 11/1989 | Brantigan | 623/17 |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,923,471 A | 5/1990 | Morgan | 623/16 |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,888 A | 11/1990 | Scholten | 606/94 |
| 4,998,936 A | 3/1991 | Mehdian | |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,030,220 A | 7/1991 | Howland | |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan | 623/17 |
| 5,074,864 A | 12/1991 | Cozad | 606/54 |
| 5,084,049 A | 1/1992 | Asher | 606/61 |
| 5,088,869 A | 2/1992 | Greenslade | 411/386 |
| 5,092,866 A | 3/1992 | Breard | 606/61 |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,180,381 A | 1/1993 | Aust | 606/61 |
| 5,180,393 A | 1/1993 | Commarmond | |
| 5,192,327 A | 3/1993 | Brantigan | 623/17 |
| 5,201,734 A | 4/1993 | Cozad et al. | |
| 5,258,031 A | 11/1993 | Salib | 623/17 |
| 5,263,953 A | 11/1993 | Bagby | 606/61 |
| 5,275,601 A | 1/1994 | Gogolewski | 606/72 |
| 5,290,312 A | 3/1994 | Kojimoto | 623/17 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,352,225 A | 10/1994 | Yuan | 606/61 |
| 5,360,430 A | 11/1994 | Lin | |
| 5,366,455 A | 11/1994 | Dove | 606/61 |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,372 A | 3/1995 | Holt | 606/61 |
| 5,415,661 A | 5/1995 | Holmes | 606/69 |
| 5,437,672 A | 8/1995 | Alleyne | 606/61 |
| 5,443,514 A | 8/1995 | Steffee | 623/17 |
| 5,454,812 A | 10/1995 | Lin | 606/61 |
| 5,456,722 A | 10/1995 | McLeod | 623/13 |
| 5,458,638 A | 10/1995 | Kuslich | 623/17 |
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,491,882 A | 2/1996 | Walston | 29/419.1 |
| 5,496,318 A * | 3/1996 | Howland et al. | 606/249 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A | 9/1996 | Lahille | 623/17 |
| 5,562,736 A | 10/1996 | Ray | 623/17 |
| 5,571,191 A | 11/1996 | Fitz | 623/17 |
| 5,575,819 A | 11/1996 | Amis | |
| 5,577,995 A | 11/1996 | Walker | 601/120 |
| 5,584,832 A | 12/1996 | Schlapfer | 606/61 |
| 5,593,409 A | 1/1997 | Michelson | 606/61 |
| 5,601,553 A | 2/1997 | Trebing | 606/61 |
| 5,603,713 A | 2/1997 | Aust | 606/61 |
| 5,609,634 A | 3/1997 | Voydeville | 623/17 |
| 5,616,142 A | 4/1997 | Yuan | 606/61 |
| 5,623,984 A | 4/1997 | Nozaki | 164/457 |
| 5,628,756 A | 5/1997 | Barker, Jr. | 606/139 |
| 5,645,597 A | 7/1997 | Krapiva | 623/17 |
| 5,645,599 A | 7/1997 | Samani | 623/17 |
| 5,653,761 A | 8/1997 | Pisharodi | 623/17 |
| 5,658,286 A | 8/1997 | Sava | 606/61 |
| 5,672,177 A | 9/1997 | Seldin | 606/71 |
| 5,674,295 A | 10/1997 | Ray | 623/17 |
| 5,674,296 A | 10/1997 | Bryan | 623/17 |
| 5,676,702 A | 10/1997 | Ratron | 623/17 |
| 5,690,649 A | 11/1997 | Li | |
| 5,702,452 A | 12/1997 | Argenson et al. | |
| 5,702,455 A | 12/1997 | Saggar | 623/17 |
| 5,725,582 A | 3/1998 | Bevan | 623/17 |
| 5,741,261 A | 4/1998 | Moskovitz | 606/79 |
| 5,766,251 A | 6/1998 | Koshino | 623/16 |
| 5,766,252 A | 6/1998 | Henry | 623/17 |
| 5,800,438 A | 9/1998 | Tuke | 606/90 |
| 5,810,815 A | 9/1998 | Morales | |
| 5,824,098 A | 10/1998 | Stein | 623/20 |
| 5,836,948 A | 11/1998 | Zucherman | 606/61 |
| 5,860,977 A | 1/1999 | Zucherman | 606/61 |
| 5,865,846 A | 2/1999 | Bryan | 623/17 |
| 5,876,402 A | 3/1999 | Errico | 606/61 |
| 5,876,404 A | 3/1999 | Zucherman | 606/61 |
| 5,879,396 A | 3/1999 | Walston | 623/21 |
| 5,885,299 A | 3/1999 | Winslow | 606/99 |
| 5,888,224 A | 3/1999 | Beckers | 627/17 |
| 5,888,226 A | 3/1999 | Rogozinski | 623/17 |
| 5,951,555 A | 9/1999 | Rehak | 606/61 |
| 5,976,186 A | 11/1999 | Bao | 623/17 |
| 6,001,130 A | 12/1999 | Bryan | 623/17 |
| 6,022,376 A | 2/2000 | Assell | 623/17 |
| 6,030,162 A | 2/2000 | Huebner | 411/413 |

| | | | | | | |
|---|---|---|---|---|---|---|
| 6,045,552 | A | 4/2000 | Zucherman ............... 606/61 | 6,652,534 B2 | 11/2003 | Zucherman ............... 606/102 |
| 6,045,554 | A | 4/2000 | Grooms ..................... 606/73 | 6,669,729 B2 | 12/2003 | Chin ........................ 623/17.11 |
| 6,048,204 | A | 4/2000 | Klardie ..................... 433/174 | 6,695,842 B2 | 2/2004 | Zucherman ............... 606/61 |
| 6,048,342 | A | 4/2000 | Zucherman ............... 606/61 | 6,699,246 B2 | 3/2004 | Zucherman ............... 606/61 |
| 6,048,344 | A | 4/2000 | Schenk ..................... 606/73 | 6,699,247 B2 | 3/2004 | Zucherman ............... 606/61 |
| 6,068,630 | A | 5/2000 | Zucherman ............... 606/61 | 6,709,435 B2 | 3/2004 | Lin |
| RE36,758 | E | 6/2000 | Fitz ........................... 623/17 | 6,712,819 B2 | 3/2004 | Zucherman ............... 606/61 |
| 6,074,390 | A | 6/2000 | Zucherman ............... 606/61 | 6,712,852 B1 | 3/2004 | Chung ...................... 623/17.11 |
| 6,090,043 | A | 7/2000 | Austin et al. | 6,723,126 B1 | 4/2004 | Berry |
| 6,090,112 | A | 7/2000 | Zucherman ............... 606/61 | 6,730,127 B2 | 5/2004 | Michelson ................ 623/17.16 |
| 6,099,531 | A | 8/2000 | Bonutti ..................... 606/87 | 6,733,534 B2 | 5/2004 | Sherman |
| 6,113,639 | A | 9/2000 | Ray .......................... 623/17.16 | 6,746,485 B1 | 6/2004 | Zucherman ............... 623/17.16 |
| 6,129,730 | A | 10/2000 | Bono ........................ 606/73 | 6,752,831 B2 | 6/2004 | Sybert ...................... 623/13.17 |
| 6,132,464 | A | 10/2000 | Martin ..................... 623/17 | 6,761,720 B1 | 7/2004 | Senegas ................... 606/61 |
| 6,139,550 | A | 10/2000 | Michelson ................ 606/69 | 6,764,491 B2 | 7/2004 | Frey ......................... 606/85 |
| 6,149,652 | A | 11/2000 | Zucherman ............... 606/61 | 6,783,527 B2 | 8/2004 | Drewry .................... 606/61 |
| 6,152,926 | A | 11/2000 | Zucherman ............... 606/61 | 6,796,983 B1 | 9/2004 | Zucherman ............... 606/61 |
| 6,152,927 | A | 11/2000 | Farris ....................... 606/69 | 6,800,670 B2 | 10/2004 | Shen ......................... 522/153 |
| 6,156,038 | A | 12/2000 | Zucherman ............... 606/61 | 6,811,567 B2 | 11/2004 | Reiley ...................... 623/17.11 |
| 6,156,067 | A | 12/2000 | Bryan ...................... 623/17.15 | 6,835,205 B2 | 12/2004 | Atkinson et al. |
| 6,183,471 | B1 | 2/2001 | Zucherman ............... 606/61 | 6,902,566 B2 | 6/2005 | Zucherman ............... 606/61 |
| 6,190,387 | B1 | 2/2001 | Zucherman ............... 606/61 | 6,926,728 B2 | 8/2005 | Zucherman et al. ........ 606/190 |
| 6,190,414 | B1 | 2/2001 | Young ...................... 623/17.15 | 6,936,050 B2 | 8/2005 | Michelson ................ 606/61 |
| 6,193,721 | B1 | 2/2001 | Michelson ................ 606/70 | 6,936,051 B2 | 8/2005 | Michelson ................ 606/61 |
| 6,200,322 | B1 | 3/2001 | Branch ..................... 606/96 | 6,946,000 B2 | 9/2005 | Senegas et al. |
| 6,206,922 | B1 | 3/2001 | Zdeblick ................... 623/17.11 | 6,949,123 B2 | 9/2005 | Reiley ...................... 623/17.11 |
| 6,217,580 | B1 | 4/2001 | Levin ....................... 606/71 | 6,969,390 B2 | 11/2005 | Michelson ................ 606/61 |
| 6,224,602 | B1 | 5/2001 | Hayes ...................... 606/69 | 6,972,019 B2 | 12/2005 | Michelson ................ 606/61 |
| 6,224,607 | B1 | 5/2001 | Michelson ................ 606/96 | 6,974,478 B2 | 12/2005 | Reiley et al. ............. 623/17.11 |
| 6,228,900 | B1 | 5/2001 | Shen ......................... 522/153 | 7,025,789 B2 | 4/2006 | Chow et al. .............. 623/21.11 |
| 6,234,705 | B1 | 5/2001 | Troxell .................... 403/237 | 7,041,105 B2 | 5/2006 | Michelson ................ 606/71 |
| 6,235,030 | B1 | 5/2001 | Zucherman ............... 606/61 | 7,041,135 B2 | 5/2006 | Michelson ................ 623/17.11 |
| 6,238,397 | B1 | 5/2001 | Zucherman ............... 606/61 | 7,041,136 B2 | 5/2006 | Goble et al. .............. 623/17.11 |
| 6,261,296 | B1 | 7/2001 | Aebi ......................... 606/90 | 7,044,952 B2 | 5/2006 | Michelson ................ 606/71 |
| 6,280,444 | B1 | 8/2001 | Zucherman ............... 606/61 | 7,048,736 B2 | 5/2006 | Robinson et al. ......... 606/61 |
| 6,293,949 | B1 | 9/2001 | Justis ........................ 606/61 | 7,063,701 B2 | 6/2006 | Michelson ................ 606/73 |
| 6,306,136 | B1 | 10/2001 | Baccelli .................... 606/61 | 7,063,702 B2 | 6/2006 | Michelson ................ 606/73 |
| 6,312,431 | B1 | 11/2001 | Asfora | 7,074,237 B2 | 7/2006 | Goble et al. .............. 623/17.11 |
| 6,332,882 | B1 | 12/2001 | Zucherman ............... 606/61 | 7,077,844 B2 | 7/2006 | Michelson ................ 606/71 |
| 6,332,883 | B1 | 12/2001 | Zucherman ............... 606/61 | 7,087,083 B2 | 8/2006 | Pasquet et al. |
| 6,352,537 | B1 | 3/2002 | Strnad ...................... 606/61 | 7,087,084 B2 | 8/2006 | Reiley ...................... 623/17.11 |
| 6,364,883 | B1 | 4/2002 | Santilli | 7,090,698 B2 | 8/2006 | Goble et al. .............. 623/17.11 |
| 6,368,351 | B1 | 4/2002 | Glenn ....................... 623/17.15 | 7,097,645 B2 | 8/2006 | Michelson ................ 606/71 |
| 6,371,984 | B1 | 4/2002 | Van Dyke ................. 623/11.11 | 7,101,375 B2 | 9/2006 | Zucherman et al. ...... 606/61 |
| 6,379,355 | B1 | 4/2002 | Zucherman ............... 606/61 | 7,101,398 B2 | 9/2006 | Dooris et al. ............. 623/13.11 |
| 6,383,186 | B1 | 5/2002 | Michelson ................ 606/69 | 7,112,202 B2 | 9/2006 | Michelson ................ 606/71 |
| 6,395,030 | B1 | 5/2002 | Songer ..................... 623/17.11 | 7,115,130 B2 | 10/2006 | Michelson ................ 606/71 |
| 6,398,783 | B1 | 6/2002 | Michelson ................ 606/70 | 7,163,558 B2 | 1/2007 | Senegas et al. |
| 6,402,750 | B1 | 6/2002 | Atkinson et al. | 7,163,561 B2 | 1/2007 | Michelson ................ 623/17.16 |
| 6,402,756 | B1 | 6/2002 | Ralph ....................... 606/71 | 7,201,751 B2 | 4/2007 | Zucherman et al. |
| 6,416,776 | B1 | 7/2002 | Shamie ..................... 424/423 | 7,238,204 B2 | 7/2007 | Le Couedic et al. |
| 6,419,676 | B1 | 7/2002 | Zucherman ............... 606/61 | 7,306,628 B2 | 12/2007 | Zucherman et al. |
| 6,419,677 | B2 | 7/2002 | Zucherman ............... 606/61 | 7,335,203 B2 | 2/2008 | Winslow et al. |
| 6,419,703 | B1 | 7/2002 | Fallin ....................... 623/17.11 | 7,377,942 B2 | 5/2008 | Berry |
| 6,428,542 | B1 | 8/2002 | Michelson ................ 606/70 | 7,442,208 B2 | 10/2008 | Mathieu et al. |
| 6,436,145 | B1 | 8/2002 | Miller ...................... 623/20.34 | 7,445,637 B2 | 11/2008 | Taylor |
| 6,440,169 | B1 | 8/2002 | Elberg ...................... 623/17.16 | 7,458,981 B2 | 12/2008 | Fielding et al. |
| 6,451,019 | B1 * | 9/2002 | Zucherman et al. ........ 606/249 | 7,524,324 B2 | 4/2009 | Winslow et al. |
| 6,451,020 | B1 | 9/2002 | Zucherman ............... 606/61 | 2001/0018614 A1 | 8/2001 | Bianchi |
| 6,454,771 | B1 | 9/2002 | Michelson ................ 606/70 | 2002/0133155 A1 | 9/2002 | Ferree |
| 6,458,131 | B1 | 10/2002 | Ray .......................... 606/61 | 2002/0143331 A1 | 10/2002 | Zucherman et al. |
| 6,478,796 | B2 | 11/2002 | Zucherman ............... 606/61 | 2002/0151895 A1 | 10/2002 | Soboleski et al. |
| 6,500,178 | B2 | 12/2002 | Zucherman ............... 606/61 | 2002/0183756 A1 | 12/2002 | Michelson |
| 6,514,256 | B2 | 2/2003 | Zucherman ............... 606/61 | 2003/0040746 A1 | 2/2003 | Mitchell et al. |
| 6,527,776 | B1 | 3/2003 | Michelson ................ 606/70 | 2003/0065330 A1 | 4/2003 | Zucherman et al. |
| 6,558,423 | B1 | 5/2003 | Michelson ................ 623/17.11 | 2003/0153915 A1 | 8/2003 | Nekozuka et al. |
| 6,558,686 | B1 | 5/2003 | Darouiche ................ 424/423 | 2004/0006391 A1 | 1/2004 | Reiley |
| 6,565,570 | B2 | 5/2003 | Sterett ...................... 606/69 | 2004/0024458 A1 | 2/2004 | Senegas et al. |
| 6,565,605 | B2 | 5/2003 | Goble ....................... 623/17.11 | 2004/0049273 A1 | 3/2004 | Reiley |
| 6,579,318 | B2 | 6/2003 | Varga ....................... 623/17.11 | 2004/0049274 A1 | 3/2004 | Reiley |
| 6,579,319 | B2 | 6/2003 | Goble ....................... 623/17.11 | 2004/0049275 A1 | 3/2004 | Reiley |
| 6,582,433 | B2 | 6/2003 | Yun .......................... 606/61 | 2004/0049276 A1 | 3/2004 | Reiley |
| 6,592,586 | B1 | 7/2003 | Michelson ................ 606/71 | 2004/0049277 A1 | 3/2004 | Reiley |
| 6,610,091 | B1 | 8/2003 | Reiley ...................... 623/17.11 | 2004/0049278 A1 | 3/2004 | Reiley |
| 6,620,163 | B1 | 9/2003 | Michelson ................ 606/61 | 2004/0049281 A1 | 3/2004 | Reiley |
| 6,626,944 | B1 | 9/2003 | Taylor ...................... 623/17.16 | 2004/0087948 A1 | 5/2004 | Suddaby |
| 6,641,585 | B2 | 11/2003 | Sato ......................... 606/61 | 2004/0097931 A1 | 5/2004 | Mitchell |
| 6,645,207 | B2 | 11/2003 | Dixon et al. | 2004/0116927 A1 | 6/2004 | Graf |
| 6,652,527 | B2 | 11/2003 | Zucherman ............... 606/61 | 2004/0122427 A1 | 6/2004 | Holmes |

| | | | | | |
|---|---|---|---|---|---|
| 2004/0143268 A1 | 7/2004 | Falahee | DE | 101 35 771 A1 | 2/2003 |
| 2004/0181229 A1 | 9/2004 | Michelson | EP | 140790 A2 | 10/1984 |
| 2004/0186475 A1 | 9/2004 | Falahee | EP | 146347 A1 | 12/1984 |
| 2004/0210313 A1 | 10/2004 | Michelson | EP | 322334 A1 | 12/1988 |
| 2004/0230201 A1 | 11/2004 | Yuan | EP | 0307241 B1 | 12/1992 |
| 2004/0230304 A1 | 11/2004 | Yuan | EP | 0677277 A2 | 10/1995 |
| 2004/0236334 A1 | 11/2004 | Michelson | EP | 0767636 B1 | 4/1997 |
| 2004/0236335 A1 | 11/2004 | Michelson | EP | 1138268 A1 | 10/2001 |
| 2005/0010293 A1 | 1/2005 | Zucherman et al. | EP | 1330987 A1 | 7/2003 |
| 2005/0027297 A1 | 2/2005 | Michelson | FR | 2623085 | 5/1989 |
| 2005/0027298 A1 | 2/2005 | Michelson | FR | 2625097 | 6/1989 |
| 2005/0049708 A1 | 3/2005 | Atkinson et al. | FR | 2681525 A1 | 3/1993 |
| 2005/0165398 A1 | 7/2005 | Reiley | FR | 2700941 A1 | 8/1994 |
| 2005/0203512 A1 | 9/2005 | Hawkins et al. | FR | 2703239 A1 | 10/1994 |
| 2005/0203624 A1 | 9/2005 | Serhan et al. | FR | 2705227 | 11/1994 |
| 2005/0209603 A1 | 9/2005 | Zucherman et al. | FR | 2707864 A1 | 1/1995 |
| 2005/0228391 A1 | 10/2005 | Levy et al. | FR | 2717066 | 9/1995 |
| 2005/0261768 A1 | 11/2005 | Trieu | FR | 2717068 | 9/1995 |
| 2005/0288672 A1 | 12/2005 | Feree | FR | 2717675 | 9/1995 |
| 2006/0004447 A1 | 1/2006 | Mastrorio et al. | FR | 2722087 A1 | 1/1996 |
| 2006/0015181 A1 | 1/2006 | Elberg | FR | 2722088 | 1/1996 |
| 2006/0064165 A1 | 3/2006 | Zucherman et al. | FR | 2722980 A1 | 2/1996 |
| 2006/0084983 A1 | 4/2006 | Kim | FR | 2724554 | 3/1996 |
| 2006/0084985 A1 | 4/2006 | Kim | FR | 2725892 A1 | 4/1996 |
| 2006/0084987 A1 | 4/2006 | Kim | FR | 2730156 A1 | 8/1996 |
| 2006/0084988 A1 | 4/2006 | Kim | FR | 2775183 A1 | 8/1999 |
| 2006/0085069 A1 | 4/2006 | Kim | FR | 2780269 A1 | 12/1999 |
| 2006/0085070 A1 | 4/2006 | Kim | FR | 2782911 A1 | 3/2000 |
| 2006/0085074 A1 | 4/2006 | Raiszadeh | FR | 2799948 A1 | 4/2001 |
| 2006/0089654 A1 | 4/2006 | Lins et al. | FR | 2806614 A1 | 9/2001 |
| 2006/0089719 A1 | 4/2006 | Trieu | FR | 2806616 A1 | 9/2001 |
| 2006/0106381 A1 | 5/2006 | Ferree et al. | FR | 2816197 A1 | 5/2002 |
| 2006/0106397 A1 | 5/2006 | Lins | FR | 2870107 A1 | 11/2005 |
| 2006/0111728 A1 | 5/2006 | Abdou | GB | 780652 | 8/1957 |
| 2006/0122620 A1 | 6/2006 | Kim | JP | 02-224660 | 9/1990 |
| 2006/0136060 A1 | 6/2006 | Taylor | JP | 09-075381 | 3/1997 |
| 2006/0149278 A1 | 7/2006 | Abdou | JP | 10-179622 | 7/1998 |
| 2006/0184247 A1 | 8/2006 | Edidin et al. | SU | 988281 | 1/1983 |
| 2006/0184248 A1 | 8/2006 | Edidin et al. | SU | 1484348 A1 | 6/1989 |
| 2006/0195102 A1 | 8/2006 | Malandain | WO | WO 90/00037 | 1/1990 |
| 2006/0217726 A1 | 9/2006 | Maxy et al. | WO | WO 91/16018 | 10/1991 |
| 2006/0235386 A1 | 10/2006 | Anderson | WO | WO 94/21185 | 9/1994 |
| 2006/0235387 A1 | 10/2006 | Peterman | WO | WO 94/26192 | 11/1994 |
| 2006/0235532 A1 | 10/2006 | Meunier et al. | WO | WO 94/26193 | 11/1994 |
| 2006/0241601 A1 | 10/2006 | Trautwein et al. | WO | WO 94/26195 | 11/1994 |
| 2006/0241610 A1 | 10/2006 | Lim et al. | WO | WO 95/35067 | 12/1995 |
| 2006/0241613 A1 | 10/2006 | Bruneau et al. | WO | WO 96/08206 A1 | 3/1996 |
| 2006/0241614 A1 | 10/2006 | Bruneau et al. | WO | WO 96/39975 | 12/1996 |
| 2006/0241757 A1 | 10/2006 | Anderson | WO | WO 98/20939 | 5/1998 |
| 2006/0247623 A1 | 11/2006 | Anderson et al. | WO | WO 98/48717 | 11/1998 |
| 2006/0247640 A1 | 11/2006 | Blackwell et al. | WO | WO 98/55038 | 12/1998 |
| 2006/0264938 A1 | 11/2006 | Zucherman et al. | WO | WO 99/26562 | 6/1999 |
| 2006/0271044 A1 | 11/2006 | Petrini et al. | WO | WO 99/40866 | 8/1999 |
| 2006/0271049 A1 | 11/2006 | Zucherman et al. | WO | WO 99/42051 | 8/1999 |
| 2006/0293662 A1 | 12/2006 | Boyer, II et al. | WO | WO 99/56653 | 11/1999 |
| 2006/0293663 A1 | 12/2006 | Walkenhorst et al. | WO | WO 99/59669 | 11/1999 |
| 2007/0043362 A1 | 2/2007 | Malandain et al. | WO | WO 00/04851 | 2/2000 |
| 2007/0162000 A1 | 7/2007 | Perkins | WO | WO 00/13619 | 3/2000 |
| 2007/0191838 A1 | 8/2007 | Bruneau et al. | WO | WO 00/13620 | 3/2000 |
| 2007/0198091 A1 | 8/2007 | Boyer et al. | WO | WO 00/38582 | 7/2000 |
| 2007/0233068 A1 | 10/2007 | Bruneau et al. | WO | WO 00/53126 | 9/2000 |
| 2007/0233081 A1 | 10/2007 | Pasquet et al. | WO | WO 01/26566 A1 | 4/2001 |
| 2007/0233089 A1 | 10/2007 | DiPoto et al. | WO | WO 01/28442 A1 | 4/2001 |
| 2007/0270834 A1 | 11/2007 | Bruneau et al. | WO | WO 02/34120 A2 | 5/2002 |
| 2007/0276369 A1 | 11/2007 | Allard et al. | WO | WO 02/051326 | 7/2002 |
| 2008/0009866 A1 | 1/2008 | Alamin et al. | WO | WO 02/085226 A1 | 10/2002 |
| 2008/0015693 A1 | 1/2008 | Le Couedic | WO | WO 03/057055 A1 | 7/2003 |
| 2008/0161818 A1 | 7/2008 | Kloss et al. | WO | WO 03/101350 A1 | 12/2003 |
| 2008/0183211 A1 | 7/2008 | Lamborne et al. | WO | WO 2004/047691 A1 | 6/2004 |
| 2009/0270918 A1 | 10/2009 | Attia et al. | WO | WO 2004/071358 A1 | 8/2004 |
| | | | WO | WO 2004/098465 A1 | 11/2004 |

FOREIGN PATENT DOCUMENTS

| | | | | | |
|---|---|---|---|---|---|
| DE | 2821678 A1 | 4/1980 | WO | WO 2005/009300 A1 | 2/2005 |
| DE | 3113142 A1 | 1/1982 | WO | 2005037150 | 4/2005 |
| DE | 4012622 C1 | 7/1991 | WO | WO 2005/044118 A1 | 5/2005 |
| DE | 4409833 | 10/1995 | WO | WO 2005/110258 A1 | 11/2005 |
| DE | 4414781 | 11/1995 | WO | WO 2006/064356 A1 | 6/2006 |
| DE | 201 12 123 U1 | 9/2001 | WO | WO 2007/034516 A1 | 3/2007 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochirurgia, Advanced Peripheral Nerve Surgery and Minimal Invasive Spinal Surgery, Alexandre et al., eds., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une experience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Minns, R.J., et al., *Preliminary Design and Experimental Studies of a Novel Soft Implant for Correcting Sagittal Plane Instability in the Lumbar Spine*, SPINE vol. 22, No. 16, pp. 1819-1825, (c) 1997, Lippincott-Raven Publishers.

Haruo Tsuji, et al., *Ceramic Interspinous Block (CISB) Assisted Anterior Interbody Fusion*, Journal of Spinal Disorders, vol. 3, No. 1, pp. 77-86, (c)1990 Raven Press, Ltd., New York.

Richard W. Porter, MD, FRCS, FRCSE, *Spinal Stenosis and Neurogenic Claudication*, SPINE vol. 21, No. 17, pp. 2046-2052, (c)1996, Lippincott-Raven Publishers.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

INTERSPINOUS PROCESS IMPLANT INCLUDING A BINDER, BINDER ALIGNER AND METHOD OF IMPLANTATION

CLAIM OF PRIORITY

This application claims priority to U.S. Provisional Patent Application No. 60/612,465 entitled "Interspinous Process Implant Including a Binder and Method of Implantation," by James F. Zucherman, et al., filed Sep. 23, 2004, and is a Continuation-in-Part of U.S. patent application Ser. No. 11/095,440 entitled "Interspinous Process Implant Including a Binder and Method of Implantation," by James F. Zucherman, et al., filed Mar. 31, 2005, and is a Continuation-in-Part of U.S. patent application Ser. No. 11/095,680 entitled "Interspinous Process Implant Including a Binder and Method of Implantation," by James F. Zucherman, et al., filed Mar. 31, 2005, all of which are incorporated herein by reference.

CROSS-REFERENCE TO RELATED APPLICATIONS

This Patent Application incorporates by reference all of the following co-pending applications and issued patents:

U.S. Patent Application, entitled "Distractible Interspinous Process Implant and Method of Implantation," filed May 20, 2004, Ser. No. 10/850,267;

U.S. Pat. No. 6,419,676, entitled "Spine Distraction Implant and Method," issued Jul. 16, 2002 to Zucherman, et al.;

U.S. Pat. No. 6,451,019, entitled "Supplemental Spine Fixation Device and Method," issued Sep. 17, 2002 to Zucherman, et al.;

U.S. Pat. No. 6,582,433, entitled "Spine Fixation Device and Method," issued Jun. 24, 2003 to Yun;

U.S. Pat. No. 6,652,527, entitled "Supplemental Spine Fixation Device and Method," issued Nov. 25, 2003 to Zucherman, et al;

U.S. Pat. No. 6,695,842, entitled "Interspinous Process Distraction System and Method with Positionable Wing and Method," issued Feb. 24, 2004 to Zucherman, et al;

U.S. Pat. No. 6,699,246, entitled "Spine Distraction Implant," issued Mar. 2, 2004 to Zucherman, et al; and U.S. Pat. No. 6,712,819, entitled "Mating Insertion Instruments for Spinal Implants and Methods of Use," issued Mar. 30, 2004 to Zucherman, et al.

TECHNICAL FIELD

This invention relates to interspinous process implants.

BACKGROUND OF THE INVENTION

As the present society ages, it is anticipated that there will be an increase in adverse spinal conditions which are characteristic of older people. Certain biochemical changes can occur with aging, affecting tissue found throughout the body. In the spine, the structure of the intervertebral disks can be compromised, in part as the structure of the annulus fibrosus of the intervertebral disk weakens due to degenerative effects. Spondylosis (also referred to as spinal osteoarthritis) is one example of a degenerative disorder that can cause loss of normal spinal structure and function. The degenerative process can impact the cervical, thoracic, and/or lumbar regions of the spine, affecting the intervertebral disks and the facet joints. Pain associated with degenerative disorders is often triggered by one or both of forward flexion and hyperextension. Spondylosis in the thoracic region of the spine can cause disk pain during flexion and facet pain during hyperextension. Spondylosis can affect the lumbar region of the spine, which carries most of the body's weight, and movement can stimulate pain fibers in the annulus fibrosus and facet joints.

Over time, loss of disk height can result in a degenerative cascade with deterioration of all components of the motion segment resulting in segment instability and ultimately in spinal stenosis (including, but not limited to, central canal and lateral stenosis). Spinal stenosis results in a reduction in foraminal area (i.e., the available space for the passage of nerves and blood vessels) which compresses the nerve roots and causes radicular pain. Another symptom of spinal stenosis is myelopathy. Extension and ipsilateral rotation further reduces the foraminal area and contributes to pain, nerve root compression and neural injury. During the process of deterioration, disks can become herniated and/or become internally torn and chronically painful. When symptoms seem to emanate from both anterior (disk) and posterior (facets and foramen) structures, patients cannot tolerate positions of extension or flexion.

A common procedure for handling pain associated with degenerative spinal disk disease is the use of devices for fusing together two or more adjacent vertebral bodies. The procedure is known by a number of terms, one of which is interbody fusion. Interbody fusion can be accomplished through the use of a number of devices and methods known in the art. These include screw arrangements, solid bone implant methodologies, and fusion devices which include a cage or other mechanism which is packed with bone and/or bone growth inducing substances. All of the above are implanted between adjacent vertebral bodies in order to fuse the vertebral bodies together, alleviating associated pain.

Depending on the degree of slip and other factors, a physician may fuse the vertebra "as is," or fuse the vertebrae and also use a supplemental device. Supplemental devices are often associated with primary fusion devices and methods, and assist in the fusion process. Supplemental devices assist during the several month period when bone from the adjacent vertebral bodies is growing together through the primary fusion device in order to fuse the adjacent vertebral bodies. During this period it is advantageous to have the vertebral bodies held immobile with respect to each other so that sufficient bone growth can be established. Supplemental devices can include hook and rod arrangements, screw arrangements, and a number of other devices which include straps, wires, and bands, all of which are used to immobilize one portion of the spine relative to another. Supplemental devices have the disadvantage that they generally require extensive surgical procedures in addition to the extensive procedure surrounding the primary fusion implant. Such extensive surgical procedures include additional risks, including risk of causing damage to the spinal nerves during implantation. Spinal fusion can include highly invasive surgery requiring use of a general anesthetic, which itself includes additional risks. Risks further include the possibility of infection, and extensive trauma and damage to the bone of the vertebrae caused either by anchoring of the primary fusion device or the supplemental device. Finally, spinal fusion can result in an absolute loss of relative movement between vertebral bodies.

U.S. Pat. No. 5,496,318 to Howland, et al. teaches supplemental devices for the stabilization of the spine for use with surgical procedures to implant a primary fusion device. Howland '318 teaches an H-shaped spacer having two pieces held together by a belt, steel cable, or polytetrafluoroethane web material, one or both ends of which includes an attachment device fixedly connected with the respective end. Howland '318 teaches that the vertebra are preferably surgically modified to include a square notch to locate the fixation device in a preferred location. Howland '318 has the further disadvantage that the belt, cable or web material must be sized before implantation, increasing the procedure time to include sizing time and reducing the precision of the fit where both ends of the belt, cable or web material include attachment devices (and as such are incrementally sized).

U.S. Pat. No. 5,609,634 to Voydeville teaches a prosthesis including a semi-flexible interspinous block positioned between adjacent spinous processes and a ligament made from the same material. A physician must lace the ligament through the interspinous block and around the spinous processes in a figure of eight, through the interspinous block and around the spinous processes in an oval, and suture the ligament to itself to fix the interspinous block in place. Voydeville has the disadvantage of requiring significant displacement and/or removal of tissue associated with the spinous processes, potentially resulting in significant trauma and damage. Voydeville has the further disadvantage of requiring the physician to lace the interspinous ligament through the interspinous block. Such a procedure can require care and time, particularly because a physician's ability to view the area of interest is complicated by suffusion of blood in the area of interest.

It would be advantageous if a device and procedure for limiting flexion and extension of adjacent vertebral bodies were as simple and easy to perform as possible, and would preferably (though not necessarily) leave intact all bone, ligament, and other tissue which comprise and surround the spine. Accordingly, there is a need for procedures and implants which are minimally invasive and which can supplement or substitute for primary fusion devices and methods, or other spine fixation devices and methods. Accordingly, a need exists to develop spine implants that alleviate pain caused by spinal stenosis and other such conditions caused by damage to, or degeneration of, the spine. Such implants would distract (increase) or maintain the space between the vertebrae to increase the foraminal area and reduce pressure on the nerves and blood vessels of the spine, and limit or block flexion to reduce pain resulting from spondylosis and other such degenerative conditions.

A further need exists for development of a minimally invasive surgical implantation method for spine implants that preserves the physiology of the spine. A still further need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension and flexion.

BRIEF DESCRIPTION OF THE DRAWINGS

Further details of embodiments of the present invention are explained with the help of the attached drawings in which.

DETAILED DESCRIPTION

Figure 1:
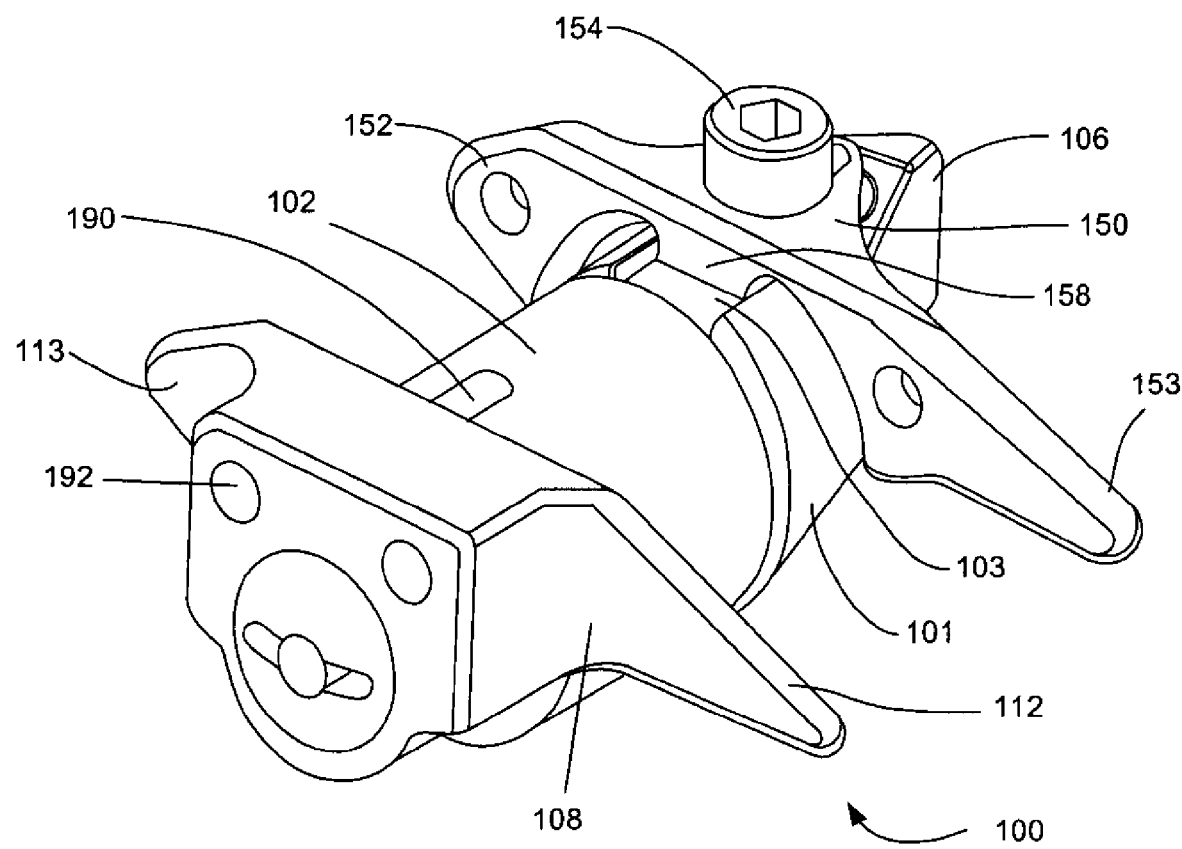
FIG. 1 is a perspective view of an interspinous implant capable of limiting or blocking relative movement of adjacent spinous processes during extension of the spine.

FIG. 1 is a perspective view of an implant as described in U.S. Pat. No. 6,695,842 to Zucherman, et al. and U.S. Pat. No. 6,712,819 to Zucherman et al., both incorporated herein by reference. The implant 100 has a main body 101. The main body 101 includes a spacer 102, a first wing 108, a lead-in tissue expander 106 (also referred to herein as a distraction guide) and an alignment track 103. The main body 101 is inserted between adjacent spinous processes. Preferably, the main body 101 remains (where desired) in place without attachment to the bone or ligaments.

The distraction guide 106 includes a tip from which the distraction guide 106 expands, the tip having a diameter sufficiently small such that the tip can pierce an opening in an interspinous ligament and/or can be inserted into a small initial dilated opening. The diameter and/or cross-sectional area of the distraction guide 106 then gradually increases until it is substantially similar to the diameter of the main body 101 and spacer 102. The tapered front end eases the ability of a physician to urge the implant 100 between adjacent spinous processes. When urging the main body 101 between adjacent spinous processes, the front end of the distraction guide 106 distracts the adjacent spinous processes and dilates the interspinous ligament so that a space between the adjacent spinous processes is approximately the diameter of the spacer 102.

The shape of the spacer 102 is such that for purposes of insertion between the spinous processes, the spinous processes need not be altered or cut away in order to accommodate the spacer 102. Additionally, associated ligaments need not be cut away and there is little or no damage to the adjacent or surrounding tissues. As shown in FIG. 1, the spacer 102 is elliptically shaped in cross-section, and can swivel about a central body (also referred to herein as a shaft) extending from the first wing 108 so that the spacer 102 can self-align relative to the uneven surfaces of the spinous processes. Self-alignment can ensure that compressive loads are distributed across the surface of the bone. As contemplated in Zucherman '842, the spacer 102 can have, for example, a diameter of six millimeters, eight millimeters, ten millimeters, twelve millimeters and fourteen millimeters. These diameters refer to the height by which the spacer distracts and maintains apart the spinous process. For an elliptically shaped spacer, the selected height (i.e., diameter) is the minor dimension measurement across the ellipse. The major dimension is transverse to the alignment of the spinous process, one above the other.

The first wing 108 has a lower portion 113 and an upper portion 112. As shown in FIG. 1, the upper portion 112 is shaped to accommodate the anatomical form or contour of spinous processes (and/or laminae) of the L4 (for an L4-L5 placement) or L5 (for an L5-S1 placement) vertebra. The same shape or variations of this shape can be used to accommodate other motion segments. The lower portion 113 can also be rounded to accommodate the spinous processes. The lower portion 113 and upper portion 112 of the first wing 108 act as a stop mechanism when the implant 100 is inserted between adjacent spinous processes. The implant 100 cannot be inserted beyond the surfaces of the first wing 108. Additionally, once the implant 100 is inserted, the first wing 108 can prevent side-to-side, or posterior-to-anterior movement of the implant 100. The first wing 108 can further include one or more alignment holes 103 and one or more locking pin holes 104 for receiving pins of a main body insertion instrument (not shown).

The implant 100 further includes an adjustable wing 150 (also referred to herein as a second wing). The adjustable wing 150 has a lower portion 152 and an upper portion 153. Similar to the first wing 108, the adjustable wing 150 is designed to accommodate the anatomical form or contour of the spinous processes and/or lamina. The adjustable wing 150 is secured to the main body 101 with a fastener 154. The adjustable wing 150 also has an alignment tab 158. When the adjustable wing 150 is initially placed on the main body 101, the alignment tab 158 engages the alignment track 103. The alignment tab 158 slides within the alignment track 103 and helps to maintain the adjustable wing 150 substantially parallel with the first wing 108. When the main body 101 is inserted into the patient and the adjustable wing 150 has been attached, the adjustable wing 150 also can prevent side-to-side, or posterior-to-anterior movement.

Figure 2A:
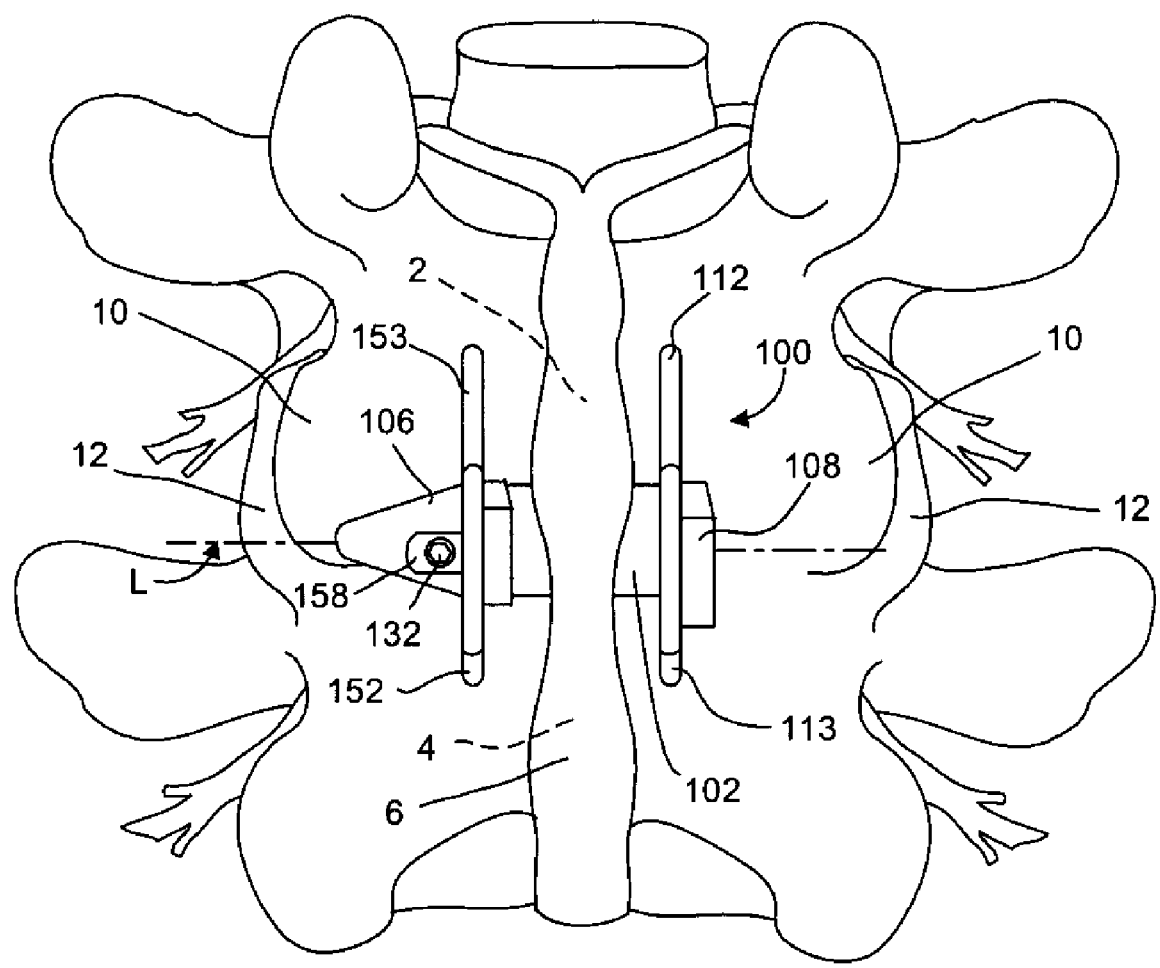
FIG. 2A is a posterior view of the implant of FIG. 1 positioned between adjacent spinous processes.

FIG. 2A illustrates an implant 100 positioned between adjacent spinous processes extending from vertebrae of the lumbar region. The implant 100 is positioned between inferior articular processes 10 associated with the upper vertebrae and superior articular processes 12 associated with the lower vertebrae. The superspinous ligament 6 connects the upper and lower spinous processes 2,4. The implant 100 can be positioned without severing or otherwise destructively disturbing the superspinous ligament 6.

Figure 2B:
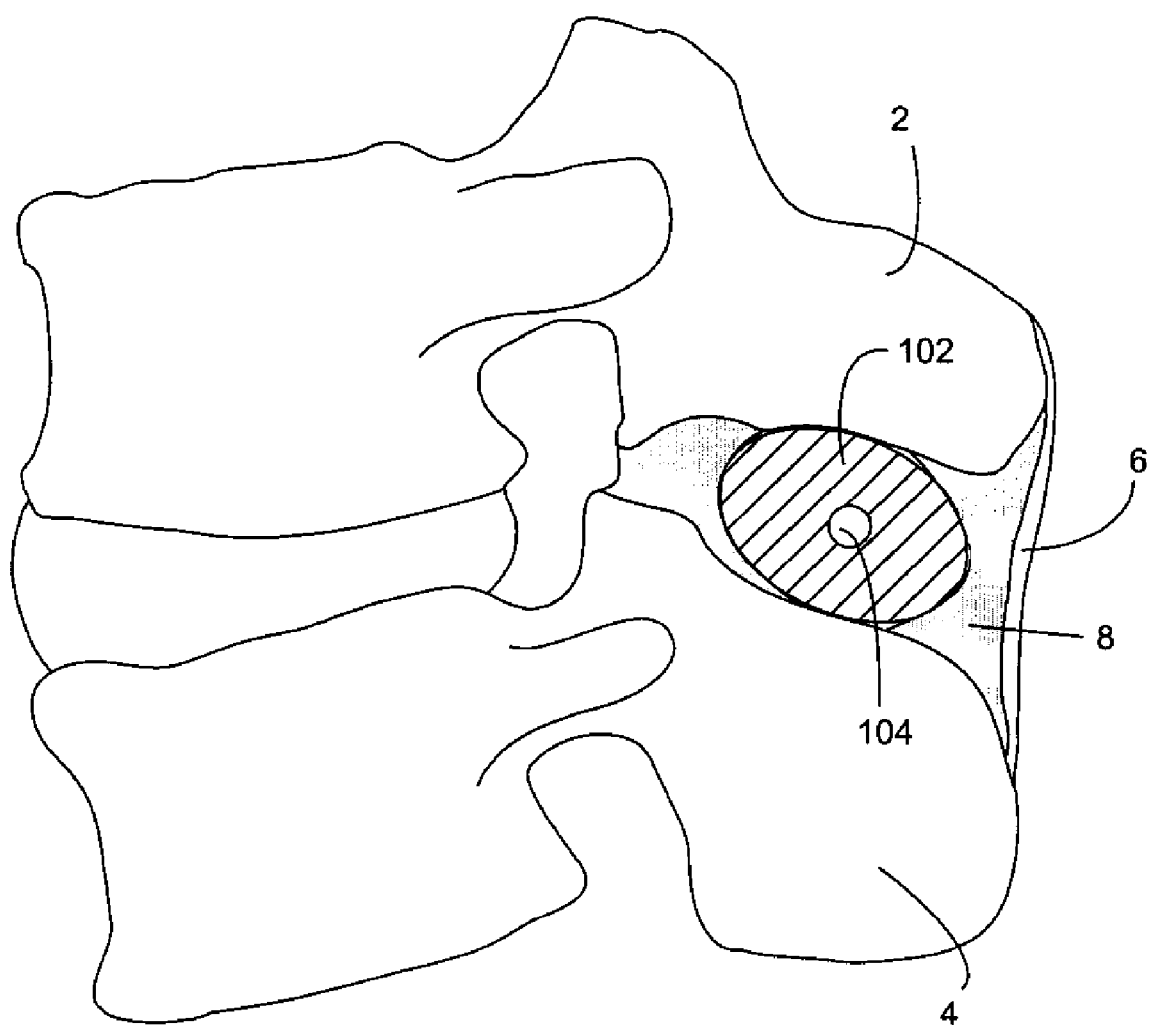
FIG. 2B is a cross-sectional side view of a spacer of the interspinous implant of FIGS. 1 and 2A positioned between spinous processes.
Figure 2C:
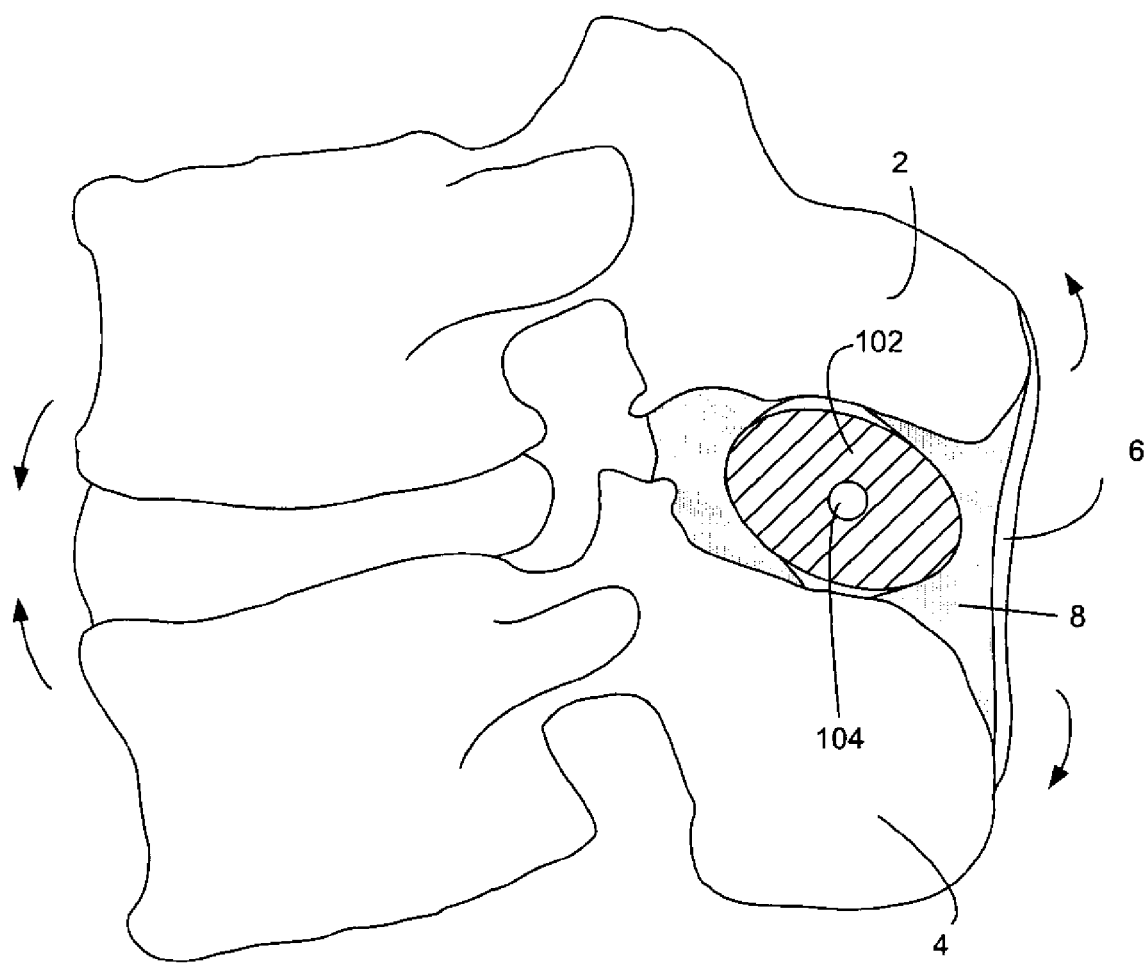
FIG. 2C is a cross-sectional view of the spacer of FIG. 2B during flexion of the spine.

Referring to FIG. 2B, the spacer 102 of the implant 100 of FIG. 2A is shown in cross-section. The spacer 102 defines a minimum space between adjacent spinous processes 2,4. During extension the spacer 102 limits or blocks relative movement between the adjacent spinous processes 2,4, limiting or blocking the collapse of the space between the spinous processes 2,4. Such support can alleviate symptoms of degenerative disorders by preventing a reduction of the foraminal area and compression of the nerve roots, or by avoiding aggravation of a herniated disk, or by relieving other problems. However, as shown in FIG. 2C, the implant 100 permits flexion, which in some degenerative disorders (for example in cases of spinal stenosis) can relieve some symptoms. As can be seen, during flexion the spacer 102 can float between the spinous processes, held in position by the interspinous ligament 8, and/or other tissues and structures associated with the spine. The ability to float between the spinous processes 2,4 also permits varying degrees of rotation, as well as flexion. Implants as described in Zucherman '842 thus have the advantage that they permit a greater degree of movement when compared with primary and supplementary spinal fusion devices.

Figure 3A:
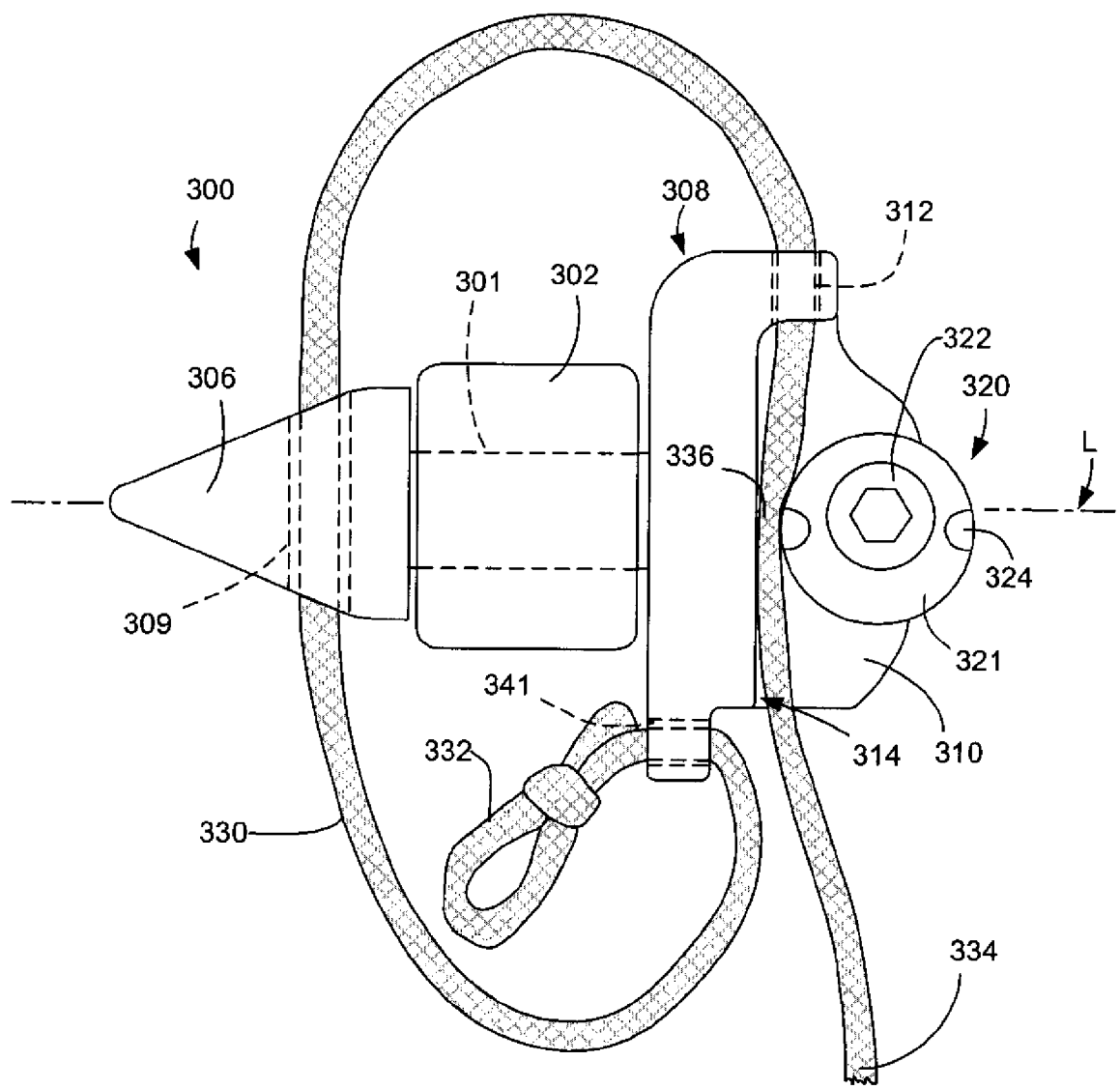
FIG. 3A is a side view of an embodiment of an implant in accordance with the present invention having a distraction guide, a spacer, a brace, and a binder associated with the brace and fixable in position by a capture device.

In some circumstances, for example where a patient develops spondylosis or other degenerative disorder that makes both flexion and extension painful and uncomfortable, it can be desired that the spinous processes be further immobilized, while providing the same ease of implantation as provided with implants described above. Referring to FIG. 3A, an embodiment of an implant 300 in accordance with the present invention is shown. The implant 300 includes a distraction guide 306, a spacer 302, and a brace 308. As shown, the spacer 302 is rotatable about a central body 301 extending from the brace 302, although in other embodiments the spacer 302 can be fixed is position. A binder 330 can be fixedly connected with the brace 308 at a proximal end 332 of the binder 330. The binder 330 is flexible, or semi-flexible, and can be positioned around adjacent spinous processes so that the binder 308 engages the spinous processes during flexion of the spine. Once positioned around adjacent spinous processes, tension of the binder 330 can be set when the binder 330 is secured to the brace 308 so that relative movement of the adjacent spinous processes during flexion is limited or prevented, as desired.

As can be seen in FIG. 3A, in an embodiment the brace 308 can include a first end having a slot 341 through which the proximal end 332 of the binder 330 can be threaded and subsequently sutured, knotted or otherwise bound so that the proximal end 332 of the binder 330 cannot be drawn through the slot 341. In other embodiments (not shown), the proximal end 332 can be looped or can include a connector, such as a clasp or other device, and can be fixed to the brace 308 via a fastener that engages the connector. One of ordinary skill in the art can appreciate the myriad different ways in which the proximal end 332 of the binder 330 can be associated with the brace 308 so that tension can be applied to the binder 330, and implants in accordance with the present invention are not intended to be limited to those schemes described in detail herein.

The brace 308 can include a height along the spine greater than a height of the spacer 302 so that movement along a longitudinal axis L in the direction of insertion is limited or blocked by the brace 308 when the brace 308 contacts the lateral surfaces of the spinous processes. In this way, the brace 308 can function similarly to the wing 108 of the above described implant 100. In other embodiments, the brace 308 can have a height greater or smaller than as shown. Once the binder 330 is positioned around the spinous processes and secured, movement of the implant 300 relative to the spinous processes is limited by the binder 330 along the longitudinal axis as well as along the spinous processes (i.e., anterior-to-posterior movement).

A free end of the binder 330 can be secured to the brace 308 by a capture device 320 associated with the brace 308. The brace 308 can include a flange 310 from which the capture device 320 can extend. In the embodiment shown in FIG. 3A, the capture device 320 comprises a rotatable cam 321 having a fastener 322 and one or more cut-outs 324. A tool can be mated with the cut-outs 324 and rotated to pivot the rotatable cam 321. When the cam 321 is rotated, the eccentric shape of the cam 321 causes a gap to close between the cam 321 and a wall 314 of the brace 330 from which the flange 310 extends. When the binder 330 is positioned between the cam 321 and the wall 314, the rotation of the cam 321 can pinch the binder 330 between the cam 321 and the wall 314, defining a secured end 336 of the binder 330.

Optionally, the fastener 322 can be screwed (i.e., rotated) so that the fastener 322 is further seated, tightening against the cam 321 to fix the cam 321 in position. Further, optionally, one or both of the wall 314 and the rotatable cam 321 can include knurls, or some other texture (e.g., teeth) to prevent slippage (i.e., the slipping of the binder 330 between the cam 321 and the wall 314). The brace 308 can further include a guide 312, such as a channel or slot (a slot as shown) at a second end of the brace 308 to align the binder 330 with the capture device 320.

The binder 330 can comprise a strap, ribbon, tether, cord, or some other flexible (or semi-flexible), and preferably threadable structure. The binder 330 can be made from a biocompatible material. In an embodiment, the binder 330 can be made from a braided polyester suture material. Braided polyester suture materials include, for example, Ethibond, Ethiflex, Mersilene, and Dacron, and are nonabsorbable, having high tensile strength, low tissue reactivity and improved handling. In other embodiments, the binder 330 can be made from stainless steel (i.e., surgical steel), which can be braided into a tether or woven into a strap, for example. In still other embodiments, the binder 330 can be made from some other material (or combination of materials) having similar properties.

The distraction guide 306 can optionally include a slot, bore, cut-out or other cavity 309 formed in the distraction guide 306 through which the binder 330 can be threaded or positioned. Such a cavity can allow on-axis positioning of the binder 330 (i.e., the binder can be substantially aligned with the longitudinal axis L of the implant 300). Further, capturing the binder 330 within a slot or bore can prevent or limit shifting of the distraction guide 306 relative to the binder 330 to further secure the implant 300 between the spinous processes.

As will be readily apparent to one of skill in the art, implants in accordance with the present invention provide significant benefits to a physician by simplifying an implantation procedure and reducing procedure time, while providing an implant that can limit or block flexion and extension of the spine. A physician can position an implant between adjacent spinous processes and can position a binder 330 connected with the brace 308 around the spinous processes without requiring the physician to measure an appropriate length of the binder 330 prior to implantation. The capture device 320 allows the binder 330 to be secured to the brace 308 anywhere along a portion of the binder 330, the portion being between a distal end 334 of the binder 330 and the proximal end 332. The physician can secure the binder 330 to the brace 308 to achieve the desired range of movement (if any) of the spinous processes during flexion.

Figure 3B:
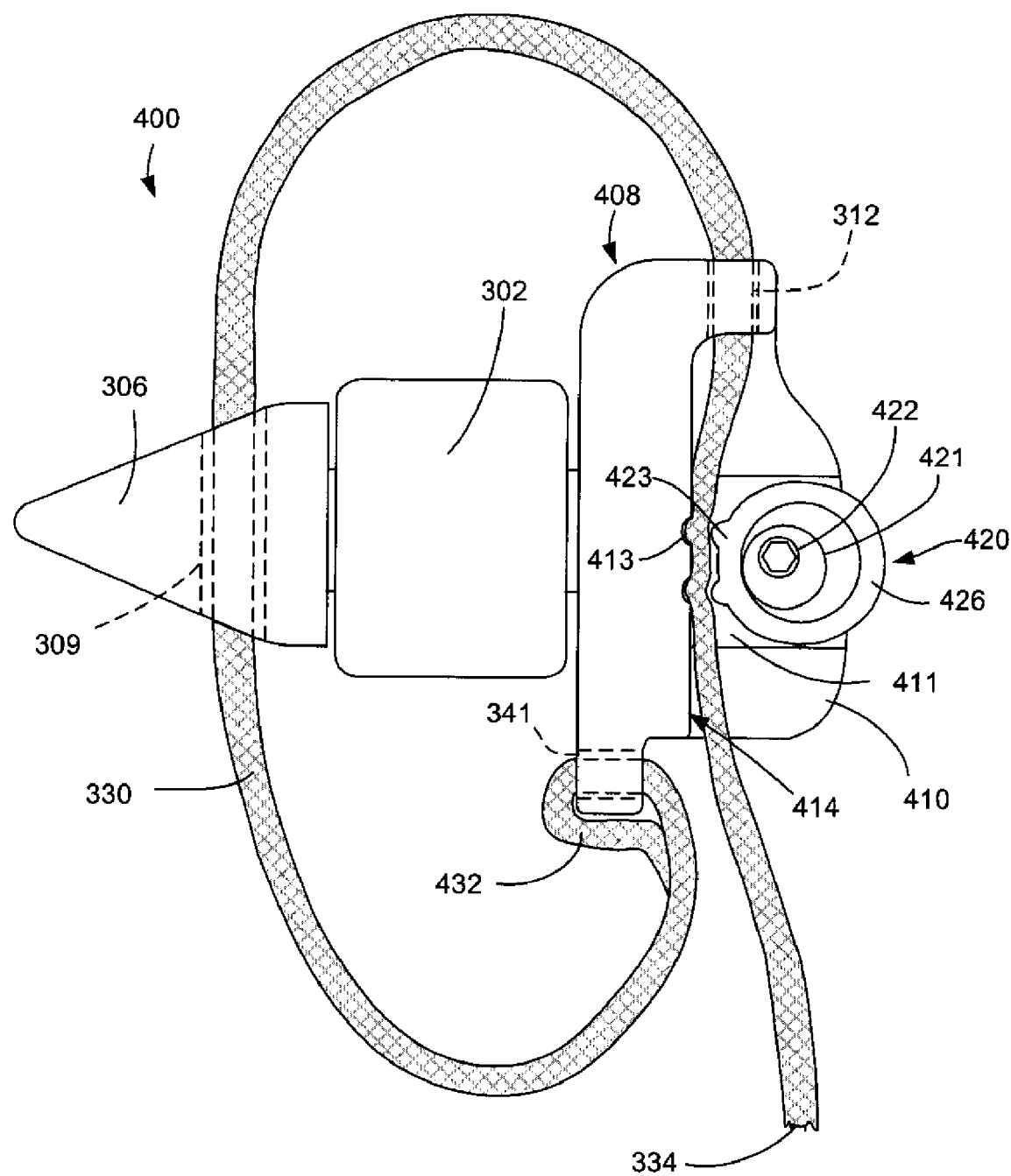
FIG. 3B is a side view of an alternative embodiment of an implant in accordance with the present invention including a brace wall having recesses for receiving lobes of a capture device.

The capture device 320 and brace 308 can have alternative designs to that shown in FIG. 3A. A side view of an implant 400 in accordance with an alternative embodiment of the present invention is shown in FIG. 3B, the implant 400 including a capture device 420 comprising a cam 421 positioned within a ring 426 having one or more lobes 423 corresponding with one or more recesses 413 in a wall 414 of the brace 408. The binder 330 is positioned between the capture device 420 and the brace 408. Once the binder 330 is positioned as desired, the fastener 422 and cam 421 can be rotated using an appropriate tool, with the cam 421 forcing the lobes 423 of the ring 426 to mate with the recesses 413 of the brace 408, preventing the ring 426 from shifting in position and defining a secure end 336 of the binder 330. Rotating the fastener 422 rotates and optionally tightens down the cam 421. Such a capture device 420 can provide a physician a visual indication that the binder 330 is properly secured to the brace 408, as well as preventing slippage.

Figure 3C:
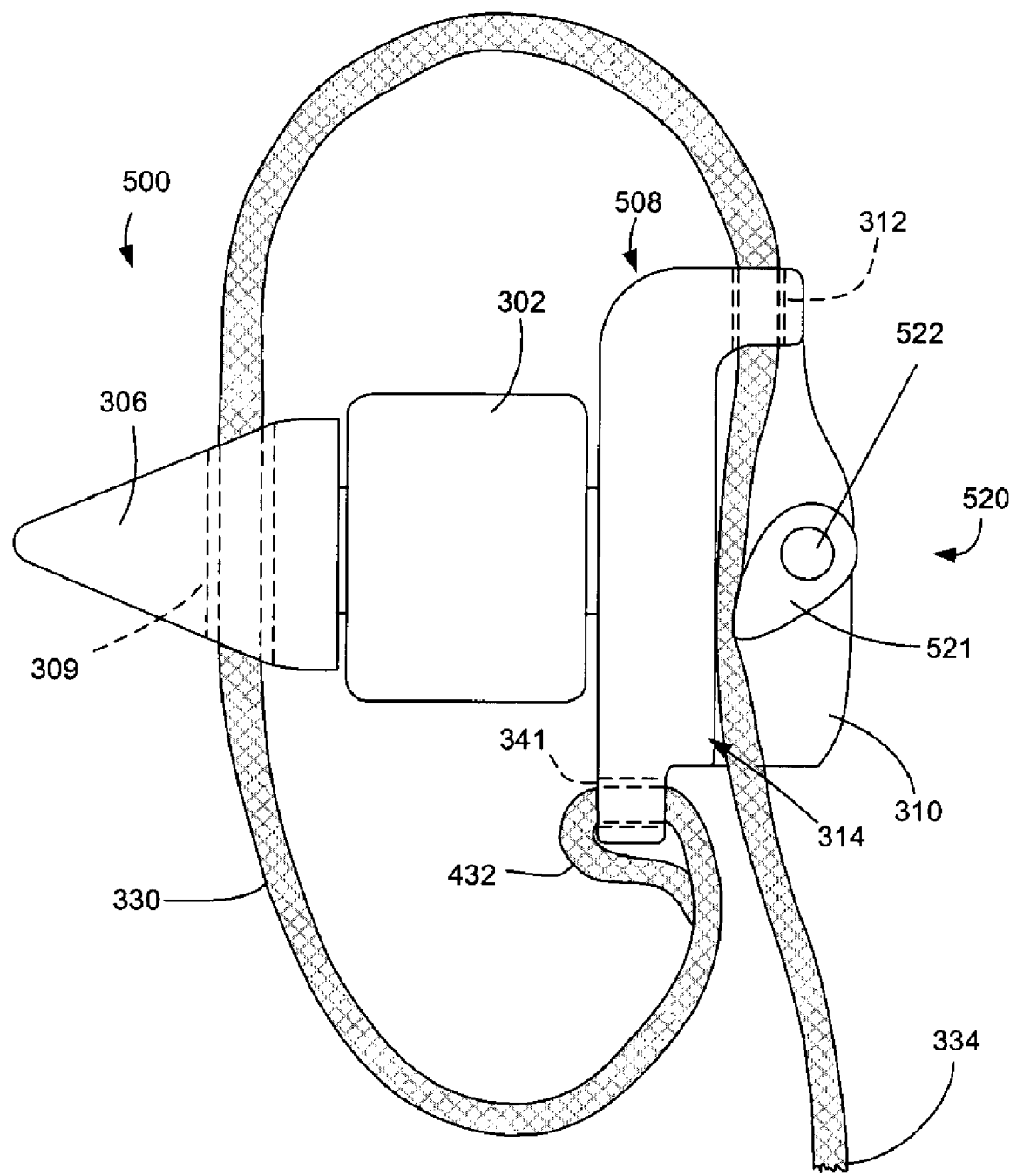
FIG. 3C is a side view of still another embodiment of an implant in accordance with the present invention including a capture device having a spring-loaded cam for securing a binder against a brace wall.
Figure 3D:
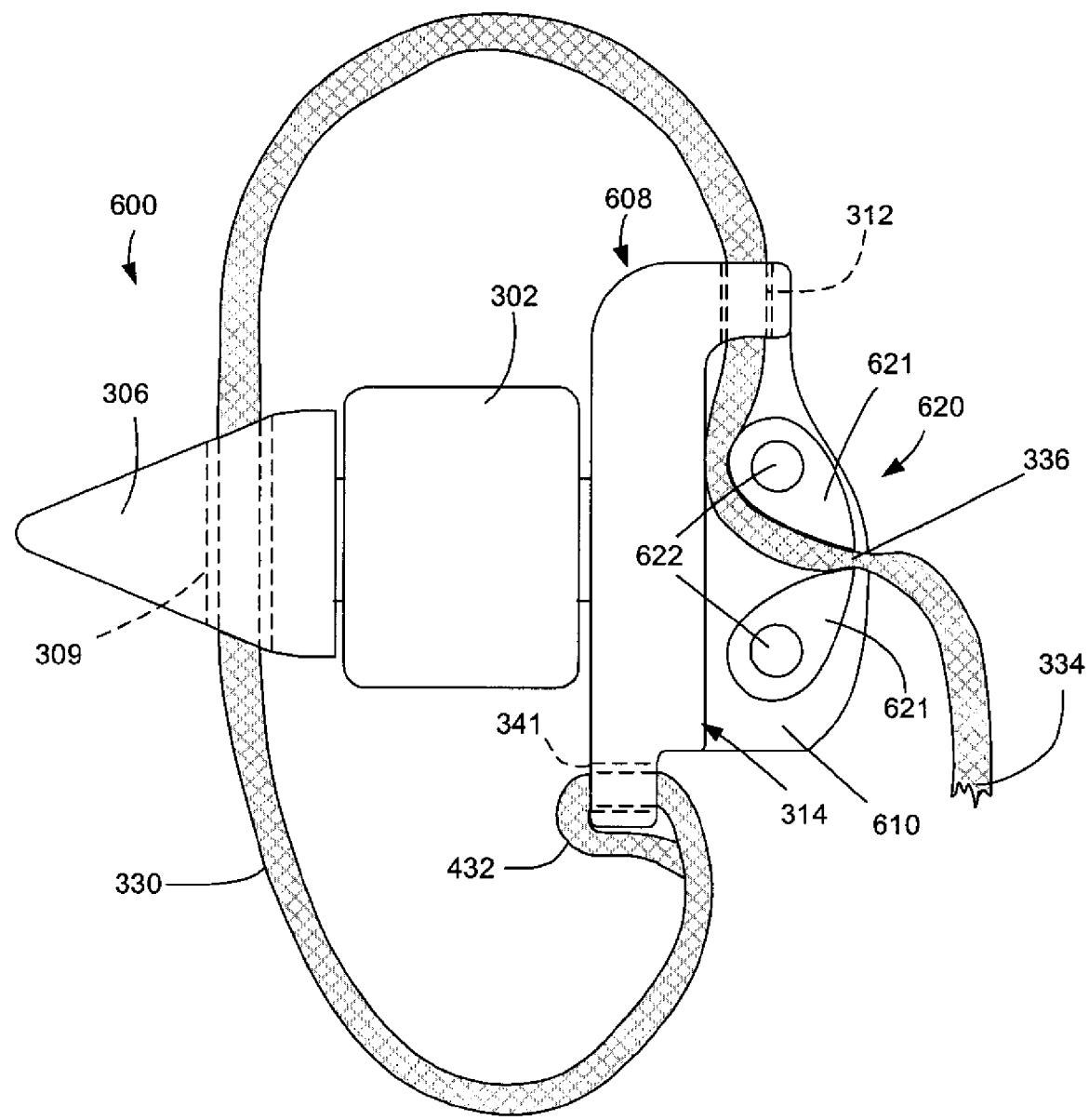
FIG. 3D is a side view of a still further embodiment of an implant in accordance with the present invention including a capture device having dual spring-loaded cams for securing a binder in position.

Referring to FIGS. 3C and 3D, in still other embodiments, the implant can include a capture device comprising a spring-loaded mechanism. FIG. 3C illustrates an implant 500 including a capture device 520 comprising a single spring-loaded cam 521 pivotally connected with the flange 310 and biased to rotate in one direction. The distance between the pivot point of the cam 510 and the wall 314 is sufficiently narrow that the rotation of the cam 521 in the direction of bias is blocked (or nearly blocked) by the wall 314. The eccentricity of the cam 521 is large enough that a maximum gap between the wall 314 and the cam 521 is sufficiently wide as to allow the binder 330 to be threaded between the cam 521 and the wall 314. A physician can position the binder 330 between the cam 521 and the wall 514 by overcoming the spring-force of the spring-loaded cam 521. Once the binder 330 is position as desired, the physician need only allow the bias force of the spring-loaded cam 520 to force the cam 521 against the wall 314, so that the cam 521 pinches and secures the binder 330 between the cam 521 and the wall 314. Optionally, one or both of the cam 521 and the wall 314 can be knurled or otherwise textured to limit or prevent slippage. Further, the wall 314 can optionally include a recess (not shown) to receive the cam 521 so that the binder 330 is pinched within the recess (similar to the lobe and recess arrangement of FIG. 3B), thereby further limiting slippage.

FIG. 3D illustrates an implant 600 including a capture device 620 comprising dual spring-loaded cams 621, the dual spring-loaded cams 621 being pivotally connected with the flange 310. The dual spring-loaded cams 621 are biased in opposition to one another so that the cams 621 abut one another, similar to cam cleats commonly used for securing rope lines on boats. During surgery, the binder 330 can be loosely positioned around the adjacent spinous processes and threaded between the cams 621. Tension can be applied to the binder 330, as desired, by drawing the binder 330 through the cams 621. The force of the binder 330 being pulled through the cams 621 can overcome the bias force to allow the binder 330 to be tightened, while releasing the binder 330 can define a secure end 336 of the binder 330 as the cams 621 swivel together. As above, one or both of the cams 621 can be knurled or otherwise textured to limit or prevent slippage.

Embodiments of implants have been described in FIGS. 3A-3D with some level of specificity; however, implants in accordance with the present invention should not be construed as being limited to such embodiments. Any number of different capture devices can be employed to fix a binder to a brace by defining a secure end of the binder, and such capture devices should not be construed as being limited to capture devices including cams, as described above. The capture device need only be a device that allows a physician to fit a binder having a generic size, or estimated size, around adjacent spinous processes with a desired level of precision in tension.

Figure 4A:
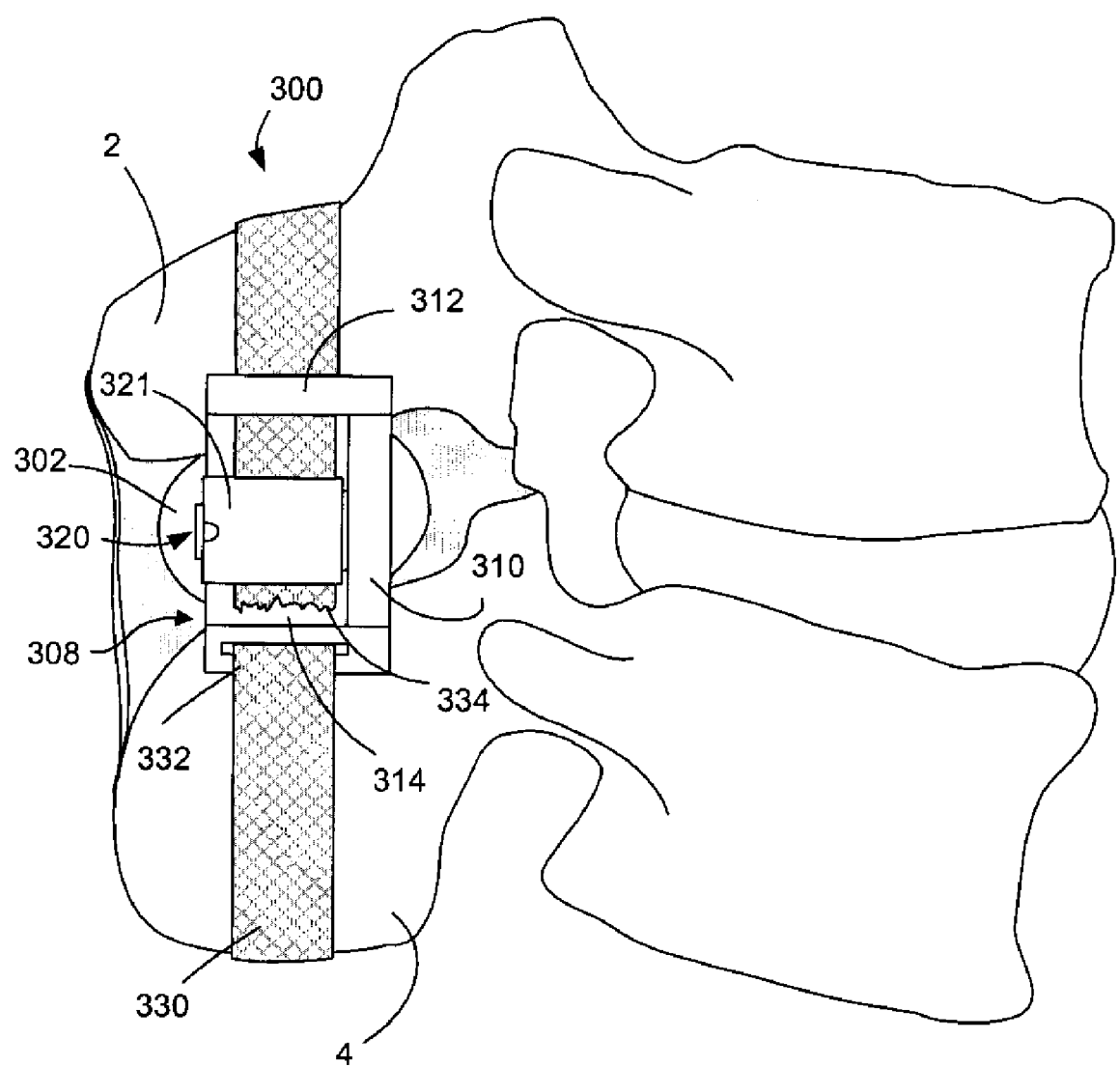
FIG. 4A is an end view of the implant of FIG. 3A positioned between adjacent spinous processes.
Figure 4B:
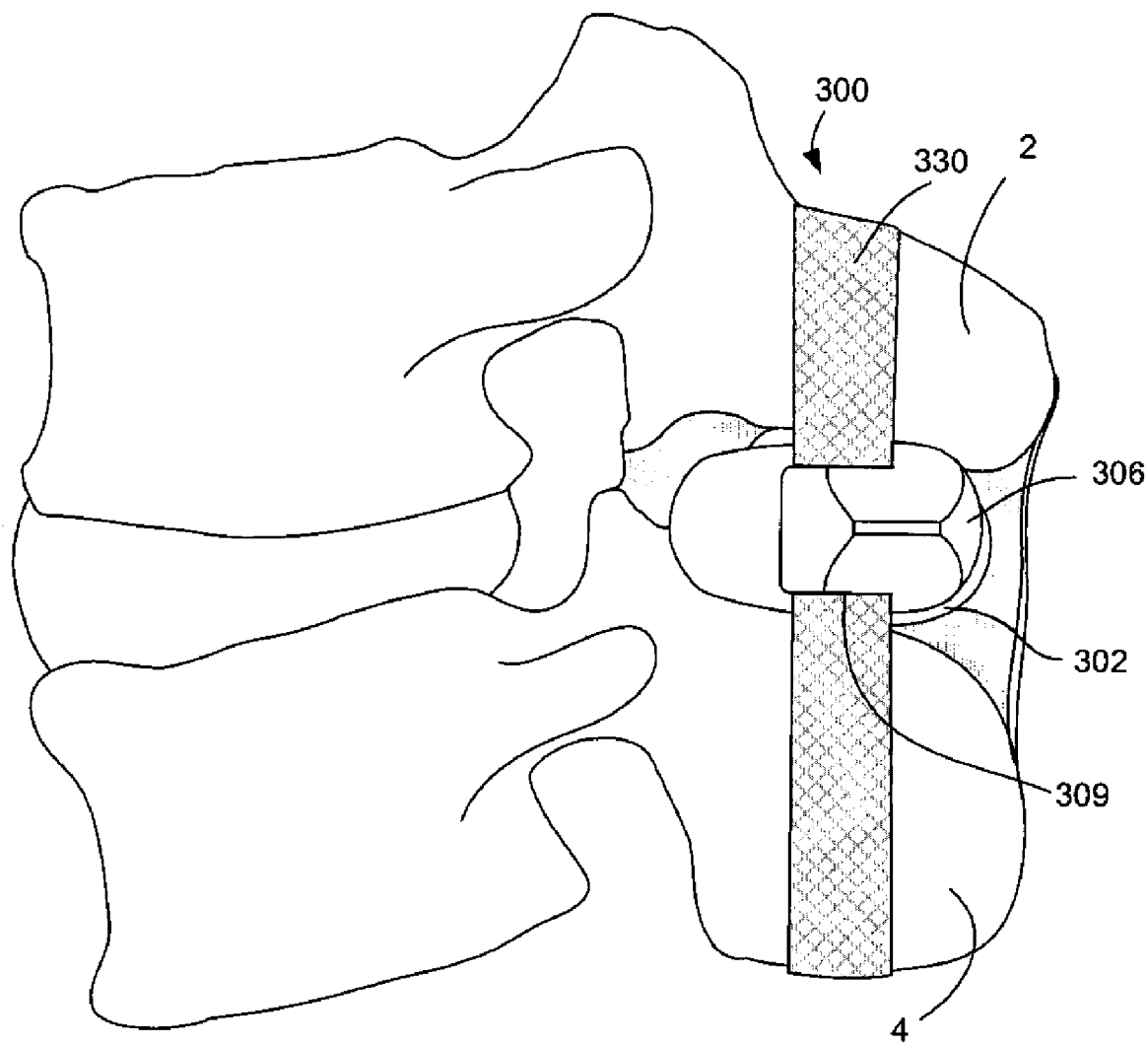
FIG. 4B is an end view of the implant of FIG. 3A positioned between adjacent spinous processes.

FIGS. 4A and 4B are an opposite end views of the implant of FIG. 3A positioned between adjacent spinous processes extending from vertebrae of the lumbar region. The contours of a space between adjacent spinous processes can vary between patients, and between motion segments. A rotatable spacer 302 can rotate to best accommodate the shape of the space so that the implant 300 can be positioned as desired along the spinous processes. For example, it can be desirable to position the spacer 302 as close to the vertebral bodies as possible (or as close to the vertebral bodies as practicable) to provide improved support. Once the implant 300 is positioned as desired, the binder 330 can be threaded through interspinous ligaments associated with motion segments (i.e., pairs of adjacent vertebrae and associated structures and tissues) above and below the targeted motion segment so that the binder 330 is arranged around the upper and lower spinous processes 2,4. The binder 330 can then be threaded through the slot 312 of the brace 308 and positioned between the capture device 320 and the brace wall 314. A first tool (not shown) can be inserted into the incision formed to insert the implant 300 between the spinous processes 2,4. Though not shown, the spacer 302 can include a notch, similar to a notch 190 of the spacer 102 of FIG. 1, and the brace 308 can include recesses, similar to recesses 103,104 of the first wing 108 of FIG. 1, that can be engaged by the first tool for grasping and releasing the implant 300 during insertion. (See U.S. Pat. No. 6,712,819, which is incorporated herein by reference.) Alternatively, some other technique for grasping and releasing the implant 300 can be employed. Once the implant 300 is positioned and the binder 330 is arranged as desired, a second tool (not shown), such as a forked tool having spaced apart tines, can engage the cam 321 of the capture device 320 to rotate the cam 321, thereby securing the binder 330 to the brace 308. A hex wrench can tighten down the fastener 322 if desired. Alternatively, a single tool can be employed to perform both the function of insertion of the implant 300 and rotation of the cam 321, as depicted in the above referenced patent. Optionally, the binder 330 can then be trimmed so that the distal end 334 of the binder 330 does not extend undesirably away from the brace 308. As can be seen, the spacer 302 is rotated relative to the distraction guide 306 and the brace 308. Because the spacer 302 can rotate relative to the distraction guide 306 and the brace 308, the brace 308 can be positioned so that the binder 330 can be arranged around the upper and lower spinous processes 2,4 without twisting the binder 330. The binder 330 is positioned around the lower spinous process 4, threaded or positioned at least partially within a slot 309 of the distraction guide 306, and positioned around the upper spinous process 2 so that the binder 330 can be secured to the brace 308, as described above.

Figure 4C:
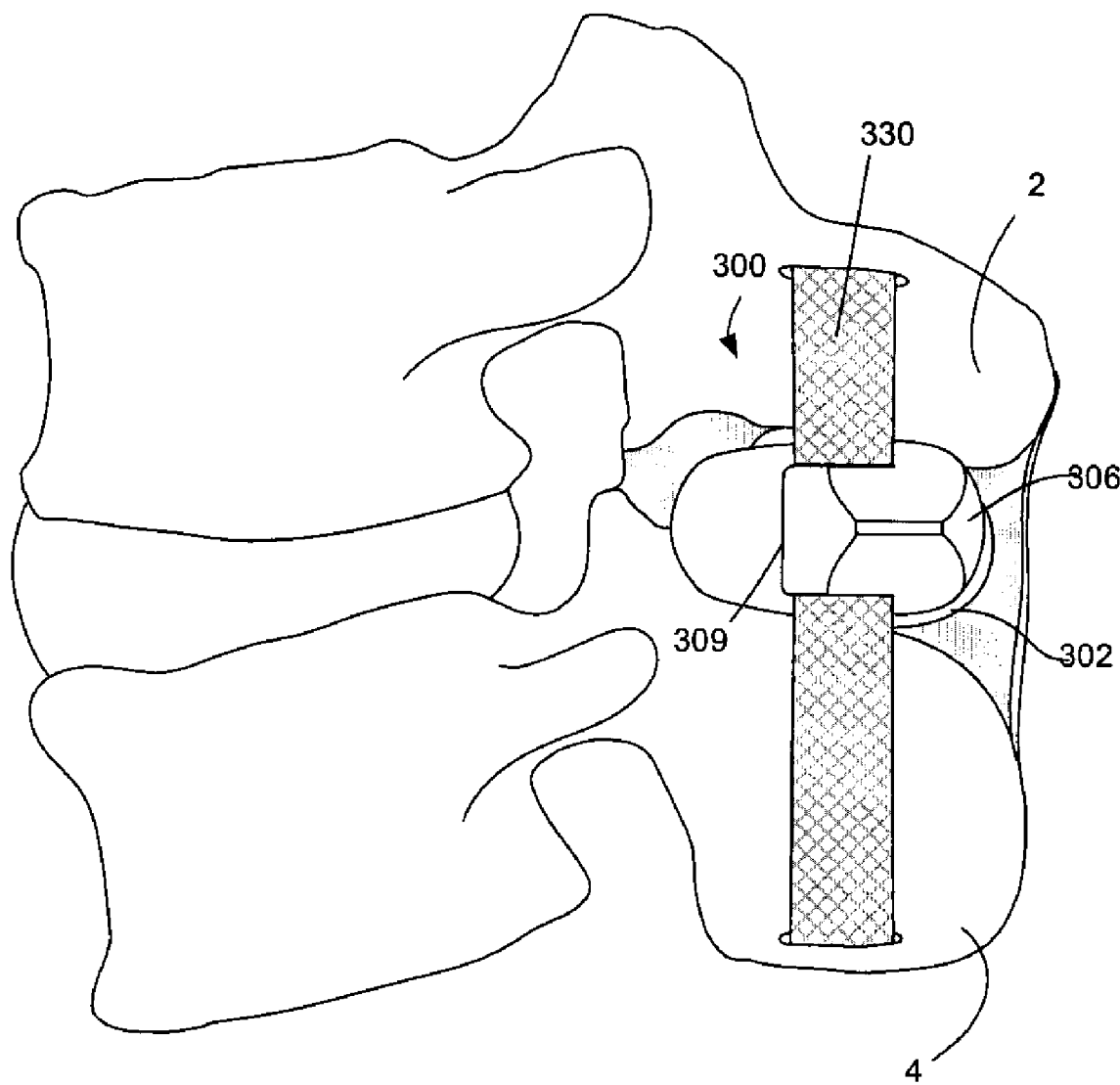
FIG. 4C is an end view of the implant of FIG. 3A positioned between adjacent spinous processes wherein the spinous processes are surgically modified to receive a binder.

Implants in accordance with the present invention can enable a physician to limit or block flexion and extension in a targeted motion segment while minifying invasiveness of an implantation procedure (relative to implantation procedures of the prior art). However, such implants can also be used where more extensive implantation procedures are desired. For example, as shown in FIG. 4C, it can be desired that the adjacent spinous processes 2,4 be surgically modified to receive the binder 330, thereby insuring that the binder 330 does not shift or slide relative to the spinous processes 2,4. The binder 330 is threaded directly through the respective spinous processes 2,4 rather than through the interspinous ligaments of adjacent motion segments. The amount of bone removed from the spinous processes 2,4 can be reduced where a cord or tether is used as a binder 330 rather than a strap. While such applications fall within the contemplated scope of implants and methods of implantation of the present invention, such application may not realize the full benefit that can be achieved using such implants due to the modification of the bone.

Figure 5:
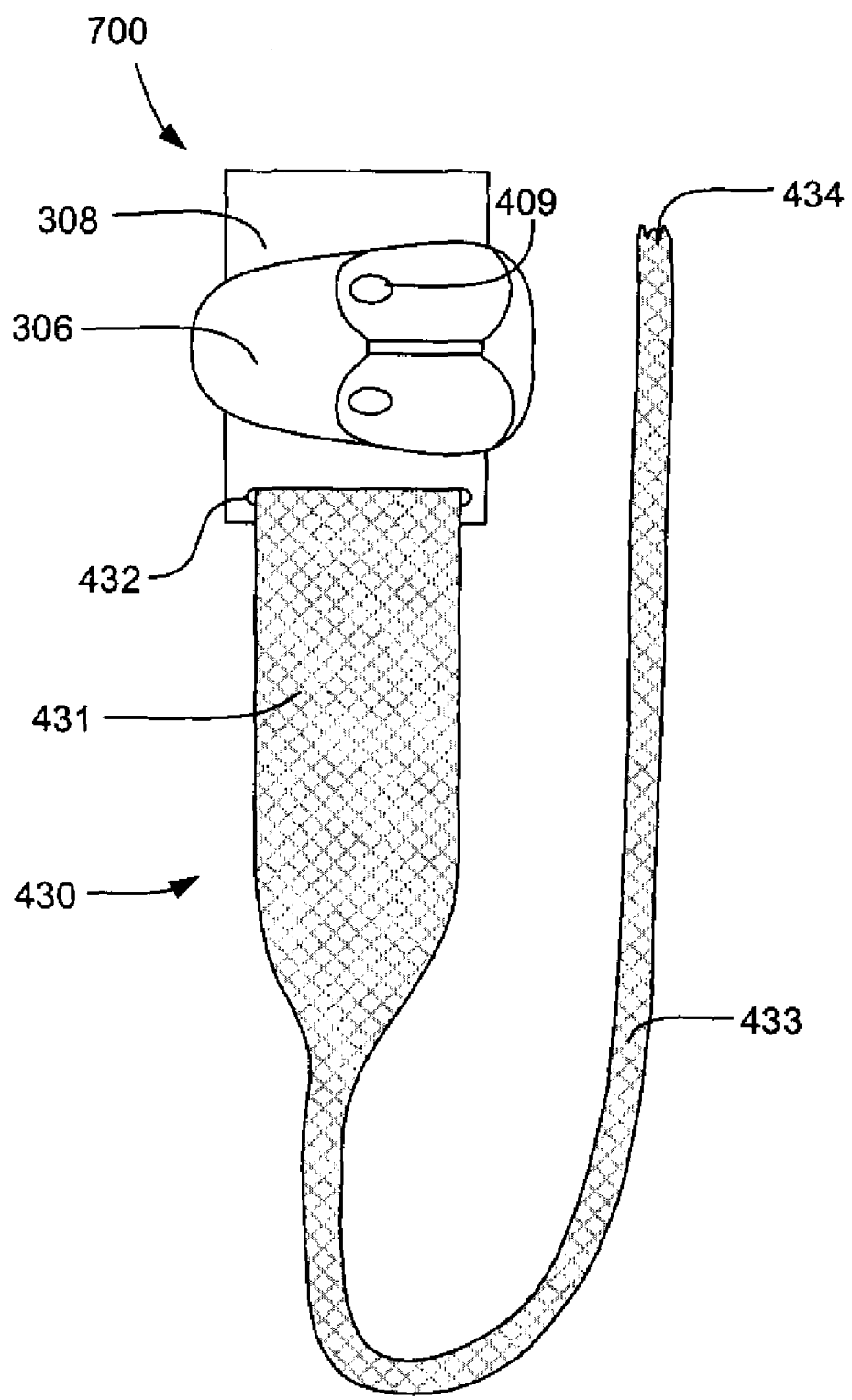
FIG. 5 is an end view of an alternative embodiment of an implant in accordance with the present invention having a binder that varies in shape along the binder's length.
Figure 6A:
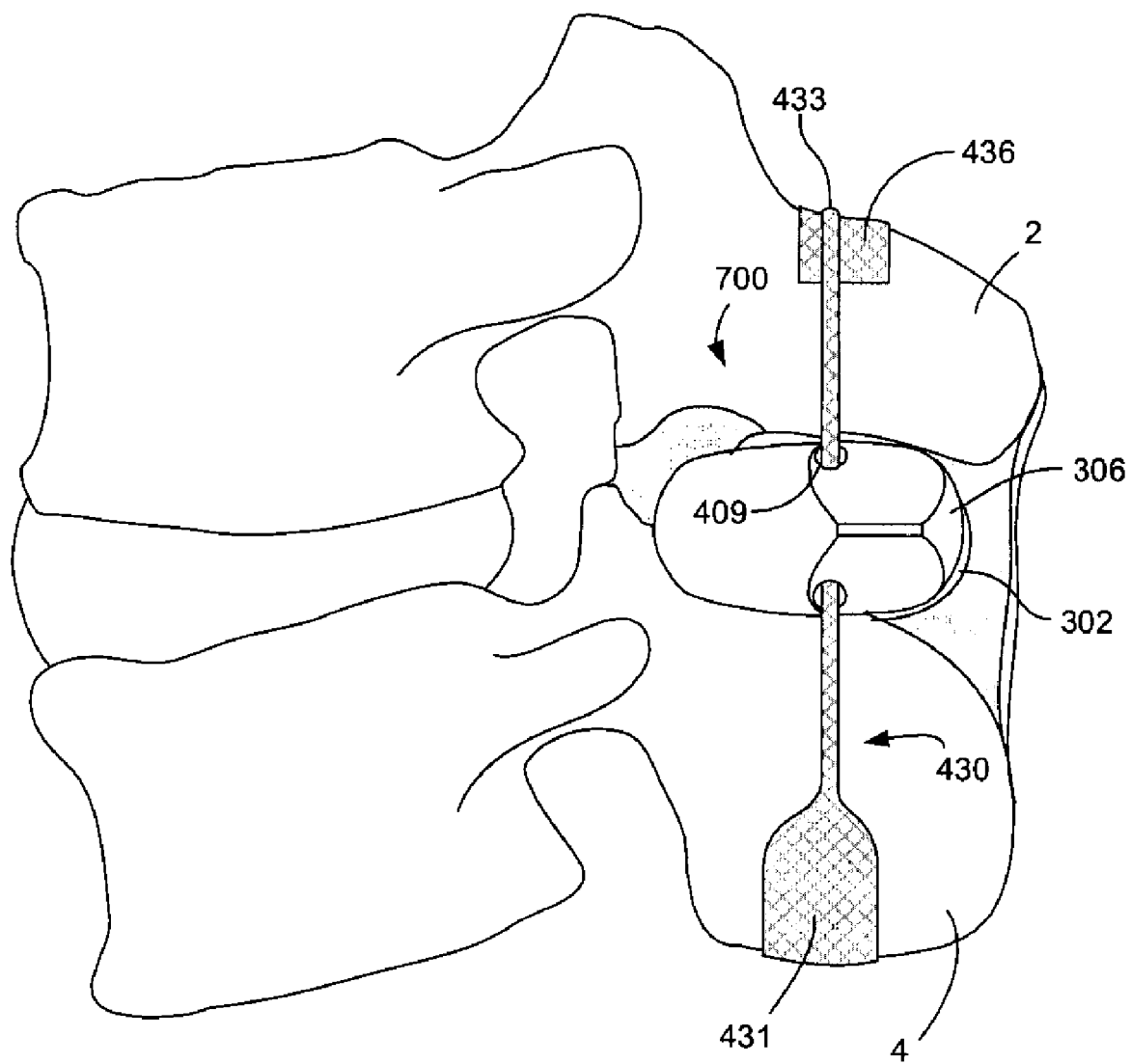
FIG. 6A is an end view of the implant of FIG. 5 positioned between adjacent spinous processes.
Figure 6B:
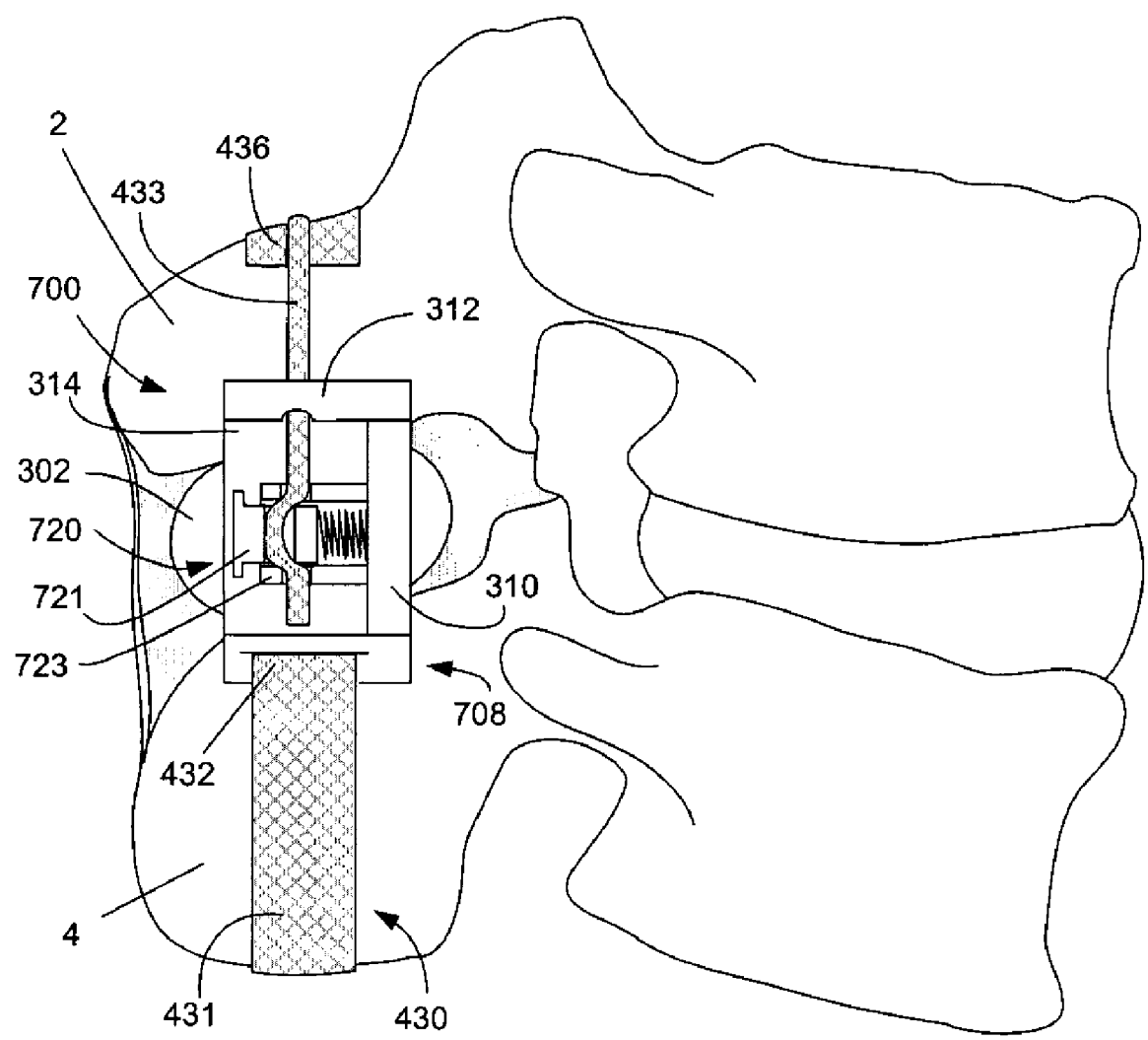
FIG. 6B is an opposite end view of the implant of FIG. 6A.

Still another embodiment of an implant 700 in accordance with the present invention is shown in the end view of FIG. 5. In such an embodiment the binder 430 can comprise a first portion 431 formed as a strap for arrangement around one of the upper and lower spinous processes 2,4, and that tapers to a second portion 433 formed as a cord. The distraction guide 406 can include a bore 409 or other cavity for receiving the second portion 433. As can be seen in FIG. 6A, once the binder 430 is threaded through the distraction guide 406, a pad 436 of biocompatible material can be associated with the binder 430, for example by slidably threading the binder 430 through a portion of the pad 436, and the pad 436 can be arranged between the binder 430 and the respective spinous process 2 so that a load applied by the binder 430 is distributed across a portion of the surface of the spinous process 2. Referring to FIG. 6B, once the binder 430 is arranged as desired relative to the adjacent spinous processes 2,4, the binder 330 can be secured by the brace 708. The brace 708 as shown is still another embodiment of a brace for use with implants of the present invention. In such an embodiment, the brace 708 includes a capture device 720 comprising a clip including a spring-loaded button 721 having a first hole therethrough and a shell 723 in which the button 721 is disposed, the shell 723 having a second hole. A physician depresses the button 721 so that the first and second holes align. The binder 430 can then be threaded through the holes, and the button 721 can be released so that the spring forces the holes to misalign, pinching the binder 430 and defining a secure end of the binder 430.

Figure 6C:
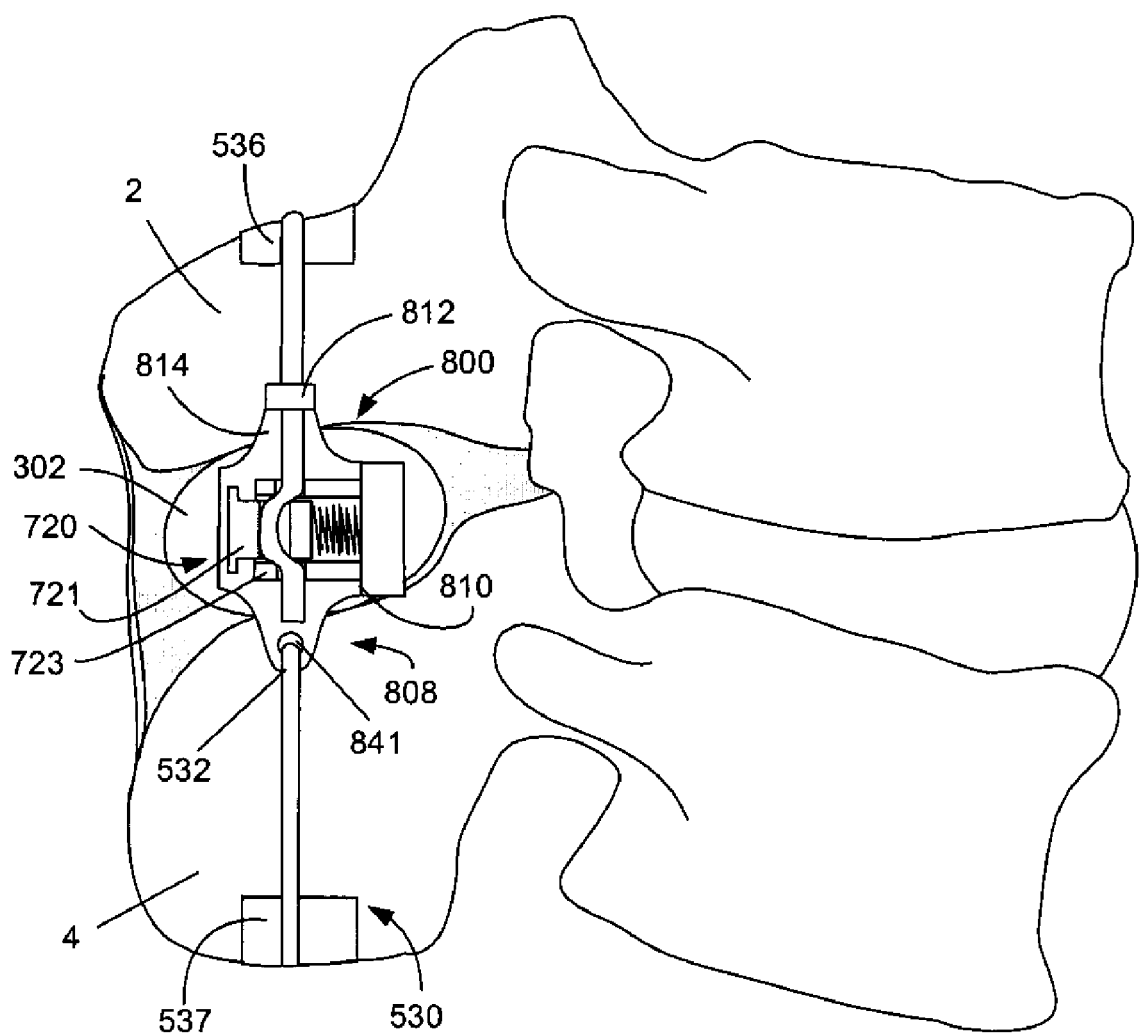
FIG. 6C is an end view of still another embodiment of an implant in accordance with the present invention having a cord for a binder.

FIG. 6C is an end view of a still further embodiment of an implant 800 in accordance with the present invention. In such an embodiment the binder 530 can comprise a cord. An upper pad 536 and a lower pad 538 can be slidably associated with the binder 530 and arranged so that a load applied by the binder 530 is distributed across a portion of the upper and lower spinous processes 2,4. As can be seen, such an embodiment can include a brace 808 having a substantially different shape than braces previously described. It should be noted that the brace 808 of FIG. 6C is shown, in part, to impress upon one of ordinary skill in the art that a brace and capture device for use with implants of the present invention can include myriad different shapes, mechanisms and arrangements, and that the present invention is meant to include all such variations. As shown, the footprint of the brace 808 is reduced by shaping the wall 814 of the brace 808 to taper at an upper end to form a guide 812 for aligning the binder 530 and to taper at a lower end to an eyelet 841 for capturing a proximal end 532 of the binder 530. The brace 808 includes a height from eyelet 841 to guide 812 such that movement of the implant 800 in the direction of insertion is blocked or limited by the brace 808.

Use of a binder to limit or prevent flexion can provide an additional benefit of limiting movement along the longitudinal axis L (shown in FIG. 3A). However, implants in accordance with the present invention can optionally further include a second wing for limiting or blocking movement in the direction opposite insertion. Inclusion of such a structure can ensure that the implant remains in position, for example where the binder slips out of a slot of the distraction guide, or where the binder becomes unsecured.

Figure 7A:
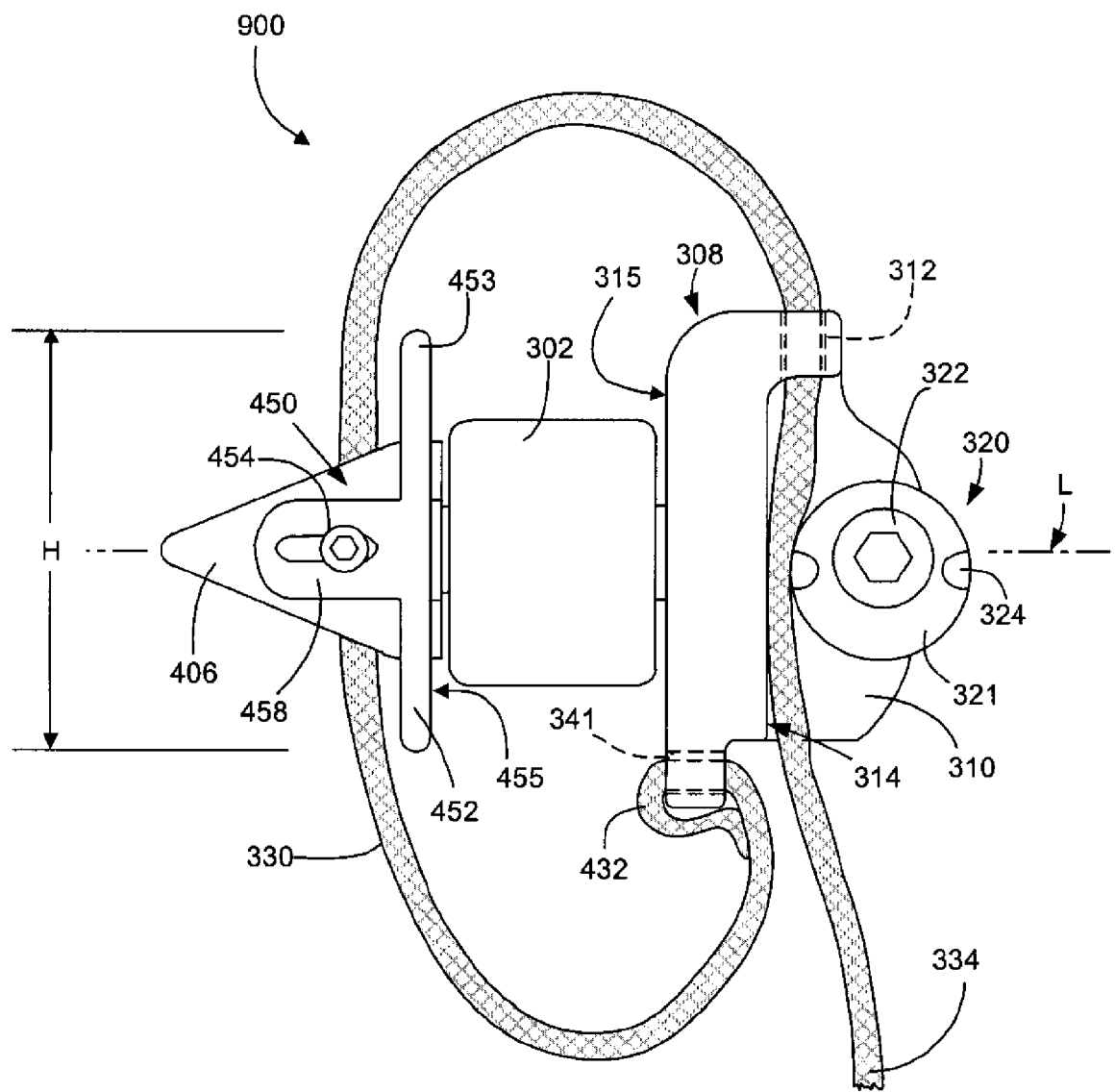
FIG. 7A is a side view of an embodiment of an implant in accordance with the present invention including a wing associated with the distraction guide to further limit or block movement of the implant.

Referring to FIG. 7A, an implant in accordance with an embodiment can include a second wing 450 connected with the distraction guide 406 of the implant 900 by a fastener 454. The second wing 450 is similar to the second wing 150 described above in reference to FIG. 1. The second wing 450 can include an alignment tab 458 allowing a position of the second wing 450 to be adjusted along a longitudinal axis L of the implant 900, and a fastener 454 (for example a hex headed bolt) for affixing the second wing 450 to the implant 900 in the position along the longitudinal axis L desired. The distraction guide 406 can include an alignment groove (not shown) corresponding to the alignment tab 458. The alignment tab 458 fits within, and is movable along, the alignment groove so that a contact surface 455 of the second wing 450 can be arranged as desired. As shown, the second wing 450 includes a substantially planar contact surface arranged so that the contact surface 455 of the second wing 450 is perpendicular to the longitudinal axis L. However, in other embodiments, the contact surface 455 need not be planar, and can be shaped and oriented to roughly correspond with a contact surface of the upper and lower spinous processes. Likewise, a contact surface 315 of the binder 308 can be shaped and oriented to roughly correspond with a contact surface of the upper and lower spinous processes. As shown, the upper portion 453 and the lower portion 452 of the second wing 450 do not extend from the distraction guide 406 as substantially as the upper portion 153 and lower portion 152 of the second wing 150 of FIG. 1. As such, the second wing 450 includes a height H along the spine smaller than that of the second wing 150 of FIG. 1. It has been observed that benefits can be gained by including a wing 450, though the wing 450 does not extend from the distraction guide 406 as significantly as shown in FIG. 1 (i.e., the wing 450 includes "nubs" extending above and/or below the height of the spacer 302). Such wings 450 will also be referred to herein as winglets. Including a second wing 450 having an overall height along the spine smaller than that of FIG. 1 can limit movement along the longitudinal axis without interfering with (or being interfered by) the arrangement of the binder 330.

Figure 7B:
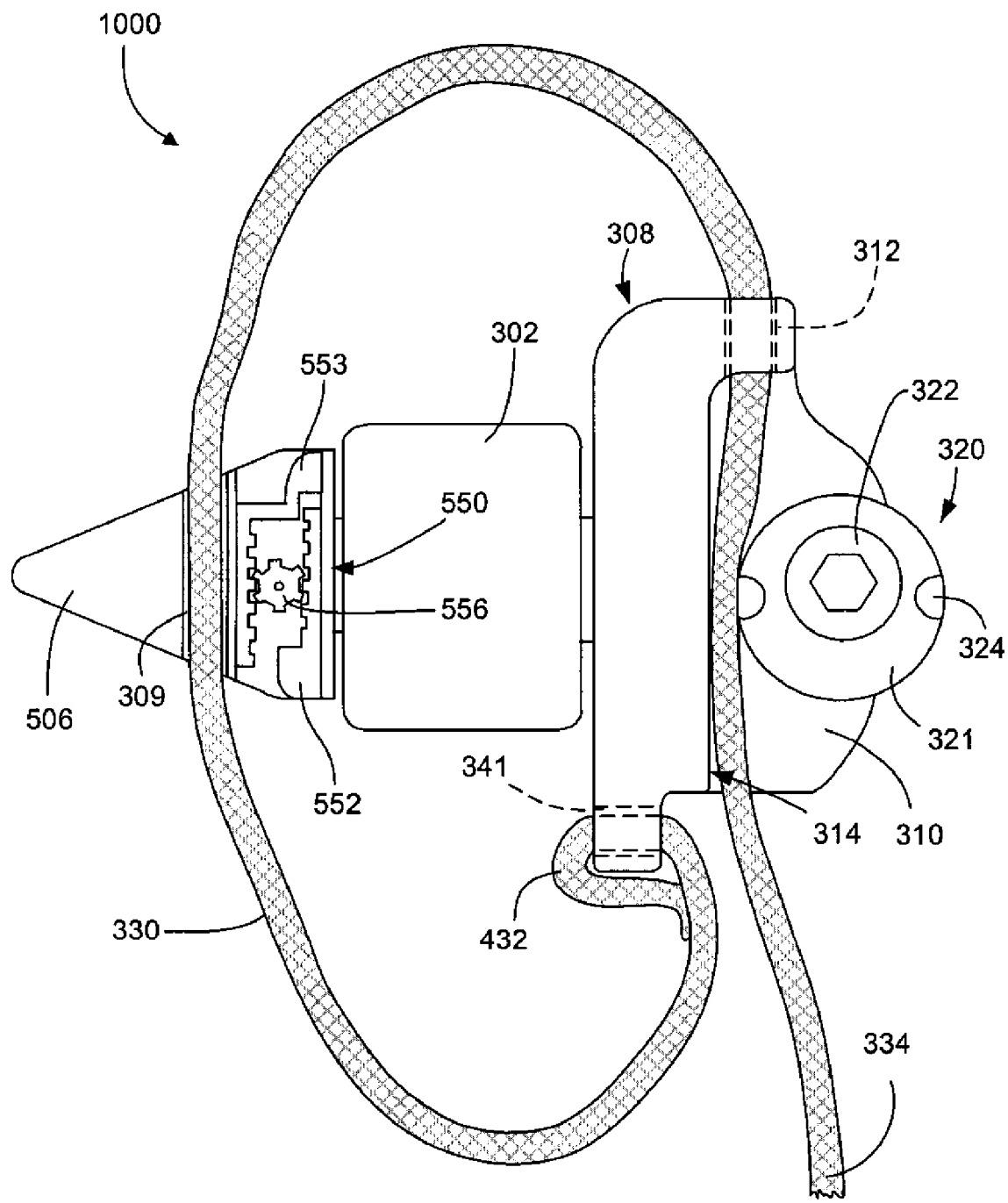
FIG. 7B is a partial cross-sectional side view of an alternative embodiment of an implant in accordance with the present invention include an extendable wing associated with the distraction guide, the extendable wing being in a retracted position.
Figure 7C:
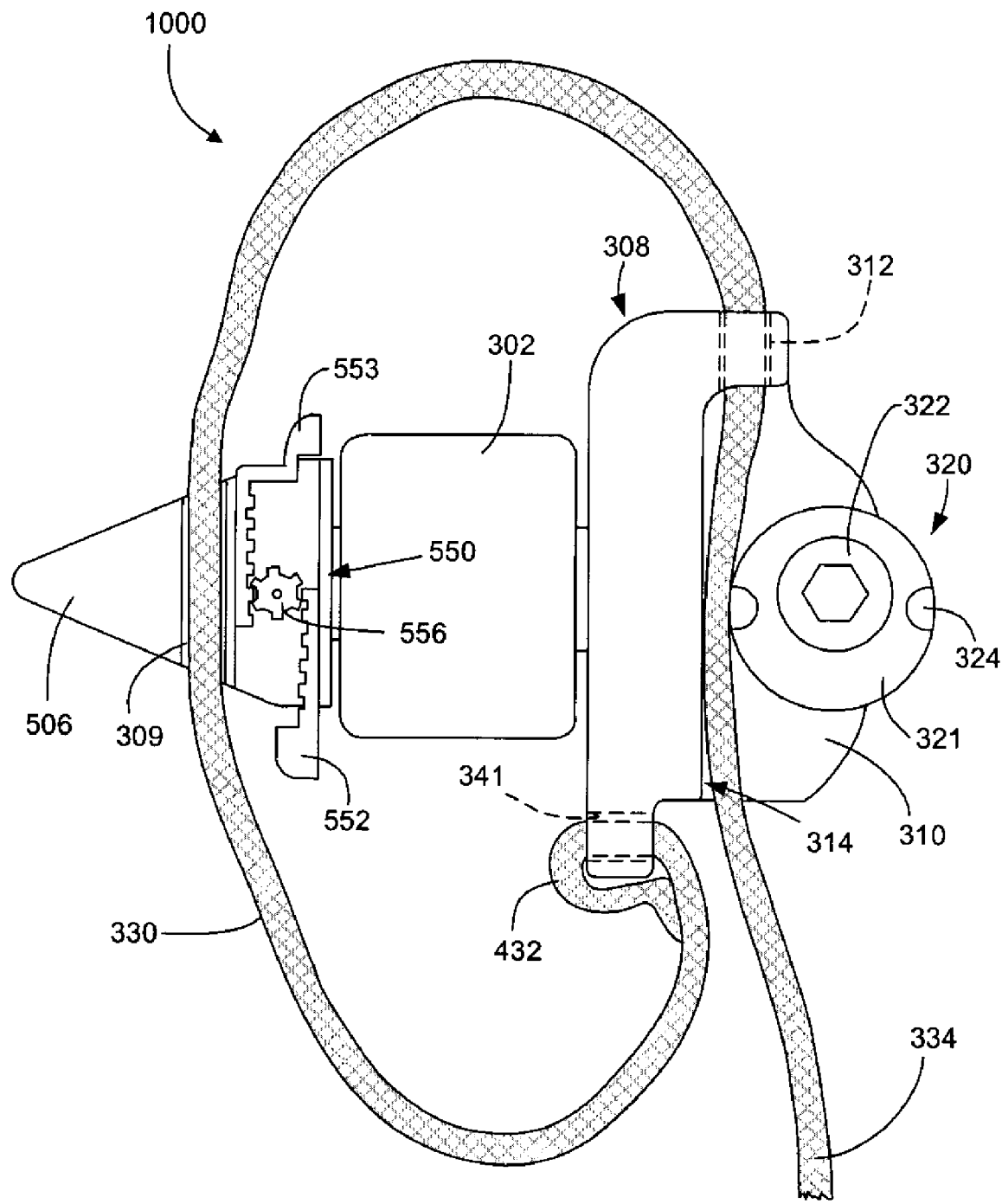
FIG. 7C is a partial cross-sectional side view of the implant of FIG. 7B wherein the extendable wing is in an extended position.

In other embodiments, implants in accordance with the present invention can include a second wing (or an upper portion and/or lower portion) extendable from the distraction guide. In this way an implant and a device for limiting or blocking movement along a longitudinal axis of the implant can be included in a single piece, possibly simplifying implantation. Referring to FIGS. 7B and 7C, implants 1000 in accordance with the present invention can include a distraction guide 506 having a selectably extendable upper portion 553 and lower portion 552 disposed within a cavity of the distraction guide 506. The upper and lower portions 553,552 can be extended by actuating a nut, knob or other mechanism operably associated with a gear 556 so that the gear 556 rotates. The teeth of the gear 556 engage teeth of the upper and lower portions 553,552, causing the upper and lower portions 553,552 to extend sufficiently that the upper and lower portions 553,552 form winglets for preventing motion of the implant 1000 in a direction opposite insertion (shown in FIG. 7C). Rotating the gear 556 in an opposite direction can retract the upper and lower portions 553,552.

Figure 7D:
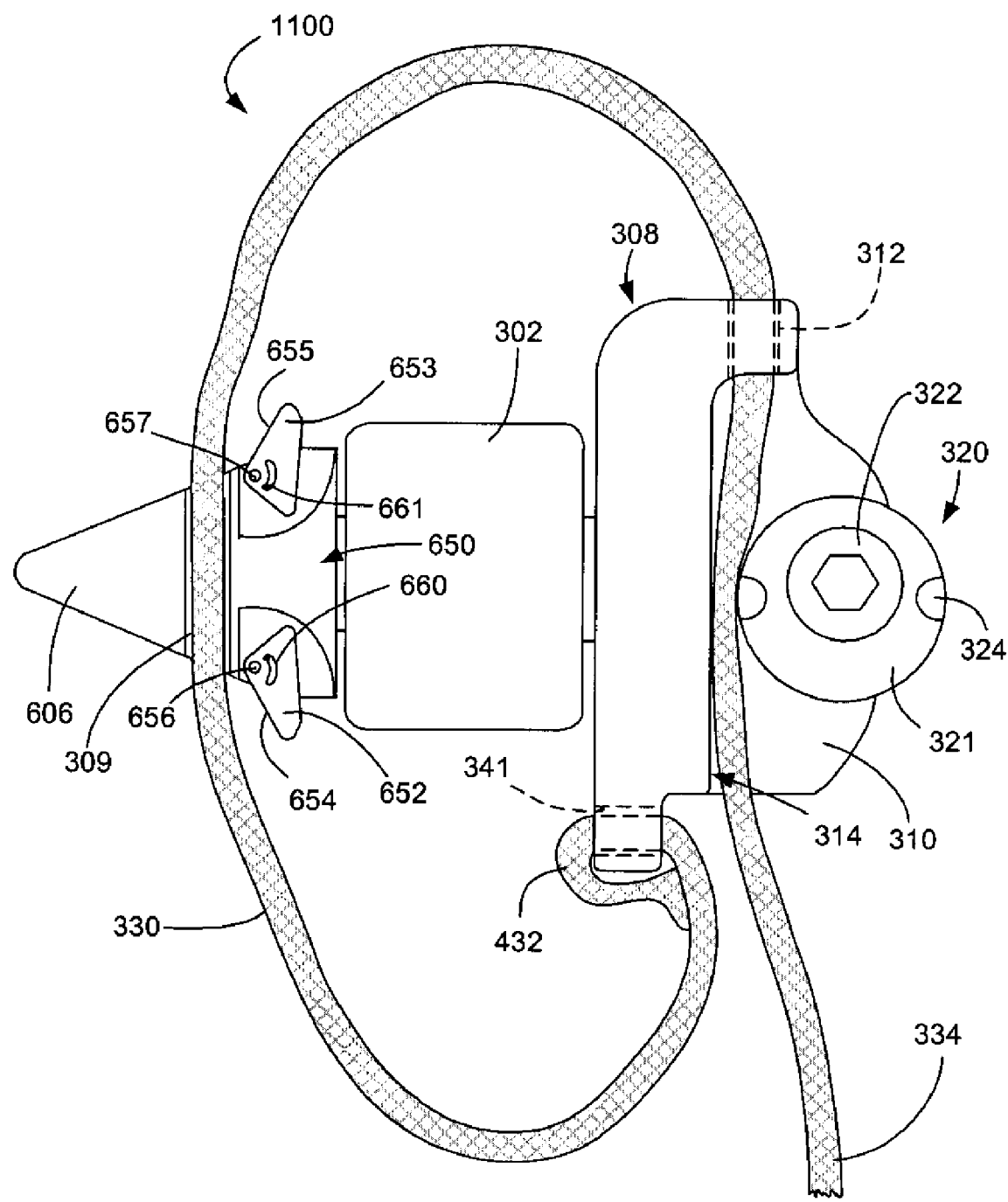
FIG. 7D is a partial cross-sectional side view of still another embodiment of an implant in accordance with the present invention including a spring-loaded wing associated with the distraction guide, the wing being in an extended position.
Figure 7E:
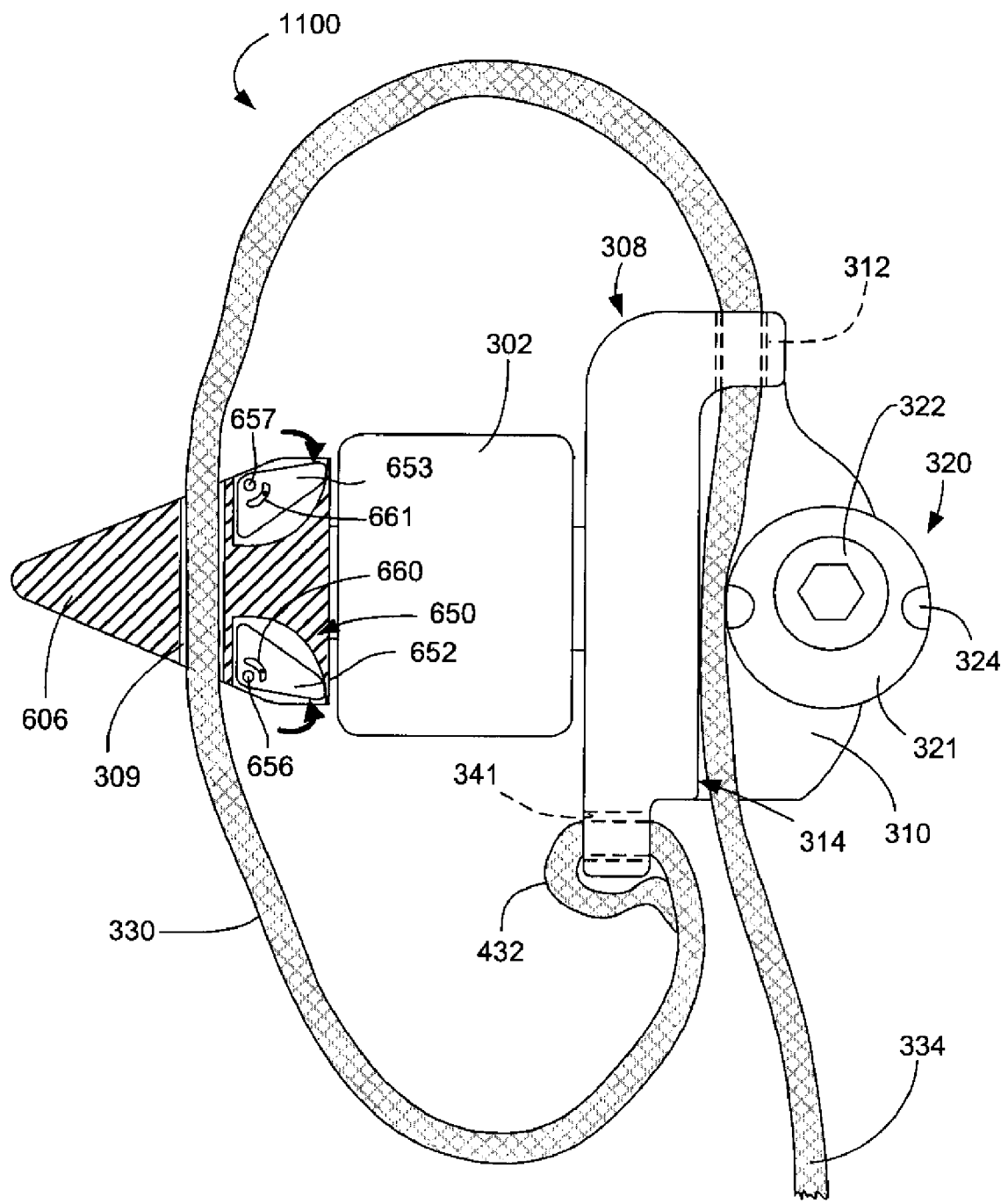
FIG. 7E is a partial cross-sectional side view of the implant of FIG. 7D wherein the spring-loaded wing is in a collapsed position.

In an alternative embodiment, implants 1100 in accordance with the present invention can include spring-loaded upper and/or lower portions 653,652 such as shown in FIGS. 7D and 7E. In such an embodiment the upper and lower portions 653,652 can be fin-shaped, having sloping forward surfaces 655,654 and being spring-biased to an extended position, as shown in FIG. 7D. As the implant 1100 is positioned between adjacent spinous processes, the spinous processes and/or related tissues can contact the forward surface 655,654 of the upper and lower portions 653,652, causing the upper and lower portions 653,652 to pivot about respective hinge points 657,656 and collapse into cavities disposed within the distraction guide 606, as shown in FIG. 7E. Once the implant 1100 clears the obstruction, the upper and lower portions 653,652 re-extend out of the distraction guide 650. A slot and pin mechanism 660,661 or other mechanism can lock the upper and lower portion 653,652 in place once extended, disallowing over-extension of the upper and lower portion 653,652 in the direction of bias. The extended upper and lower portions 653,652 limit or block movement of the implant 1100 in an a direction opposite insertion.

In still further embodiments, implants in accordance with the present invention can optionally employ some other additional mechanism for limiting or blocking motion along the longitudinal axis of the implant. Mechanisms shown and described in FIGS. 7A-7E are merely provided as examples of possible mechanisms for use with such implants, and are not intended to be limiting.

Figure 8:
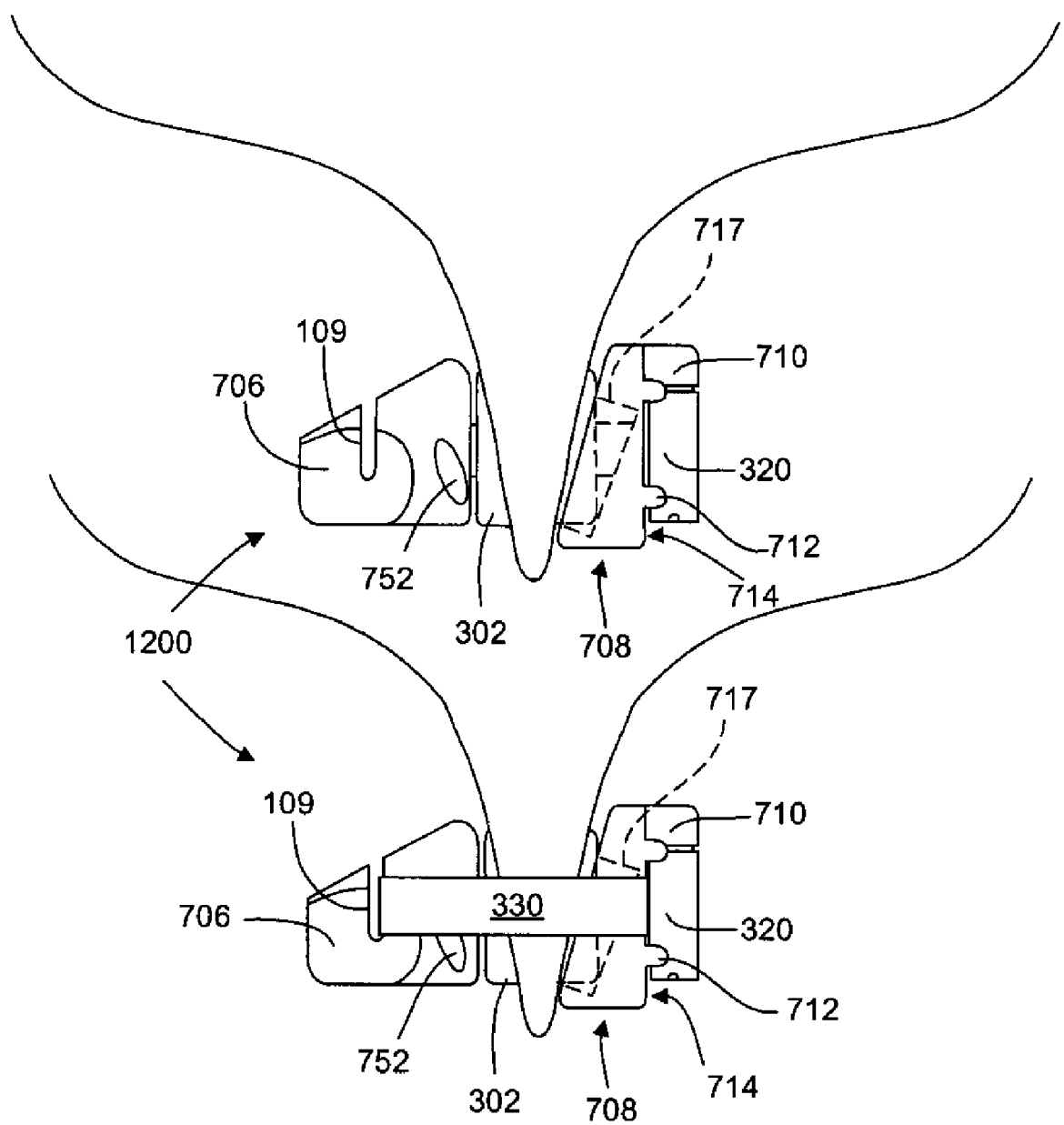
FIG. 8 is a top view of two implants in accordance with an embodiment of the present invention positioned between the spinous processes of adjacent vertebrae, one of the implants having a binder arranged around the adjacent spinous processes.

FIG. 8 is a top-down view of still another embodiment of an implant in accordance with the present invention including a brace 708 arranged at an angle along the spinous process relative to the longitudinal axis L of the implant 1200. The brace 708 is arranged at such an angle to roughly correspond to a general shape of the adjacent spinous processes. Such a general shape can commonly be found in spinous processes extending from vertebrae of the cervical and thoracic region, for example. The implant 1200 further includes a second wing 752 extending from distraction guide 706 at an angle roughly corresponding to a general shape of the adjacent spinous processes. Identical implants 1200, one above the other, are shown. The lower implant 1200 includes a binder 330 arranged around the adjacent spinous processes (only the upper spinous process is shown) and positioned in a slot 309 of the distraction guide 706. The binder 330 includes a capture device 320 for securing the binder 330 to the brace 708, and a channel formed by guides 712 on the brace 708 for aligning the binder 330 with the capture device 320. Unlike previously illustrated embodiments, the brace wall includes a recess 717 to accommodate rotation of the rotatable spacer 302. Alternatively, the implants can include fixed spacers, for example integrally formed with the brace 708 and the distraction guide 706.

Figure 9A:
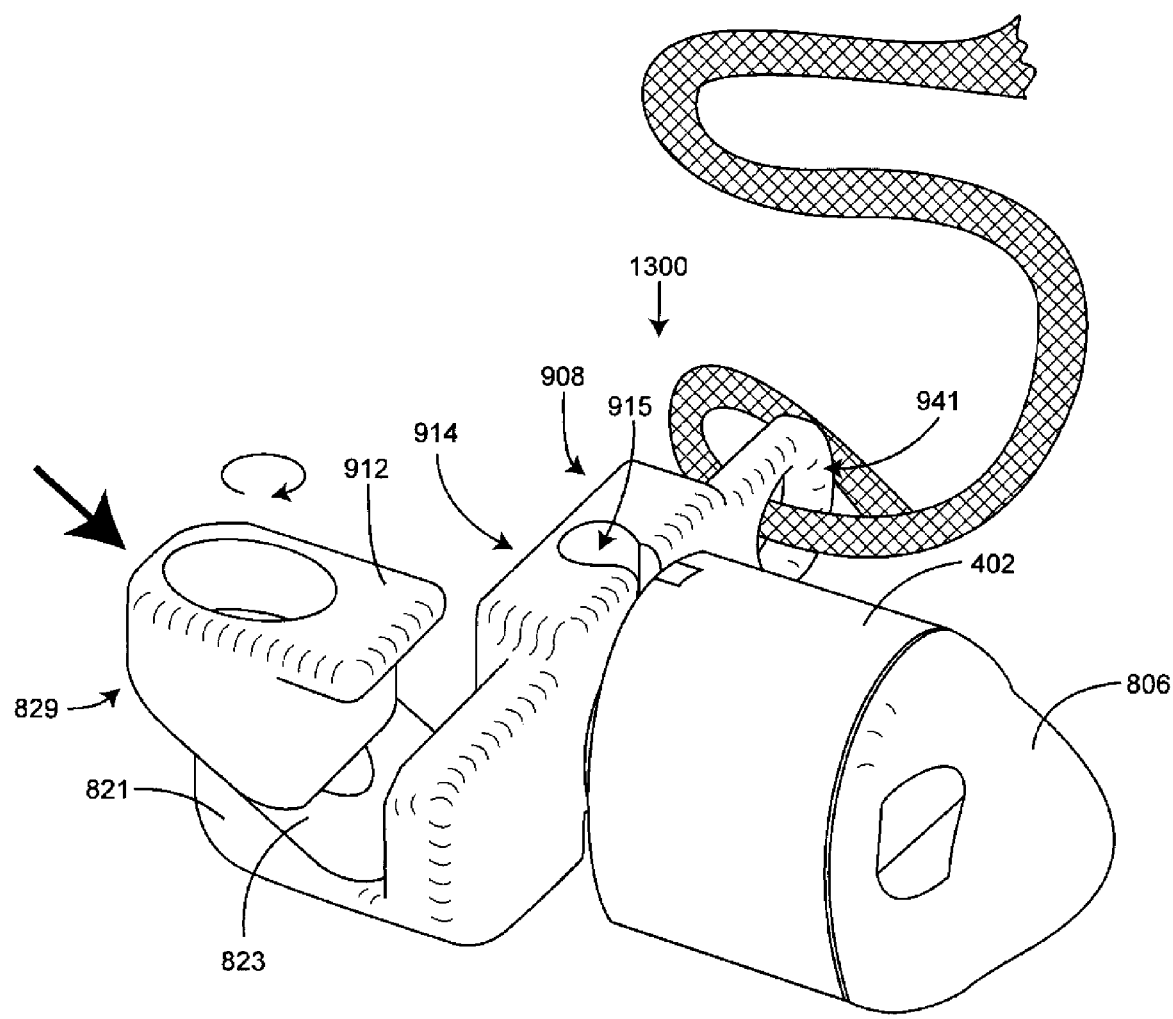
FIG. 9A is a perspective view of a further embodiment of an implant in accordance with the present invention having a distraction guide, a spacer, a brace, and a binder associated with the brace and fixable in position by a capture device.
Figure 9B:
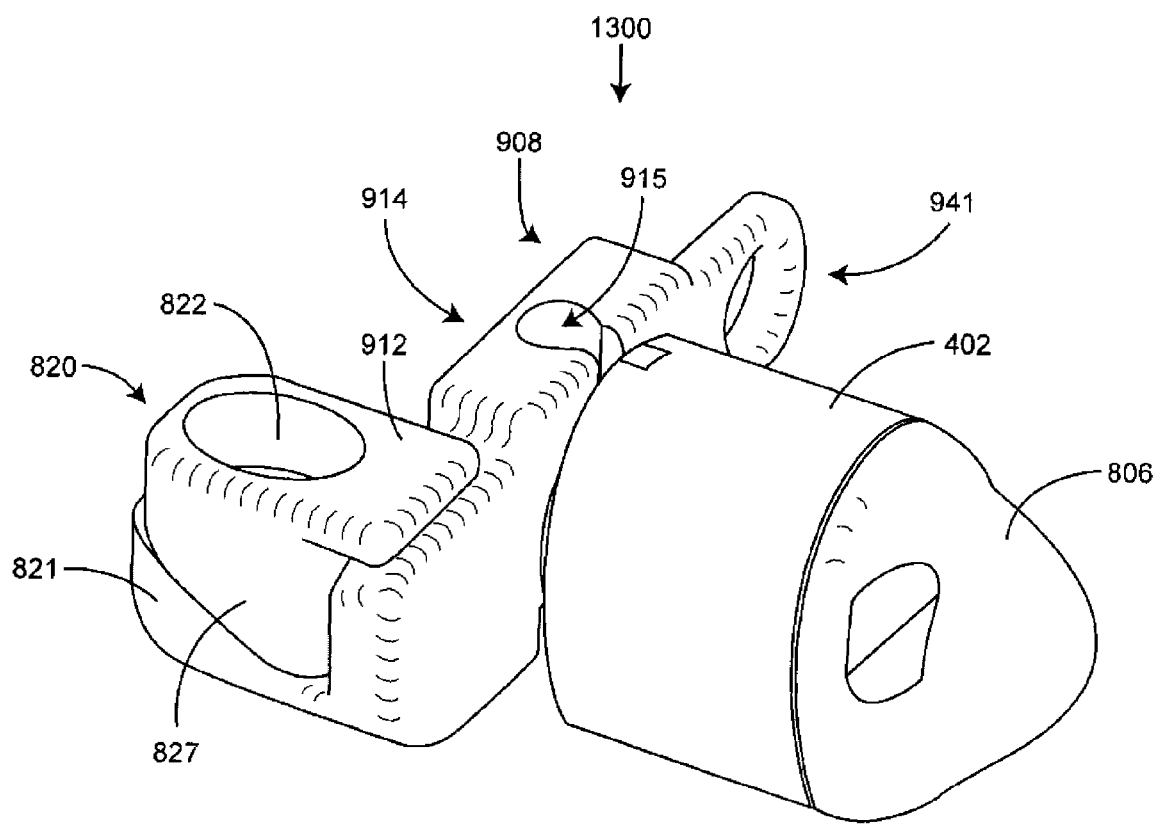
FIG. 9B is a perspective view the implant of FIG. 9A wherein the capture device is arranged to secure a binder between the capture device and the brace.
Figure 9C:
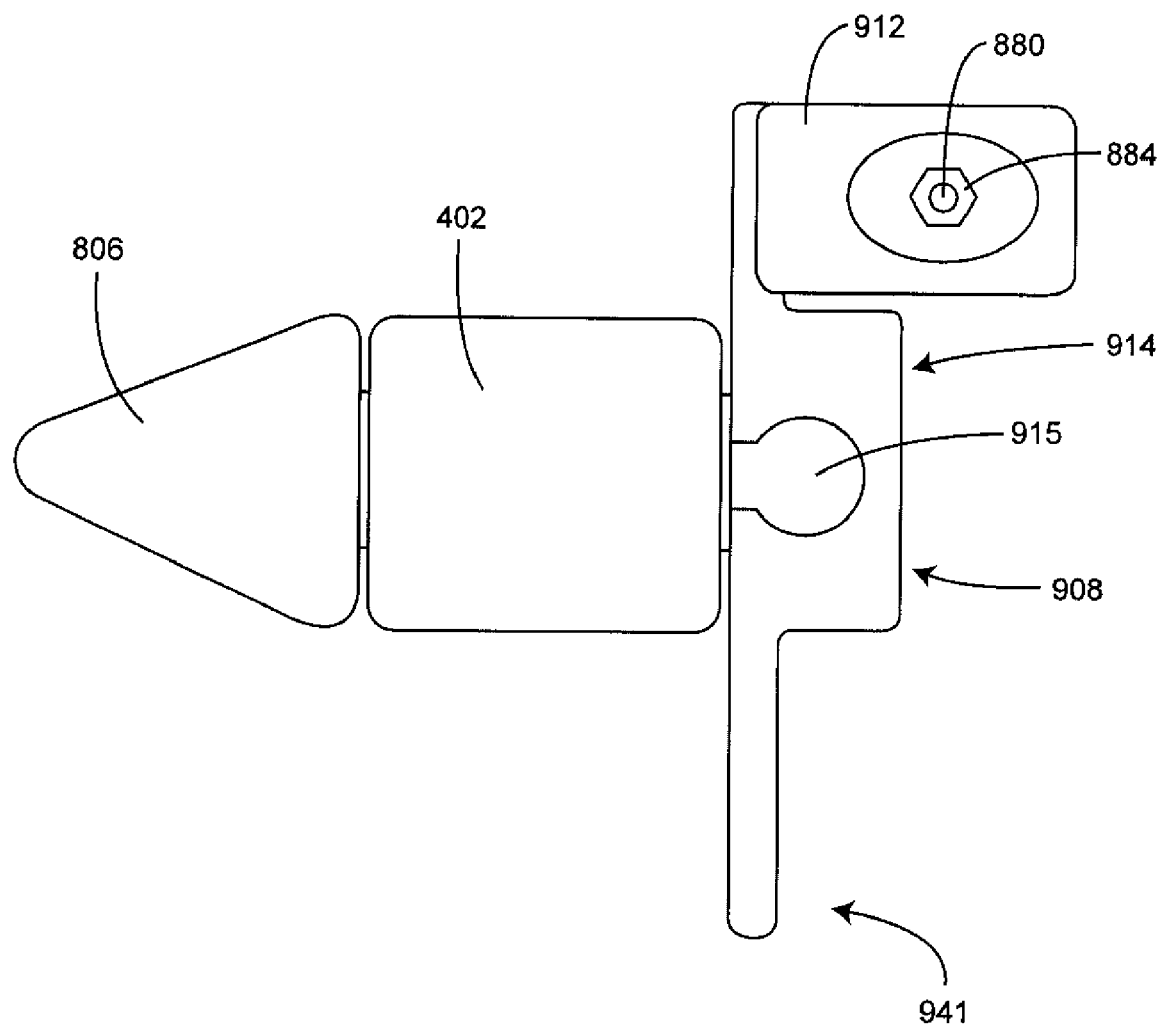
FIG. 9C is a side view of the implant of FIGS. 9A and 9B.

FIGS. 9A and 9B are perspective views, and FIG. 9C is a side view of a still further embodiment of an implant in accordance with the present invention. The implant 1300 includes a distraction guide 806, a rotatable spacer 402, and a brace 908. As above, a binder 330 can be fixedly connected with the brace 908 at a proximal end 332 of the binder 330. Once positioned around adjacent spinous processes, tension of the binder 330 can be set when the binder 330 is secured to the brace 908 so that relative movement of the adjacent spinous processes during flexion is limited or prevented, as desired.

As can be seen in FIG. 9A, the brace 908 can include a first end having an eyelet 941 through which the proximal end 332 of the binder 330 can be threaded and subsequently sutured, knotted or otherwise bound, or alternatively looped through the eyelet 941 and secured to itself (e.g., using a clasp) so that the proximal end 332 of the binder 330 cannot be drawn through the eyelet 941. One of ordinary skill in the art can appreciate the myriad different ways in which the proximal end 332 of the binder 330 can be associated with the brace 908 so that tension can be applied to the binder 330. As in previous embodiments, a free end of the binder 330 can be secured to the brace 908 by a capture device 820 associated with the brace 908. The capture device 820 of FIGS. 9A-11 is arranged at a second end of the brace 908 opposite the eyelet 941, rather than approximately centered along the brace wall 914. The brace 908 can optionally include a locking pin hole 915 that can be engaged by a locking pin of an insertion instrument (not shown), for example as described in U.S. Pat. No. 6,712,819 to Zucherman, et al., incorporated herein by reference. Further, similar to implants described in Zucherman '819, the brace wall 914 can optionally include one or more holes 916 (shown in FIG. 11) adapted to receive alignment pins of such an insertion instrument, and the spacer 402 can include a spacer engagement hole adapted to receive a spacer engagement pin of such an insertion instrument. When a spacer engagement pin engages the spacer engagement hole, rotation of the spacer 402 can be limited or blocked. Once the spacer engagement pin is released from the spacer engagement hole, the spacer 402 can rotate and/or swivel about a central body 917 without impedance from the spacer engagement pin. Such an arrangement can provide a physician additional control over the positioning of the implant 1300, although in other embodiments the spacer 402 need not include an engagement hole. Arranging the captured device 820 at a second end of the brace 908 can allow an insertion instrument, having a configuration as described in Zucherman '819 or having some other configuration, to releasably engage the implant 1300 to assist in implantation without interference from the capture device 820.

The distraction guide 806 of the implant 1300 can be wedge-shaped, as described above, or approximately conical, as shown in FIGS. 9A-9C, and can include a slot 809 disposed through the distraction guide 806 and adapted to receive the binder 330 during implantation. Also as described above, the rotatable spacer 402 can be elliptical in cross-section, or otherwise shaped, and can rotate relative to the distraction guide 806 to roughly conform with a contour of a space between the targeted adjacent spinous processes.

Figure 10A:
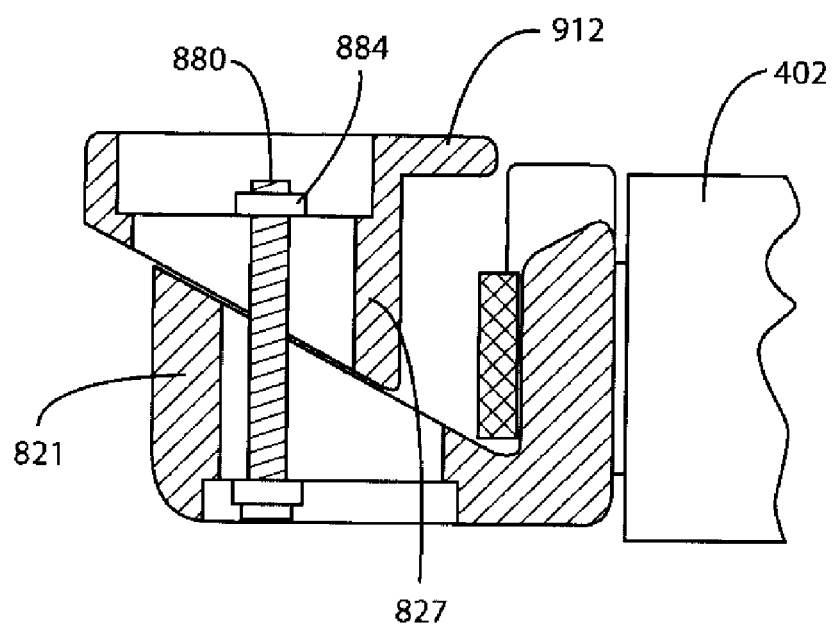
FIG. 10A is a cross-sectional top view of a binder loosely positioned within the capture device of the implant of FIGS. 9A and 9B.
Figure 10B:
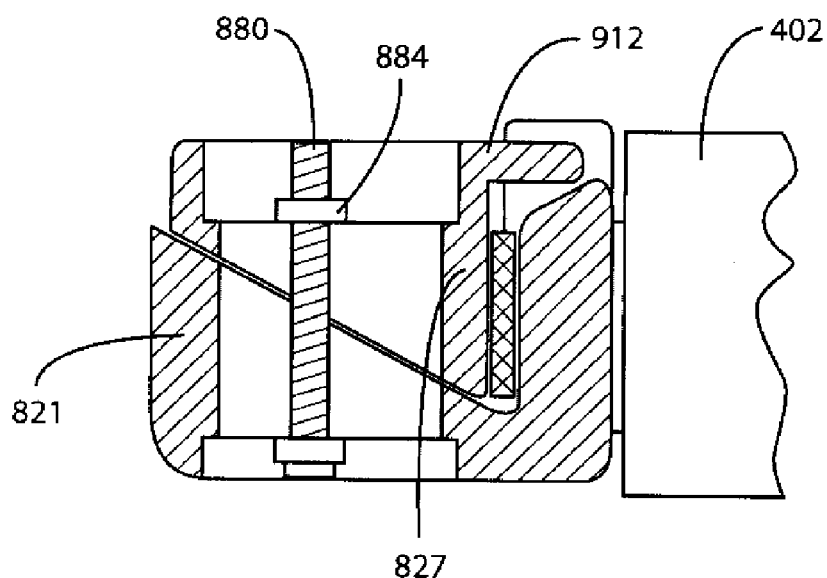
FIG. 10B is a cross-sectional top view of the binder secured to the brace by the capture device of the implant of FIGS. 9A and 9B.
Figure 10C:
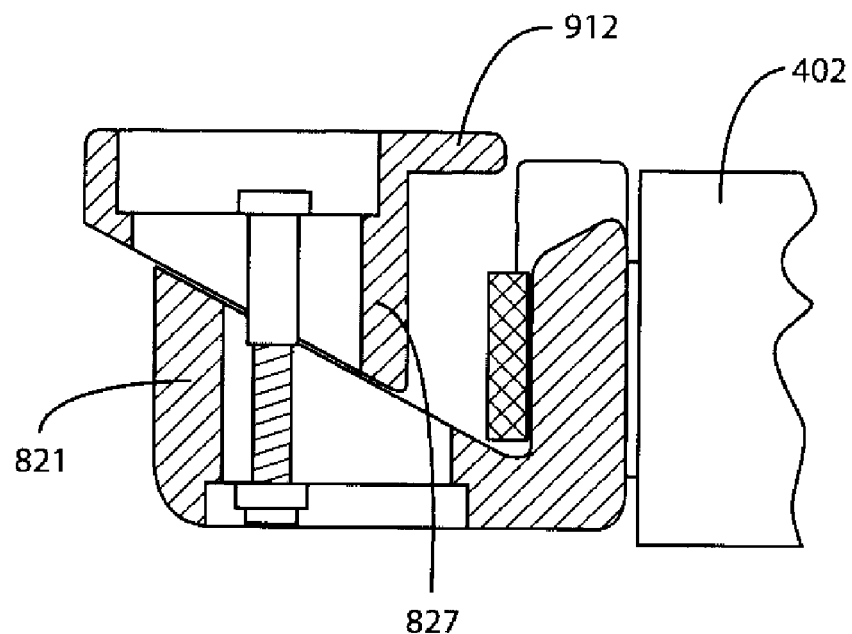
FIG. 10C is a cross-sectional top view of a binder loosely positioned within an alternative embodiment of a capture device of the implant of FIGS. 9A and 9B.
Figure 10D:
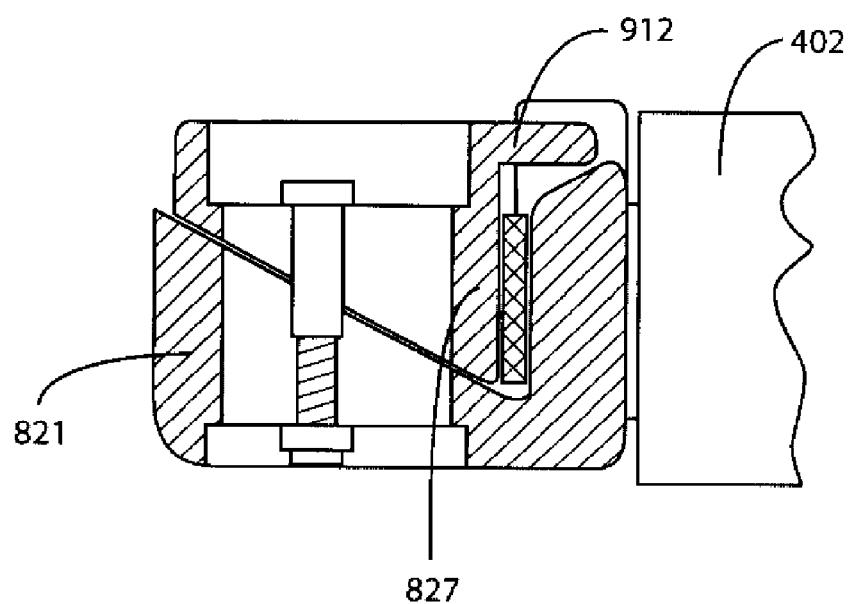
FIG. 10D is a cross-sectional top view of the binder and capture device of FIG. 10C wherein the binder is secured to the brace

The capture device 820 is shown in cross-section in FIGS. 10A and 10B. The capture device 820 can comprise, for example, two pieces slidably associated with one another by an adjustable fastener 822 (as shown, the adjustable fastener is a hex screw). A fixed piece 821 of the capture device can extend from the brace wall 914. The fixed piece 821 can include a beveled surface 823 that can function as a ramp. A slidable piece 827 of the capture device can be slidably associated with the fixed piece 821, and can likewise included a beveled surface 829 positioned in opposition to the beveled surface 823 of the fixed piece 821. As shown, the slidable piece 827 is associated with the fixed piece 821 via an adjustable fastener 822. The fastener 822 can be positioned within slots 890,892 of the fixed piece 821 and the slidable piece 827 and can include a threaded shaft 880, a head 882, and a nut 884. The head 882 of the fastener 822 can engage an anterior surface 894 of the fixed piece 821 and the nut 884 can be threaded onto the threaded shaft 880 so that the nut 884 can engage a posterior surface 896 of the slidable piece 827. The slidable piece 827 is free to slide along the beveled surface 823 of the fixed piece 821 until both the nut 884 engages the posterior surface 896 and the head 882 engages the anterior surface 894, blocking further movement in one direction. The distance between the anterior surface 894 and the posterior surface 896 increases or decreases as the slidable piece 827 slides along the beveled surface 823 and a distance between a capture surface 898 of the slidable piece 827 and the brace wall 914 likewise increases or decreases. The maximum distance the slidable piece 827 can travel can be defined by the distance between the nut 884 and the head 882. A physician can adjust the maximum distance by rotating the nut 884 so that the nut 884 travels closer to, or farther from the head 882 along the threaded shaft 880, possibly urging the capture surface 898 toward the brace wall 914. Thus, when the implant 1300 is positioned between spinous processes, the physician can set the maximum distance so that the free end of the binder 330 can be threaded between the capture surface 898 and the brace wall 914. As shown in FIG. 10B, the physician can then adjust the fastener 822 so that the posterior surface 896 and the anterior surface 894 are urged together, the maximum distance decreases and the distance between the capture surface 898 and the brace wall 914 decreases, thereby pinching the binder 330 between the capture surface 898 and the brace wall 914 and defining a secure end of the binder 330. In some embodiments, one or both of the capture surface 898 and the brace wall 914 can include texture so that the binder 330 is further prevented from sliding when the binder 330 is placed under increasing tension (e.g., during flexion).

The slidable piece 827 can optionally further include a guide 912 extending from the slidable piece 827 so that the guide 912 overlaps a portion of the brace 908. The guide 912 can extend, for example, a distance roughly similar to the maximum distance between the capture surface 898 and the brace wall 914, and can help ensure that the binder 330 is captured between the capture surface 898 and the brace wall 914. In other embodiments, the capture device 820 of FIGS. 9A-10B can include some other shape or configuration and still fall within the contemplated scope of the invention. For example, the fastener need not include a nut. In one embodiment, shown in FIGS. 10C and 10D, the fastener 922 can include a threaded shaft 980 associated with a sleeve 984. As one of the threaded shaft 980 and the sleeve 984 is rotated, the distance between a head 982 of the threaded shaft 980 and the head 985 of the sleeve 984 can decrease or increase. In still other embodiments, the fastener need not include a threaded shaft, but rather can include a smooth shaft having a retaining clip frictionally associated with the smooth shaft. One of ordinary skill in the art will appreciate the myriad different devices that can be employed to selectively close a gap between a capture surface 898 and the brace wall 914.

Figure 11:
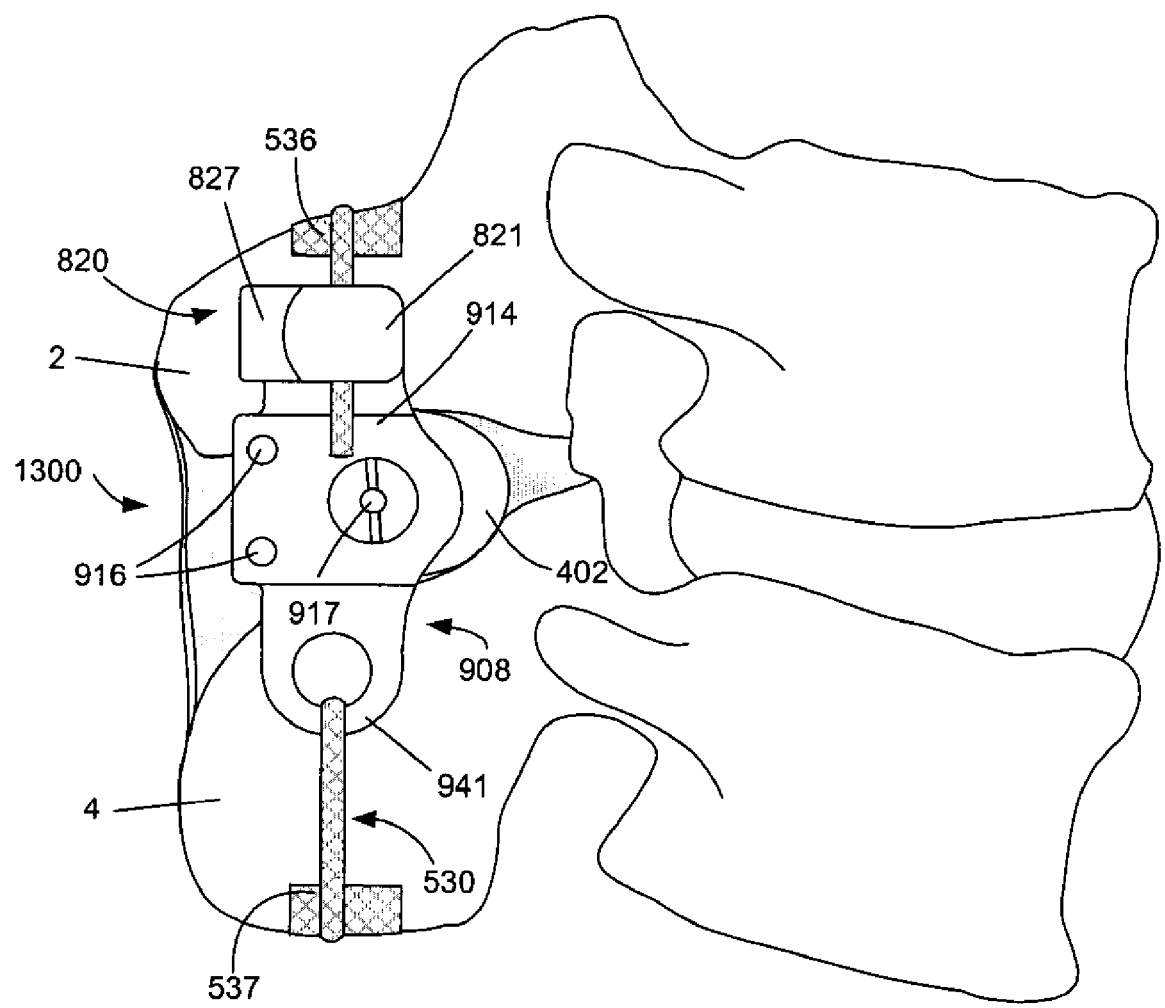
FIG. 11 is an end view of the implant of FIGS. 9A and 9B positioned between adjacent spinous processes.

FIG. 11 is an end view of the implant 1300 of FIGS. 9A-10D positioned between adjacent spinous processes. As shown, the binder 530 is a cord, but in other embodiments can have some other geometry. As described above in reference to previous embodiments, where a cord, a tether, or the like is used as a binder, a pad 536 can be arranged along a contact surface of the respective spinous process so that a load applied to the contact surface by the tension in the binder 530 can be distributed across a portion of the contact surface wider than the binder 530, thereby reducing stress on the portion. The capture device 820 is arranged so that the slidable piece 827 is posteriorly located relative to the fixed piece 821. A fastener 822 can be accessed by the physician using a substantially posterior approach.

Figure 12:
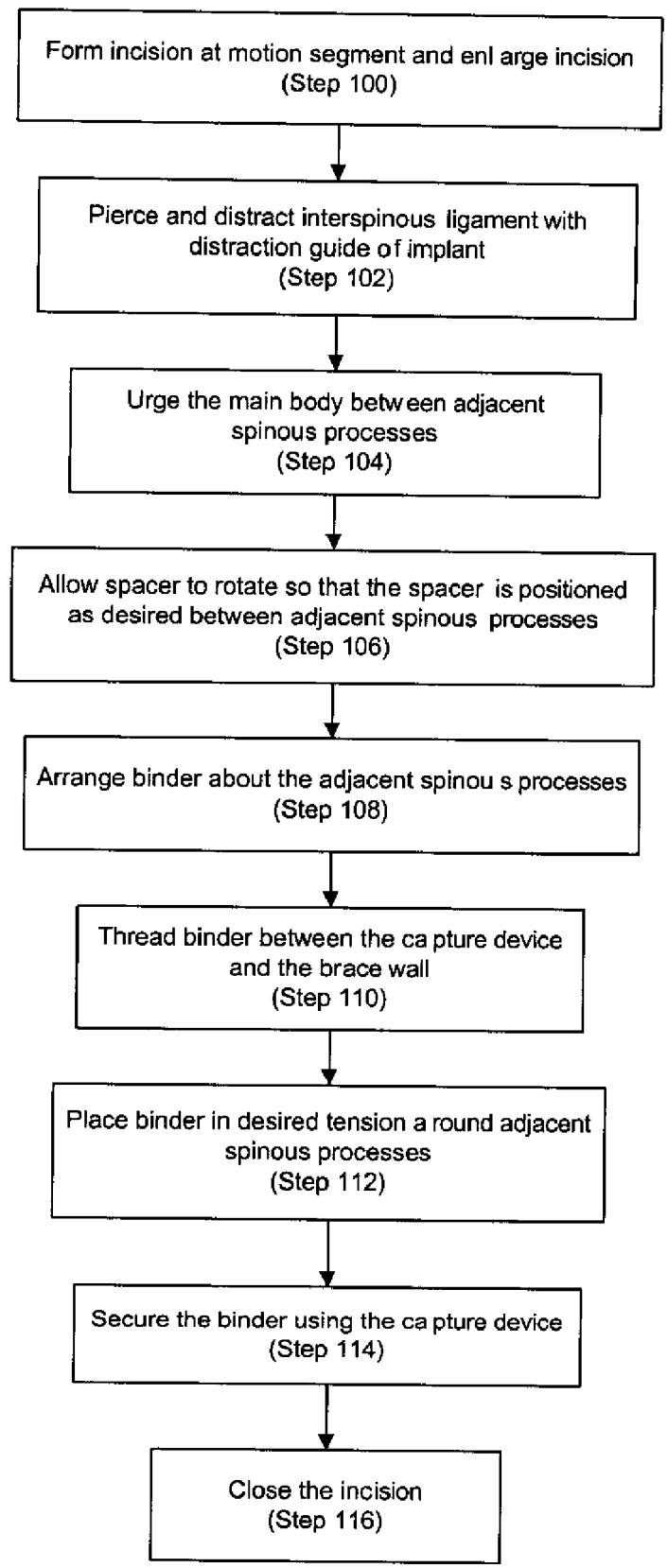
FIG. 12 is a block diagram illustrating a method of positioning the implant of FIGS. 9A-11 between adjacent spinous processes.

A method of surgically implanting an implant 1300 in accordance with an embodiment as described above in FIGS. 9A-11 of the present invention is shown as a block diagram in FIG. 12. The method can include forming an incision at the target motion segment, and enlarging the incision to access the target motion segment (Step 100). The interspinous ligament between targeted adjacent spinous processes can then be distracted by piercing or displacing the interspinous ligament with the distraction guide 106 (Step 102) and urging the implant 1300 between the adjacent spinous processes (Step 104). As the interspinous ligament is displaced, the spacer 302 can be positioned between the spinous processes such that the spacer 302 can rotate to assume a preferred position between the spinous processes (Step 106). Once the implant 1300 is positioned, the binder 330 can be threaded between interspinous ligaments of adjacent motion segments so that the targeted adjacent spinous processes are disposed within a loop formed by the binder 330 (Step 108). The physician can then thread the binder 330 between the capture surface 898 of the capture device 820 and the brace wall 914 (Step 110). Once a desired tension of the binder 330 is applied (Step 112), the physician can adjust the fastener 822 of the capture device 820 so that the binder 330 is secured between the captured surface 898 and the brace wall 914 (Step 114). The incision can subsequently be closed (Step 116).

Figure 13A:
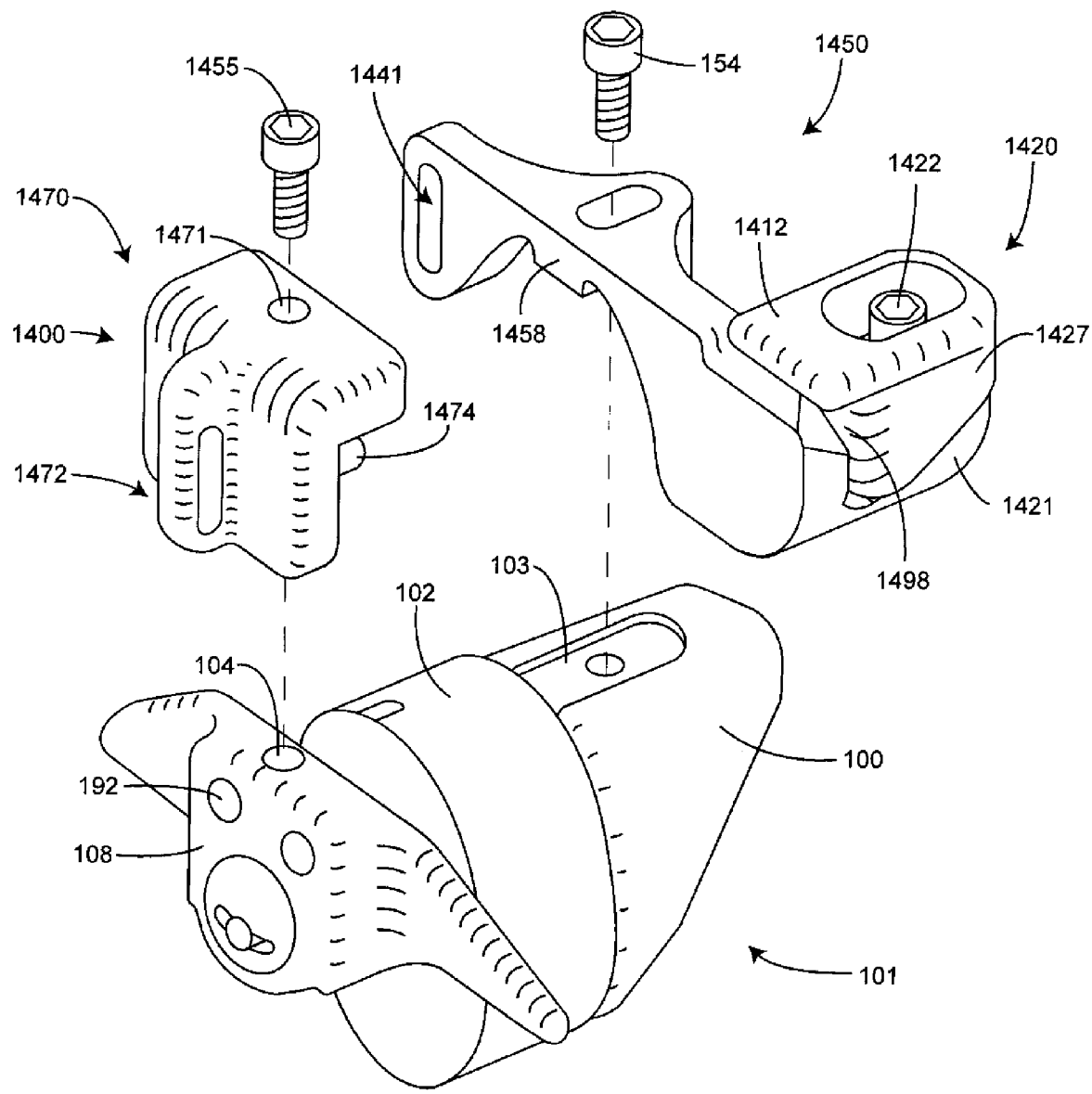
FIG. 13A is a perspective view of an still another embodiment of an implant in accordance with the present invention having a distraction guide, a spacer, a first wing, and a second wing including a capture device.
Figure 13B:
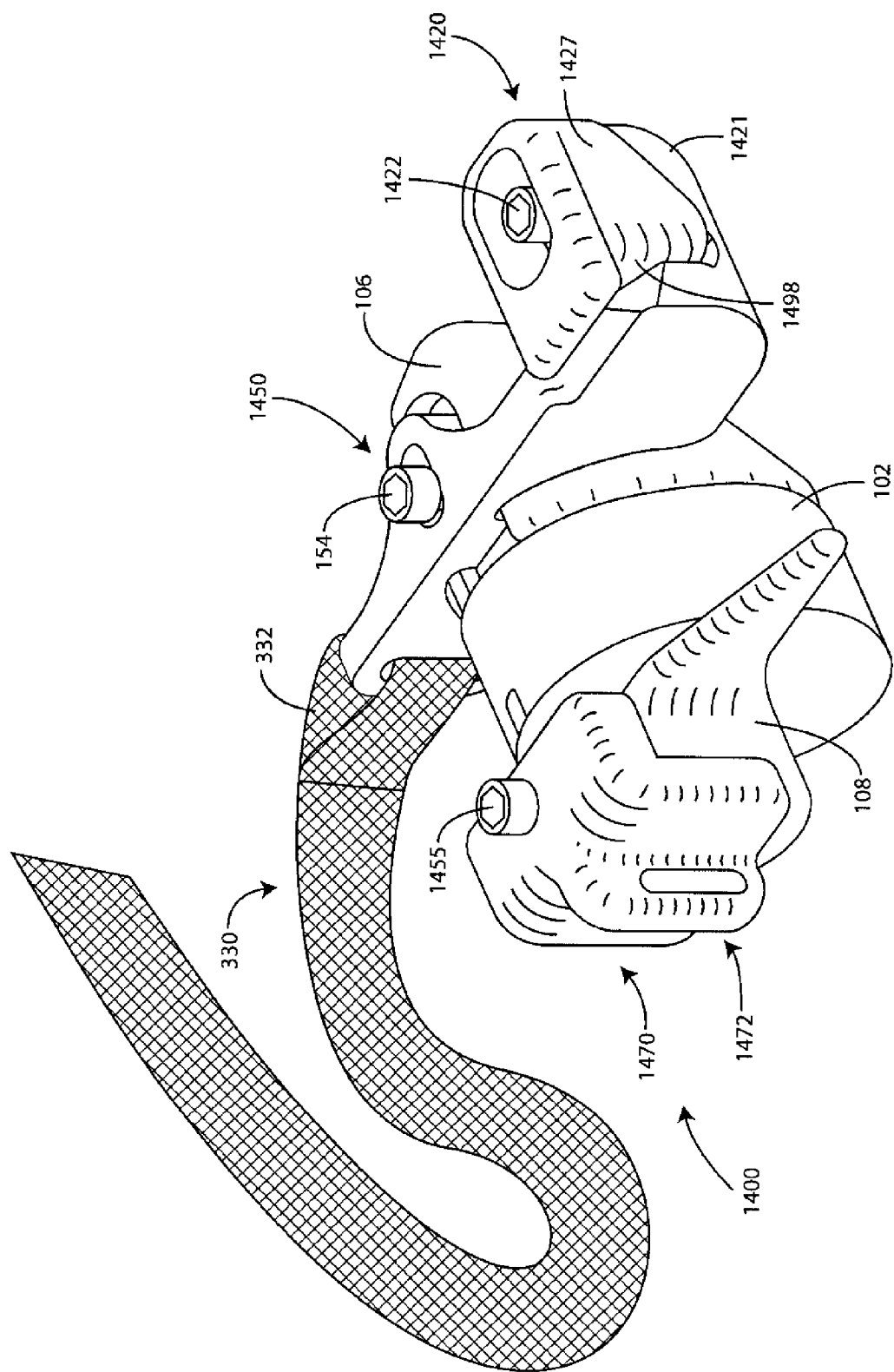
FIG. 13B is a perspective view of the implant of FIG. 13A in accordance with the present invention having a distraction guide, a spacer, a first wing, and a second wing including a capture device.

FIGS. 13A and 13B are perspective views of still another embodiment of an implant 1400 in accordance with the present invention. In such an embodiment, the implant 1400 can include a main body 101 similar to the main body 101 described above in reference to FIG. 1. As above, the main body 101 (also referred to herein as a first unit) includes a spacer 102, a first wing 108, a distraction guide 106 and an alignment track 103. The main body 101 is inserted between adjacent spinous processes. Preferably, the main body 101 remains (where desired) in place without attachment to the bone or ligaments.

Figure 15:
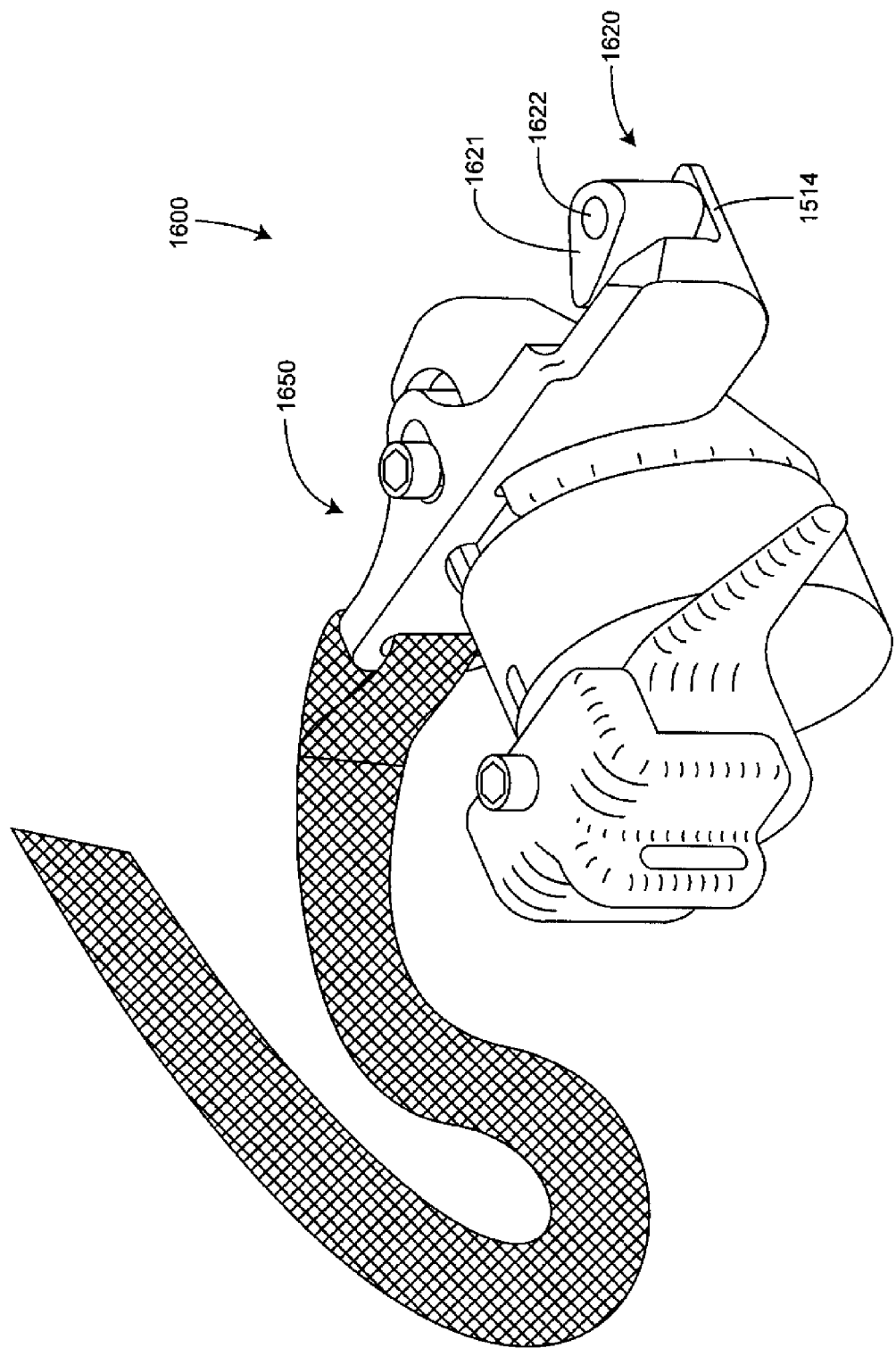
FIG. 15 is a perspective view of an still another embodiment of an implant in accordance with the present invention having a distraction guide, a spacer, a first wing, and a second wing including a capture device.

The alignment track 103 includes a threaded hole for receiving a fastener. The alignment track 103 need not include a threaded hole, but rather alternatively can include some other mechanism for fixedly connecting an additional piece (such as a second wing for limiting or blocking movement of an implant along the longitudinal axis). For example, in an alternative embodiment, the alignment track 1403 can include a flange so that the second wing 1450 can be slidably received, as shown in FIG. 15.

As further shown in FIGS. 13A and 13B, the implant 1400 includes a second wing 1450 removably connectable with the implant 1400. The second wing 1450 includes an alignment tab 1458 adapted to be received in the alignment track 103 of the main body 101, the alignment tab 1458 optionally including a slot for receiving the fastener so that the alignment tab 1458 is disposed between the fastener and the alignment track 103. In alternative embodiments, the alignment tab 1458 need not include a slot but rather can include some other mechanism for mating with the main body 101.

The second wing 1450 can include a first end having a slot (or eyelet) 1441 through which the proximal end (also referred to herein as an anchored end) 332 of a binder 330 can be threaded and subsequently sutured, knotted or otherwise bound, or alternatively looped through the slot 1441 and secured to itself (e.g., using a clasp) so that the proximal end 332 of the binder 330 cannot be withdrawn through the slot 1441. One of ordinary skill in the art can appreciate the myriad different ways in which the proximal end 332 of the binder 330 can be associated with the second wing 1450 so that tension can be applied to the binder 330. The binder 330 can be disposed around adjacent spinous processes and a portion of the length of the binder 330 (the length of the binder being that portion of the binder extending from the proximal end of the binder) can be secured to the second wing 1450 by a capture device 1420 associated with the second wing 1450.

The capture device 820 of FIGS. 13A and 13B is arranged at a second end of the second wing 1450 opposite the slot 1441. The capture device 1420 can be substantially similar to capture devices 1420 as described above in reference to FIGS. 10A and 10B, and can comprise, for example, two pieces slidably associated with one another by an adjustable fastener. As above, a fixed piece 1421 of the capture device can extend from the second wing 1450. The fixed piece 1421 can include a beveled surface that can function as a ramp. A slidable piece 1427 of the capture device can be slidably associated with the fixed piece 1421 (for example, via the adjustable fastener) and can likewise included a beveled surface positioned in opposition to the beveled surface of the fixed piece 1421. As the slidable piece 1427 slides along the beveled surface of the fixed piece 1421, a distance between a capture surface 1498 of the slidable piece 1427 and the second wing 1450 increases or decreases. As above, the slidable piece 1427 can optionally further include a guide 1412 extending from the slidable piece 1427 so that the guide 1412 overlaps a portion of the second wing 1450. The guide 1412 can extend, for example, a distance roughly similar to the maximum distance between the capture surface 1498 and the second wing 1450, and can help ensure that the binder 330 is arranged between the capture surface 1498 and the second wing 1450.

A physician can position the binder 330 so that the binder 330 is disposed between adjacent spinous processes, threading the binder 330 between the slidable piece 1427 and the second wing 1450. The physician can then adjust the fastener 1422 so that the distance between the capture surface 1498 and the second wing 1450 decreases, thereby pinching the binder 330 between the capture surface 1498 and the second wing 1450 and defining a secure end of the binder 330. In some embodiments, one or both of the capture surface 1498 and the second wing 1450 can include texture so that the binder 330 is further prevented from sliding when the binder 330 is placed under increasing tension (e.g., during flexion).

The implant 1400 can further include a binder aligner 1470 selectably connectable with the first wing 108 of the main body 101. The binder aligner 1470 can be connected with the first wing 108 by fastening the binder aligner 1470 to the locking pin hole 104 of the first wing 108. In such embodiments where a fastener 1455 is used to connect the binder aligner 1470 with the first wing 108 through a hole 1471 in the binder aligner 1470, it is desirable that the locking pin hole 104 be threaded, or otherwise adapted to receive the fastener 1455. The locking pin hole 104 can thus be adapted to function as a hole to slidably (and temporarily) receive a locking pin of an insertion tool (not shown), thereby facilitating insertion and positioning of the main body 101, and can also be adapted to function to fixedly receive a fastener 1455 for positioning the binder aligner 1470. The binder aligner 1470 can optionally include pins 1474 corresponding to the alignment holes 192 of the main body 101 to further secure the binder aligner 1470 to the main body 101 and limit undesired movement of the binder aligner 1470 relative to the main body 101.

The binder aligner 1470 includes a guide 1472 extending from the binder aligner 1470 to limit or block shifting of the binder 330 in a posterior-anterior direction. The guide 1472 can include a loop, as shown in FIG. 13A, or alternatively some other structure, closed or unclosed, for limiting or blocking shifting of the binder 330. Such a structure can prevent undesired relative movement between the binder 330 and the main body 101, and can additionally ease arrangement of the binder 330 during an implantation procedure, by helping to aid proper positioning of the binder 330.

Figure 14:
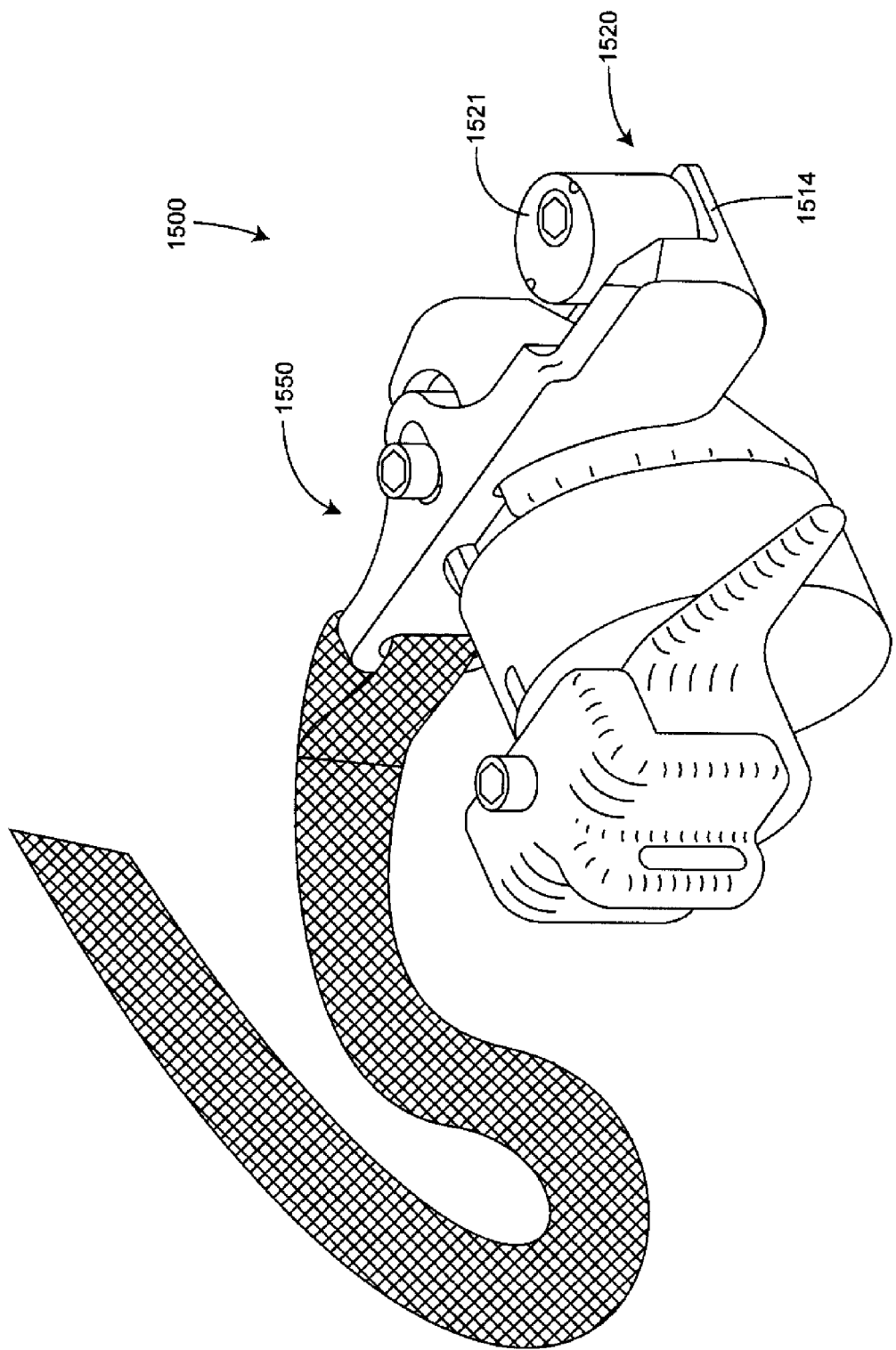
FIG. 14 is a perspective view of a still another embodiment of an implant in accordance with the present invention having a distraction guide, a spacer, a first wing, and a second wing including a capture device.

In other embodiments, the capture device of FIGS. 13A and 13B can include some other shape, configuration, and mechanism and still fall within the contemplated scope of the invention. For example, referring to FIG. 14, in other embodiments, a flange 1514 can extend from the second wing 1550, from which a rotatable cam 1521 extends so that the binder 330 can be captured between the second wing 1550 and the cam 1521. Such a capture device can resemble capture devices 1520 as described above in FIGS. 3C and 3B. Referring to FIG. 15, in still other embodiments, a spring-loaded cam 1621 extends from the flange 1514 so that the binder 330 can be captured between the second wing 1514 and the spring-loaded cam 1621. Such a capture device can resemble capture devices 1520 as described above in FIGS. 3C and 3D. In still further embodiments in accordance with the present invention, some other mechanism can be employed as a capture device associated with the second wing 1550 for securing the length of the binder 330, for example as otherwise described in herein, and other obvious variations. One of ordinary skill in the art will appreciate the myriad different mechanisms for securing the binder 330 to the second wing 1450.

A system in accordance with the present invention can comprise a second wing 1450 including a capture device 1420 as described above and optionally a binder aligner 1470. The system can be used with a main body 101 in substitution for a second wing 150 as described above in FIG. 1. Alternatively, the system can optionally be used to modify a main body 101 previously implanted in a patient, for example by removing an existing second wing 150 and replacing the second wing 150 with the system, to additionally limit flexion as well as extension. Such a system can provide flexibility to a physician by allowing the physician to configure or reconfigure an implant according to the needs of a patient. Further, such a system can reduce costs by reducing the variety of components that need be manufactured to accommodate different procedures and different treatment goals.

Figure 16:
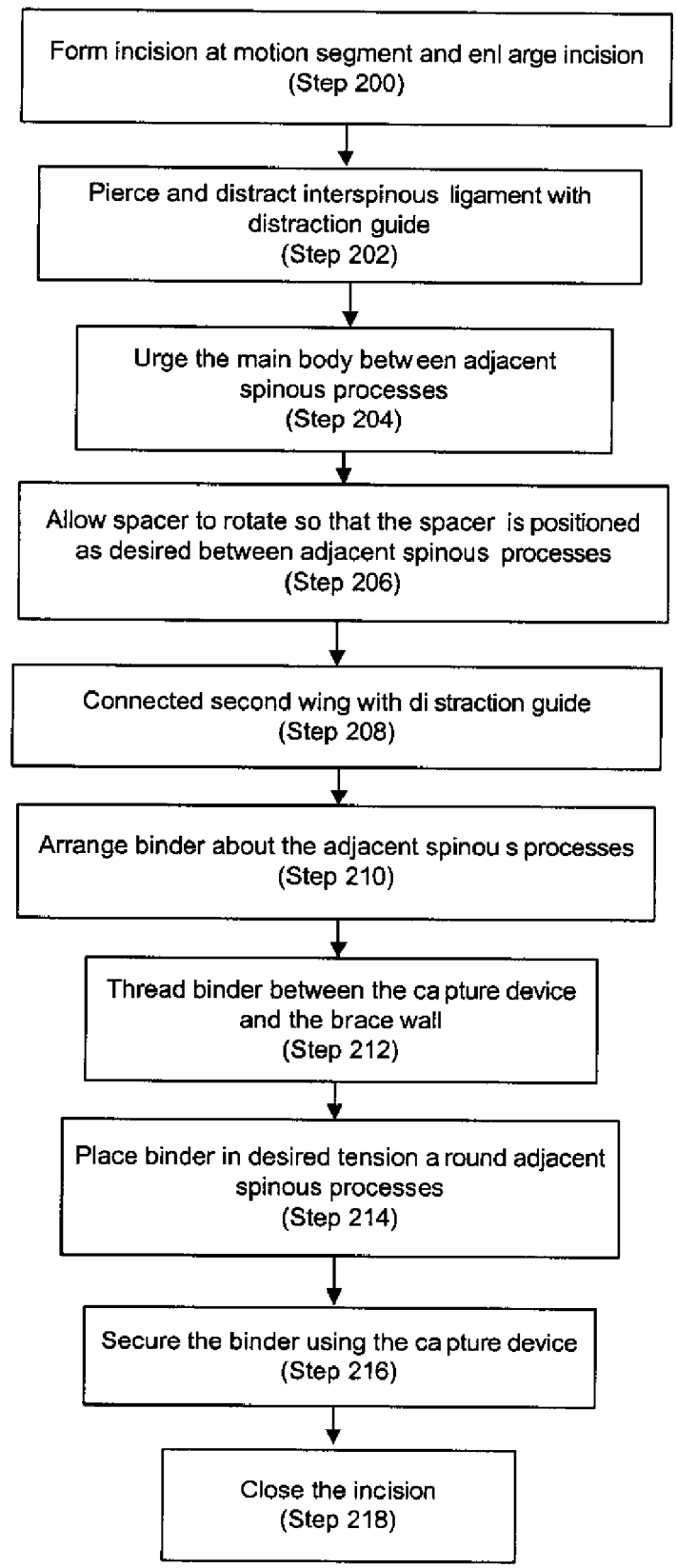
FIG. 16 is a block diagram illustrating a method of positioning the implant of FIGS. 13A-15 between adjacent spinous processes.

A method of surgically implanting an implant 1400 in accordance with an embodiment as described above in FIGS. 13A-15 of the present invention is shown as a block diagram in FIG. 16. The method can include forming an incision at the target motion segment, and enlarging the incision to access the target motion segment (Step 200). The interspinous ligament between targeted adjacent spinous processes can then be distracted by piercing or displacing the interspinous ligament with the distraction guide 106 (Step 202) and urging the implant 1400 between the adjacent spinous processes (Step 204). As the interspinous ligament is displaced, the spacer 102 can be positioned between the spinous processes such that the spacer 102 can rotate to assume a preferred position between the spinous processes (Step 206). Once the implant 1400 is positioned, the second wing 1450 can be fixedly connected with the distraction guide 106 (Step 208). A binder 330 associated with the second wing 1450 can be threaded between interspinous ligaments of adjacent motion segments so that the targeted adjacent spinous processes are disposed within a loop formed by the binder 330 (Step 210). The physician can then thread the binder 330 between the capture surface 1498 of the capture device 1420 and the second wing 1450 (Step 212). Once a desired tension of the binder 330 is applied (Step 214), the physician can adjust the fastener 1422 of the capture device 1420 so that the binder 330 is secured between the captured surface 1498 and the second wing 1450 (Step 216). The incision can subsequently be closed (Step 218).

Figure 17A:
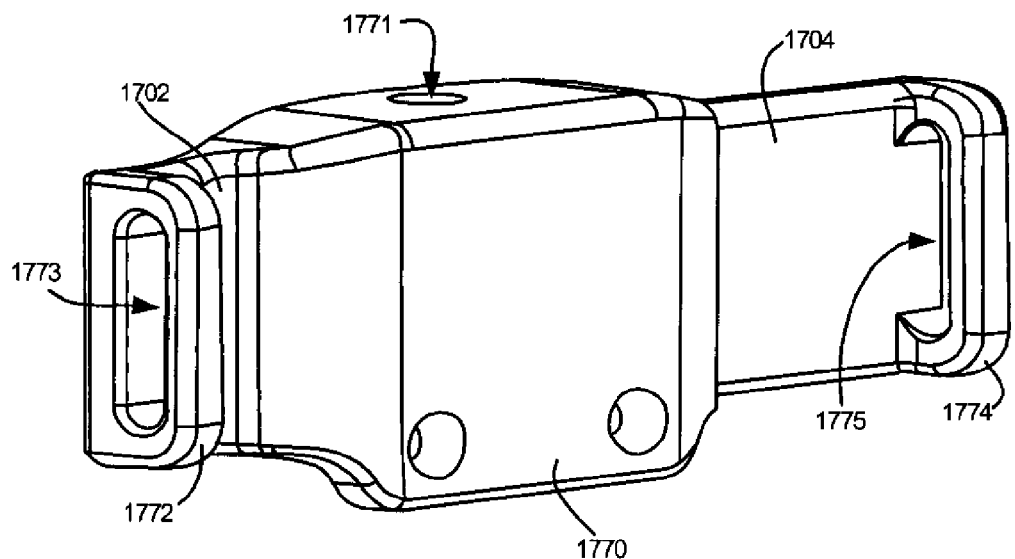
FIGS. 17A and 17B are perspective and bottom views of a binder aligner in accordance with one embodiment of the invention.
Figure 17B:
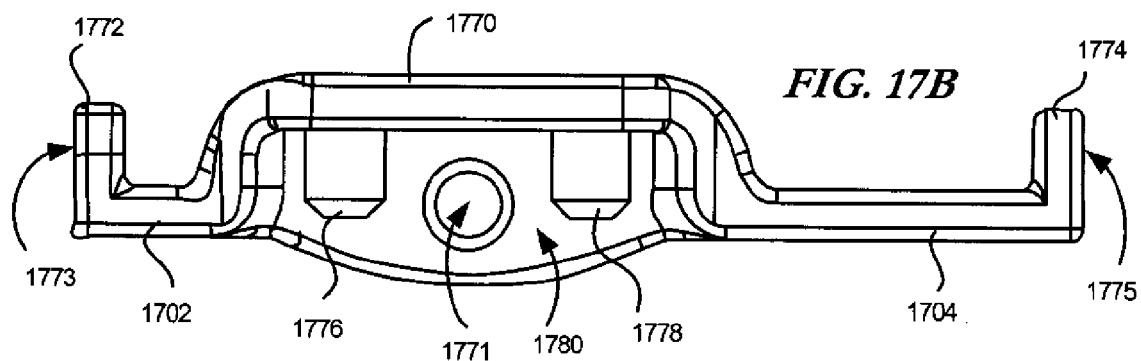

FIGS. 17A and 17B are perspective and bottom views of a binder aligner 1770 selectably connectable with the first wing 108 of the main body 101 in accordance with one embodiment of the invention. Binder aligner 1770 includes a hole 1771 for receiving a fastener to connect binder aligner 1770 with main body 101. Binder aligner 1770 includes a longitudinal section which comprises a first arm 1702 and a second arm 1704 on either side of the fastener hole 1771. At the end of each arm, furthest from the fastener hole, each arm 1702, 1704, includes a guide 1772, 1774 extending from the binder aligner 1770 to limit or block shifting of the binder 330 in a posterior-anterior direction. The guides 1772, 1774 can include a closed loop, as shown in FIGS. 17A, B or alternatively some other structure, closed or unclosed, for limiting or blocking shifting of the binder 330. The closed loop or other structure can prevent undesired relative movement between the binder 330 and the main body 101, and can additionally ease arrangement of the binder 330 during an implantation procedure, by helping to aid proper positioning of the binder 330. The binder aligner 1770 can optionally include pins 1776, 1778 corresponding to the alignment holes 192 of the main body 101 to further secure the binder aligner 1770 to the main body 101 and limit undesired movement of the binder aligner 1770 relative to the main body 101. The pins 1776, 1778 and interior surface 1780 of binder aligner 1770 form a surface which is complementary to the exterior or mating surface of the main body. The engagement of the holes 192 by the pins 1776, 1778 aligns the longitudinal axis of the binder aligner with the longitudinal axis of the first wing 108.

Figure 17C:
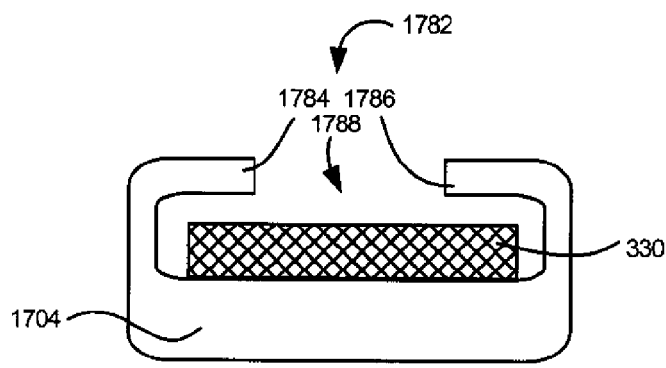
FIG. 17C is an end view of a binder aligner in accordance with an alternative embodiment of the invention.

FIG. 17C shows an end view of an alternative guide 1782 according to one embodiment of the invention. Guide 1782 is mounted on the end of an arm 1704 of binder aligner 1770. In this embodiment, guide 1782 is an open loop comprising two guide elements 1784, 1786 separated by a slot 1788. A binder 330 is shown in sectional view in position in guide 1782. Note that during implantation, binder 330 may be passed through slot 1788 of guide 1782 obviating the need to thread binder 330 through the guide. However, when tension is applied to binder 330 it is secured such that it can no longer escape through slot 1788 but is secured in position by the two guide elements 1784, 1786.

Figure 18A:
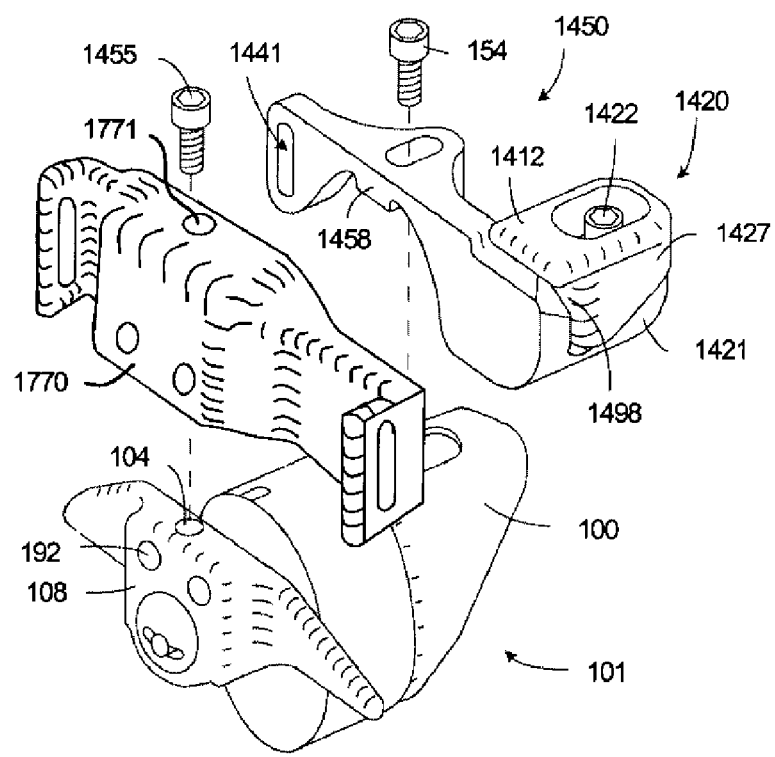
FIGS. 18A and 18B are perspective views of the binder aligner of FIGS. 17A, B illustrating mounting of the binder aligner to a wing of an implant in accordance with one embodiment of the present invention.
Figure 18B:
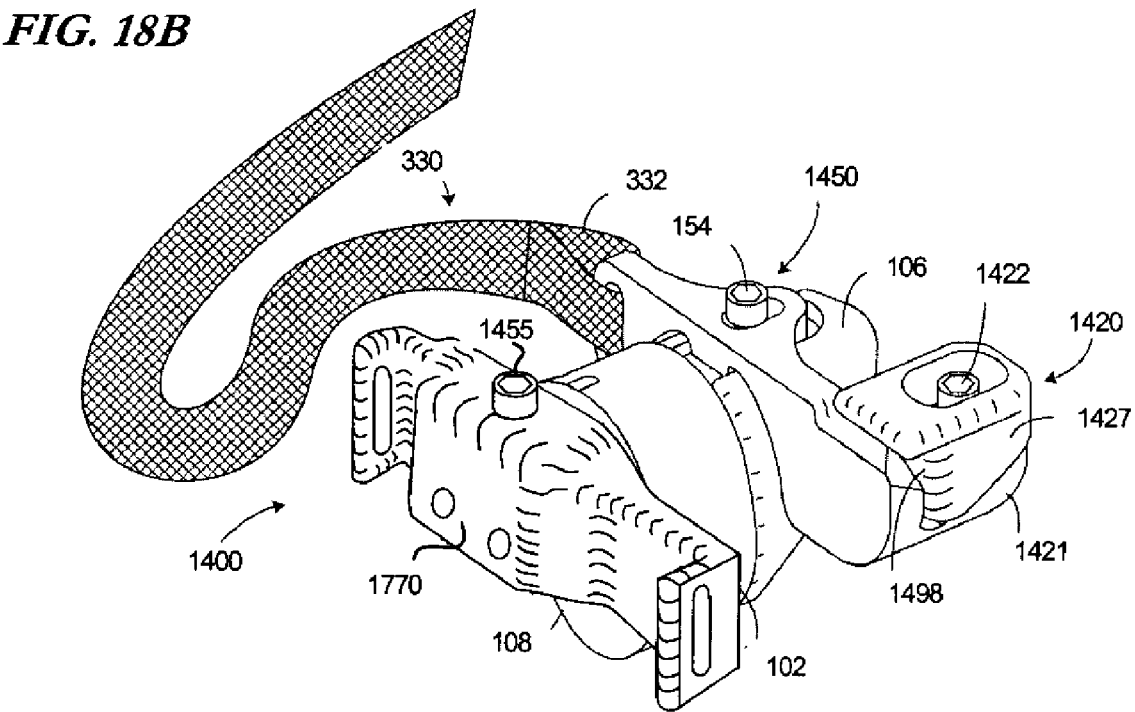

FIGS. 18A and 18B are perspective views of the binder aligner of FIGS. 17A, B illustrating mounting of the binder aligner to a main body 101 of an implant in accordance with one embodiment of the present invention. FIG. 18A is an exploded view illustrating the alignment of the main body 101 with the binder aligner 1770 and second wing 1450. The binder aligner 1770 can be connected with the first wing 108 by placement of a fastener 1455 through hole 1771 into locking pin hole 104 of the first wing 108. In such embodiments where a fastener 1455 is used to connect the binder aligner 1770 with the first wing 108 through a hole 1771 in the binder aligner 1770, it is desirable that the locking pin hole 104 be threaded, or otherwise adapted to receive the fastener 1455. The locking pin hole 104 can thus be adapted to function as a hole to slidably (and temporarily) receive a locking pin of an insertion tool (not shown), thereby facilitating insertion and positioning of the main body 101, and can also be adapted to function to fixedly receive a fastener 1455 for securing the binder aligner 1770. FIG. 18B is a perspective view of an implant after binder aligner 1770 has been connected with first wing 108 and after second wing 1450 has been connected with main body 101. Note that the longitudinal axis of binder aligner 1770 is aligned with first wing 108 and also with second wing 1450.

Figure 18C:
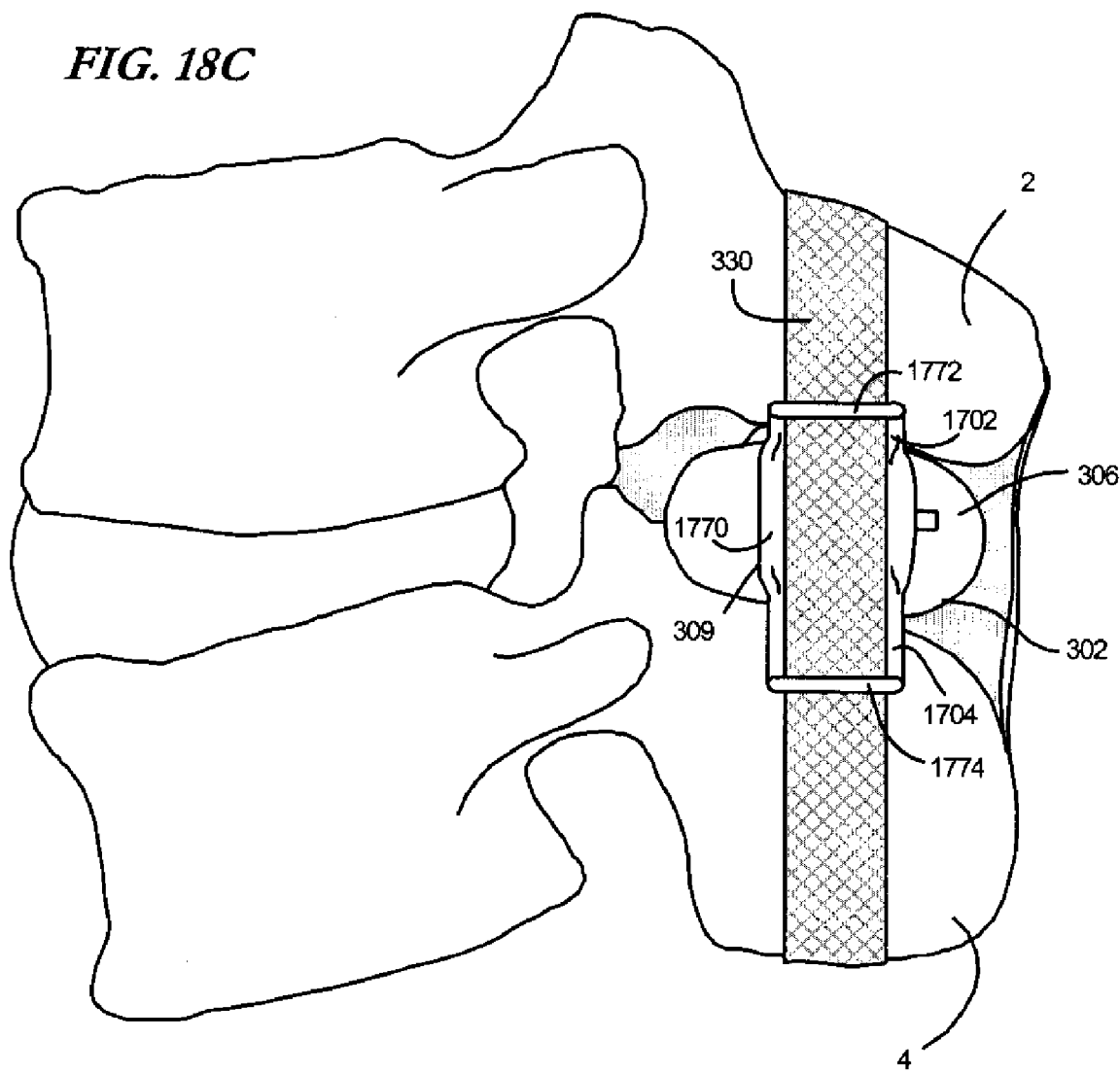
FIG. 18C is a lateral view of the binder aligner of FIGS. 17A, B after implantation of the implant between adjacent spinous processes.

FIG. 18C is a lateral view of the binder aligner of FIGS. 17A, B after implantation of the implant between adjacent spinous processes. As shown in FIG. 18C, the binder aligner 1770 is selectably connectable with the first wing and the binder aligner can receive the binder so that the binder is approximately aligned along a longitudinal axis of the body. An implant comprising a binder aligner 1770 in accordance with the present embodiment of the invention may be implanted in a subject using the method of FIG. 16 described above. During implantation, binder 330 is passed around adjacent spinous processes 2, 4 and passed through guides 1772 and 1774 at either end of binder aligner 1770. The distance between guides 1772 and 1774 reduces the potential for twisting of binder aligner 1770 and main body 101 to which binder aligner 1770 is connected and helps align the binder 330. Thus, binder aligner 1770 in cooperation with binder 330 stabilizes the position of the implant and further stabilizes the adjacent vertebrae. Binder aligner 1770 may be made from an implantable metal or polymer material as described below.

Materials for Use in Implants of the Present Invention

In some embodiments, the implant can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

As described above, the binder can be made from a biocompatible material. In an embodiment, the binder can be made from a braided polyester suture material. Braided polyester suture materials include, for example, Ethibond, Ethiflex, Mersilene, and Dacron, and are nonabsorbable, having high tensile strength, low tissue reactivity and improved handling. In other embodiments, the binder can be made from stainless steel (i.e., surgical steel), which can be braided into a tether or woven into a strap, for example. In still other embodiments, the binder can be made from some other material (or combination of materials) having similar properties.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. A spinal implant comprising:
a body which is positionable between adjacent spinous processes;
a first wing associated with the body and extending along a first longitudinal axis;
a second wing associated with the body and extending along a second longitudinal axis;
a binder adapted to be disposed around the spinous processes;
a binder aligner distinct from the body, first and second wings, and the binder; the binder aligner comprising an elongate member extending along a third longitudinal axis; the binder aligner further comprising first and second guides disposed proximate opposing longitudinal ends of the elongate member and longitudinally spaced from each other in non-overlapping fashion; the first and second guides extending transverse to the third axis;
wherein the binder extends through the first and second guides so as to be generally parallel to the first axis.

2. The implant of claim 1 wherein the second wing can engage the binder such that the binder is aligned with a longitudinal axis of the second wing.

3. The implant of claim 1 wherein at least one of the first and second guides comprises a closed loop through which the binder extends.

4. The implant of claim 1 wherein at least one of the first and second guides comprises an open loop through which the binder extends under tension and wherein the open loop comprises a slot through which the binder may be passed.

5. The implant of claim 1 wherein the binder aligner is abuttingly mounted on the first wing via a fastener.

6. The implant of claim 5 wherein the first wing comprises a mating surface and the binder aligner comprises a complementary surface such that, when the binder aligner is connected with the first wing, the mating surface of the first wing engages the complementary surface of the binder aligner to align the binder aligner with the first wing.

7. The implant of claim 5 wherein the first wing comprises an alignment hole and the binder aligner comprises an alignment pin such that, when the binder aligner is connected with the first wing, the alignment pin engages the alignment hole to align the binder aligner with the first wing.

8. The spinal implant of claim 1 further including a spacer rotatably mounted on said body between the first and second wings.

9. The spinal implant of claim 1 wherein said second wing comprises a capture device that can lock the binder.

* * * * *